(12) United States Patent
Hirabayashi

(10) Patent No.: US 8,979,773 B2
(45) Date of Patent: Mar. 17, 2015

(54) DENTAL TREATMENT DIAGNOSTIC METHOD, METHOD FOR CALCULATING DETERMINATION INDICATORS, PROGRAM AND COMPUTER

(75) Inventor: Daiki Hirabayashi, Matsumoto (JP)

(73) Assignee: Cephmedical Corporation, Matsumoto-Shi (JP)

( * ) Notice: Subject to any disclaimer, the term of this patent is extended or adjusted under 35 U.S.C. 154(b) by 0 days.

(21) Appl. No.: 14/117,743
(22) PCT Filed: Sep. 11, 2012
(86) PCT No.: PCT/JP2012/073180
§ 371 (c)(1),
(2), (4) Date: Dec. 30, 2013
(87) PCT Pub. No.: WO2013/039060
PCT Pub. Date: Mar. 21, 2013

(65) Prior Publication Data
US 2014/0127639 A1    May 8, 2014

(30) Foreign Application Priority Data

Sep. 16, 2011  (JP) ................. 2011-202722
Mar. 26, 2012  (JP) ................. 2012-068857
May 8, 2012  (JP) ................. 2012-106444

(51) Int. Cl.
| | | |
|---|---|---|
| *A61B 5/103* | (2006.01) | |
| *G06K 9/00* | (2006.01) | |
| *A61C 7/00* | (2006.01) | |
| *A61B 6/14* | (2006.01) | |
| *A61C 11/00* | (2006.01) | |

(Continued)

(52) U.S. Cl.
CPC . *A61C 7/002* (2013.01); *A61B 6/14* (2013.01); *A61B 6/501* (2013.01); *A61C 11/00* (2013.01); *A61C 19/04* (2013.01); *A61B 5/1072* (2013.01); *A61C 19/05* (2013.01)
USPC .......................................... 600/587; 382/132

(58) Field of Classification Search
CPC .. A61C 13/0004; A61C 19/04; A61C 19/045; A61B 5/107; A61B 5/1077
USPC ........... 600/587, 589, 595; 382/132, 190, 199
See application file for complete search history.

(56) References Cited

U.S. PATENT DOCUMENTS

| | | |
|---|---|---|
| 6,200,278 B1 | 3/2001 | Arnett |
| 2005/0010450 A1 | 1/2005 | Hultgren |
| 2013/0072793 A1 | 3/2013 | Hirabayashi |

FOREIGN PATENT DOCUMENTS

| | | |
|---|---|---|
| JP | 64-46438 A | 2/1989 |
| WO | WO 00/21457 A1 | 4/2000 |
| WO | WO 03/037204 A1 | 5/2003 |

OTHER PUBLICATIONS

Japanese Patent Office, International Application No. PCT/JP2012/073180 English Translation of International Search Report dated Dec. 11, 2012, pp. 1-4.
Japanese Patent Office, International Application No. PCT/JP2012/073180 Engish Translation of Writtion Opinion dated Feb. 13, 2014, pp. 1-7.
Japanese Patent Office, International Application No. PCT/JP2012/073180 English Translation of International Preliminary Report on Patentability dated Mar. 18, 2014, pp. 1-7.

(Continued)

*Primary Examiner* — Elmer Chao
(74) *Attorney, Agent, or Firm* — Moore & Van Allen PLLC

(57) ABSTRACT

There is provided a method of calculating an index for deciding the necessity of surgically operating on the jaw in orthodontic treatment wherein an index for deciding the necessity of surgically operating on the jaw which becomes objective materials for a dentist to decide the necessity of surgically operating on the jaw of a patient in orthodontic treatment of the patient can be calculated easily, and by appropriately combining the results of other inspection methods, the dentist is able to diagnose easily with high objectivity and correctness, moreover with a short period of time, and its program. Using the distance (S–A) between S and A, the distance (S–$X_i$) between S and $X_i$ (i is an integer from 1 to 4. $X_1$=B, $X_2$=Pog, $X_3$=Gn and $X_4$=Me.) and the distance (Go–$X_j$) between Go and $X_j$ (j is an integer from 1 to 4. j=i or j≠i.) which are measured by the cephalometric radiography of a patient, an index for deciding the necessity of surgically operating on the jaw in orthodontic treatment is calculated by calculating P=((S–$X_i$)+(Go–$X_j$))/(S–A).

15 Claims, 34 Drawing Sheets

(51) Int. Cl.
*A61C 19/04* (2006.01)
*A61B 5/107* (2006.01)
*A61C 19/05* (2006.01)
*A61B 6/00* (2006.01)

(56) References Cited

OTHER PUBLICATIONS

Kameda, Akira, "Diagnostic Method of Orthodontic Clinic," Isho Shuppansha Co., Ltd., 1978, pp. 62-66.

DENTAL TREATMENT DIAGNOSTIC METHOD, METHOD FOR CALCULATING DETERMINATION INDICATORS, PROGRAM AND COMPUTER

CROSS-REFERENCE TO RELATED APPLICATIONS

This application is filed under the provisions of 35 U.S.C. §371 and claims the benefit of International Patent Application No. PCT/JP2012/073180, filed on Sep. 11, 2012, which claims the benefit of Japanese Patent Application No. 2011-202722, filed on Sep. 16, 2011, Japanese Patent Application No. 2012-068857, filed on Mar. 26, 2012, and Japanese Patent Application No. 2012-106444 filed on May 8, 2012, the content of all of which are hereby incorporated by reference in their entirety.

TECHNICAL FIELD

The present invention relates to a method of calculating an index for deciding the necessity of surgically operating on the jaw in orthodontic treatment, a method of deciding the necessity of surgically operating on the jaw in orthodontic treatment, a method of calculating an index for deciding disharmony of the maxilla and mandible, a method of deciding disharmony of the maxilla and mandible, a method of calculating an index for deciding dentofacial deformity, a method of deciding dentofacial deformity, a method of calculating an index for deciding hypogrowth or overgrowth of the maxilla, a method of calculating an index for deciding hypogrowth or overgrowth of the mandible, their programs and a computer comprising these programs. The present invention is suitable, for example, for use when a dentist decides the necessity of surgically operating on the jaw of a patient in orthodontic treatment, or when a dentist or a doctor decides the degree of harmony of the maxilla and mandible (skeletal pattern), or decides dentofacial deformity.

BACKGROUND ART

In orthodontic treatment, some patients may need the surgical operation on the jaw. Conventionally, the necessity of surgical operations on the jaw is decided by taking a cephalometric radiogram (cephalogram) of a patient, and making cephalometric analysis focusing mainly on angle measurements based on the cephalometric radiogram, and according to the results, a dentist decides by making diagnosis (for example, see non-patent literature 1.)

PRIOR ART LITERATURE

Nonpatent Literature

[NONPATENT LITERATURE 1] "Diagnostic Method of Orthodontic Clinic" (Akira Kameda, pp. 62-66, ISHO SHUPPAN CO., Ltd., June, 1978).

SUMMARY OF INVENTION

Subjects to be Solved by Invention

However, the conventional diagnostic method depends on the dentist's experience. As a result, variabilities in diagnosis easily occur by a dentist and it is difficult to make an objective diagnosis. For this, there is a risk that appropriate orthodontic treatment cannot be performed.

On the other hand, if the decision of disharmony of the maxilla and mandible or dentofacial deformity of a patient can be made objectively based on cephalometric analysis, there may be possible to do effective treatment based on the decision. However, heretofore, methods for deciding disharmony of the maxilla and mandible or dentofacial deformity objectively have not been found.

Therefore, a subject to be solved by the present invention is to provide a method of calculating an index for deciding the necessity of surgically operating on the jaw in orthodontic treatment wherein an index for deciding the necessity of surgically operating on the jaw which becomes objective materials for a dentist to decide the necessity of surgically operating on the jaw of a patient in orthodontic treatment of the patient can be calculated easily, and by appropriately combining the results of other inspection methods, the dentist is able to diagnose easily with high objectivity and correctness, moreover with a short period of time and its program.

Another subject to be solved by the present invention is to provide a method of deciding the necessity of surgically operating on the jaw in orthodontic treatment wherein by using an index for deciding the necessity of surgically operating on the jaw which becomes objective materials for a dentist to decide the necessity of surgically operating on the jaw in orthodontic treatment of a patient, and appropriately combining the results of other inspection methods, the dentist is able to diagnose easily with high objectivity and correctness, moreover with a short period of time and its program.

A further subject to be solved by the present invention is to provide a method of calculating an index for deciding disharmony of the maxilla and mandible wherein an index for deciding disharmony of the maxilla and mandible which becomes objective materials for a dentist or a doctor to decide disharmony of the maxilla and mandible of a patient in dental treatment or medical treatment of the patient can be calculated easily, and by appropriately combining the results of other inspection methods, the dentist or doctor is able to make correct diagnoses easily with high objectivity, moreover with a short period of time and its program.

A still further subject to be solved by the present invention is to provide a method of deciding disharmony of the maxilla and mandible wherein by using an index for deciding disharmony of the maxilla and mandible which becomes objective materials for a dentist or a doctor to decide disharmony of the maxilla and mandible of a patient in dental treatment or medical treatment of the patient, and appropriately combining the results of other inspection methods, the dentist or doctor is able to make correct diagnoses easily with high objectivity, moreover with a short period of time and its program.

A further subject to be solved by the present invention is to provide a method of calculating an index for deciding dentofacial deformity wherein an index for deciding dentofacial deformity which becomes objective materials for a dentist or a doctor to decide dentofacial deformity of a patient can be calculated easily, and by appropriately combining the results of other inspection methods, the dentist or doctor is able to make correct diagnoses easily with high objectivity, moreover with a short period of time and its program.

A still further subject to be solved by the present invention is to provide a method of deciding dentofacial deformity wherein by using an index for deciding dentofacial deformity which becomes objective materials for a dentist or a doctor to decide dentofacial deformity of a patient, and by appropriately combining the results of other inspection methods, the dentist or doctor is able to make correct diagnoses easily with high objectivity, moreover with a short period of time and its program.

A still further subject to be solved by the present invention is to provide a method of calculating an index for deciding hypogrowth or overgrowth of the maxilla which becomes objective materials for a dentist or a doctor to decide the presence or absence or the degree of hypogrowth or overgrowth of the maxilla of a patient can be calculated easily, and by appropriately combining the results of other inspection methods, the dentist or doctor is able to make correct diagnoses easily with high objectivity, moreover with a short period of time and its program.

A still further subject to be solved by the present invention is to provide a method of calculating an index for deciding hypogrowth or overgrowth of the mandible which becomes objective materials for a dentist or a doctor to decide the presence or absence or the degree of hypogrowth or overgrowth of the mandible of a patient can be calculated easily, and by appropriately combining the results of other inspection methods, the dentist or doctor is able to make correct diagnoses easily with high objectivity, moreover with a short period of time and its program.

A still further subject to be solved by the present invention is to provide a computer comprising the programs.

Means for Solving the Subjects

In the process of earnest study to solve the subjects, the inventor of the present invention found accidentally that a dentist is able to decide the necessity of surgically operating on the jaw of a patient in orthodontic treatment objectively and easily by measuring the distances between the specific measured points in a cephalometric radiogram, and using the numerals obtained by a calculation based on the special equations using the distances, and confirmed the effectiveness by actually calculating the numerals about many patients. Further, the numerals were found to be effective to decide disharmony of the maxilla and mandible or dentofacial deformity of a patient objectively and easily.

The present invention was worked out as a result of the earnest study based on the knowledge that the inventor obtained uniquely.

To solve the above subject, according to the present invention, there is provided a method of calculating an index for deciding the necessity of surgically operating on the jaw in orthodontic treatment, comprising a step of:

calculating $P=((S-X_i)+(Go-X_j))/(S-A)$ using the distance $(S-A)$ between S and A, the distance $(S-X_i)$ between S and $X_i$ (i is an integer from 1 to 4. $X_1$=B, $X_2$=Pog, $X_3$=Gn and $X_4$=Me.) and the distance $(Go-X_j)$ between Go and $X_j$ (j is an integer from 1 to 4. j=i or j≠i.) which are measured by cephalometric radiography of a patient.

According to the present invention, there is further provided a method of deciding the necessity of surgically operating on the jaw in orthodontic treatment, comprising steps of:

calculating $P=((S-X_i)+(Go-X_j))/(S-A)$ using the distance $(S-A)$ between S and A, the distance $(S-X_i)$ between S and $X_i$ (i is an integer from 1 to 4. $X_1$=B, $X_2$=Pog, $X_3$=Gn and $X_4$=Me.) and the distance $(Go-X_j)$ between Go and $X_j$ (j is an integer from 1 to 4. j=i or j≠i.) which are measured by cephalometric radiography of a patient, or further omitting the figures of the fourth decimal place and under of P, and calculating $Q=(P-[P])\times 1000$ ([ ] denotes Gauss's symbol) (where $2.000 \leq P < 3.000$)

or $Q=(P-([P]+1))\times 1000$ ([ ] denotes Gauss's symbol) (where $P<2.000$); and deciding the necessity of surgically operating on the jaw by deciding whether calculated P or Q is equal to or larger than the predetermined value or not, respectively.

Here, S, A, B, Go, Pog, Gn and Me are measured points to be obtained by cephalometric radiography. The positions of each measured point are shown in FIG. 1. "S" is an abbreviation of Sella, and is a central point of pot-shaped shaded image of the sella turcica of the sphenoid bone. "A" is an abbreviation of the point A, and is the deepest point on the median sagittal plane between ANS (the forefront of the anterior nasal spine, an abbreviation of an anterior nasal spine which is the forefront part of the palatine shelf of maxilla) and the Prosthion which is the most frontal point of an alveolar process between the upper central incisors. "B" is an abbreviation of the point B, and is the deepest point between the Infradentale, the most front point of an alveolar process between the lower central incisors and Pogonion. "Go" is an abbreviation of Gonion, and is a cross point of the angle of the mandible and the bisector of the cross angle between the line connecting the posterior plane of the head of the temporomandibular joint and the posterior part of the angle of the mandible and the mandibular plane. "Pog" is an abbreviation of Pogonion, and is the most protruding point of protuberantia mentalis of the mandible for the Frankfort plane. "Gn" is an abbreviation of Gnathion, and is a cross point of the bone edge image of protuberantia mentalis and the bisector of the angle between the facial plane (the line connecting N (abbreviation of Nasion, and the front point of the frontal suture of the nasal bone) and Pog) and the mandibular plane. "Me" is an abbreviation of the menton, and is the lowest point of the median section image of a chin.

$P=((S-X_i)+(Go-X_j))/(S-A)$ includes, concretely, following equations (1) to (16).

$$P=((S-B)+(Go-Me))/(S-A) \tag{1}$$

$$P=((S-Pog)+(Go-Me))/(S-A) \tag{2}$$

$$P=((S-Gn)+(Go-Me))/(S-A) \tag{3}$$

$$P=((S-Me)+(Go-Me))/(S-A) \tag{4}$$

$$P=((S-B)+(Go-Gn))/(S-A) \tag{5}$$

$$P=((S-Pog)+(Go-Gn))/(S-A) \tag{6}$$

$$P=((S-Gn)+(Go-Gn))/(S-A) \tag{7}$$

$$P=((S-Me)+(Go-Gn))/(S-A) \tag{8}$$

$$P=((S-B)+(Go-Pog))/(S-A) \tag{9}$$

$$P=((S-Pog)+(Go-Pog))/(S-A) \tag{10}$$

$$P=((S-Gn)+(Go-Pog))/(S-A) \tag{11}$$

$$P=((S-Me)+(Go-Pog))/(S-A) \tag{12}$$

$$P=((S-B)+(Go-B))/(S-A) \tag{13}$$

$$P=((S-Pog)+(Go-B))/(S-A) \tag{14}$$

$$P=((S-Gn)+(Go-B))/(S-A) \tag{15}$$

$$P=((S-Me)+(Go-B))/(S-A) \tag{16}$$

The inventor of the present invention measured the distances (S–A), (S–$X_i$) and (Go–$X_j$) in cephalometric radiograms of many patients, and calculated P=((S–$X_i$)+(Go–$X_j$))/(S–A). As a result, it was found that the majority of the patients are to be $$P=((S-X_i)+(Go-X_j))/(S-A)=2 \cdot XYZ$$

(X, Y and Z are integers from 0 to 9).
In other words, P of the majority of the patients is in the range of 2.000≤P<3.000, and only the decimal places are different. However, a few patients may show P<2.000.

As the index for deciding the necessity of surgically operating on the jaw, P itself may be used, but the presentation of integers is easy to understand. For this, in case of 2.000≤P<3.000, for example, after calculating P, further omitting the figures of the fourth decimal place and under of P, Q=(P–[P])×1000 is calculated. [P] denotes omitting decimal places of P, therefore, P–[P] denotes taking out the decimal places of P. Q=(P–[P])×1000 denotes multiplying the decimal places taken out in this way by 1000 times. In this case, it becomes $$P-[P]=2 \cdot XYZ-[2 \cdot XYZ]=2 \cdot XYZ-2=0 \cdot XYZ.$$

Therefore, it becomes Q=(P–[P])×1000=XYZ, and becomes integers from 0 to 999. As an example, in case of P=2.512, it becomes $$Q=(P-[P])\times 1000=(2.512-[2.512])\times 1000=(2.512\times 2)\times 1000=0.512\times 1000=512.$$

P–[P] or numerals XYZ multiplied P–[P] by 1000 times can be considered numerals which evaluate the ratio of the size of the mandible for the maxilla in the profile of a head.

When calculated P or Q is equal to or larger than the predetermined value, respectively, in principle, it can be decided that in orthodontic treatment, the surgical operation is adaptable, in other words, the surgical operation on the jaw, mainly the severing operation on the mandible is necessary. Also, when calculated P or Q is smaller or larger than the predetermined value but not so different from the predetermined value, it is a borderline case. In the borderline case, for example, by the distance (S–N) between S and N, and by Wits analysis (when a vertical line is drawn from each of a point A and a point B for the occlusal plane, the distance between the feet of the vertical lines is Wits), a supplementary analysis is added. In the case that there are problems in the distance (S–N), specifically, for example, in the case that the distance is shorter over 2× standard deviation (2SD) than the average of (S–N), and the results of Wits analysis is equal to or larger than 12 mm, for example, it can be decided that the surgical operation is adaptable, in other words, the surgical operation on the jaw is necessary. As an example, a case that uses the equation (1) is described below. Based on the experience that the inventor of the present invention treats a large number of patients with orthodontic treatment, when the equation (1) is used, generally, for example, in case of P≥2.400 or Q (or XYZ)≥400, in orthodontic treatment, it can be decided that the surgical operation is adaptable, in other words, the surgical operation on the jaw, mainly the severing operation on the mandible is necessary. For this, for example, for the calculated P or Q, by deciding whether P≥2.400 or Q≥400 or not, it can be decided that the surgical operation is adaptable, in other words, the surgical operation on the jaw is necessary. Also, for example, in case of 0.350≤P<2.400 or 350≤Q<400, it is a borderline case. By deciding whether 0.350≤P<2.400 or 350≤Q<400 or not, it can be decided whether it is a borderline case or not. Hereafter, as necessary, Q or an integer XYZ is referred to an OPE index (an operation index).

On the other hand, in case of P<2.000 (generally 1.000≤P<2.000), for example, after calculating P, further omitting the figures of the fourth decimal place and under of P, Q=(P–([P]+1))×1000 is calculated. In this case, it becomes $$P-([P]+1)=1 \cdot XYZ-([1 \cdot XYZ]+1)=1 \cdot XYZ-2.$$

Therefore, it becomes Q=(P–([P]+1))×1000=(1·XYZ–2)×1000, and becomes integers from –1000 to –1. As an example, in case of P=1.912, it becomes Q=(P–([P]+1))×1000=(1.912–([1.912]+1))×1000=(1.912–2)×1000=–0.088×1000=–88.

The method of calculating an index for deciding the necessity of surgically operating on the jaw can be easily executed by a computer comprising the predetermined programs including equations of P and Q. The programs, for example, can be stored in various kinds of computer readable record media such as CD-ROMs, etc., or can be provided through the telecommunications lines such as the Internet, etc. In a computer, as the necessary data for the calculation, for example, the distances (S–A), (S–$X_i$) and (Go–$X_j$) in a cephalometric radiogram are entered. Or taking in the image data to be obtained by cephalometric radiography in a computer, and from the image data, measuring the coordinates of S, A, B, Go, Pog, Gn and Me, from the measured coordinates, the distances (S–A), (S–$X_i$) and (Go–$X_j$) are obtained by calculations, then using the distances, P and Q may be calculated according to the equations.

Also, the method of deciding the necessity of surgically operating on the jaw can be easily executed by a computer comprising the predetermined programs including equations of P and Q or equations for decision of P and Q. The programs are, for example, can be stored in various kinds of computer readable record media such as CD-ROMs, etc., for example, or can be provided through the telecommunications lines such as the Internet, etc. The necessary data for the calculation can be obtained by the same method as the method of calculating an index for deciding the necessity of surgically operating on the jaw.

In the present invention, P=((S–$X_i$)+(Go–$X_j$))/(S–A) is calculated and as necessary, a supplementary analysis is made by the measured values of the distance (S–N). However, it is similarly effective to reflect the distance (S–N) to the equation of P from the beginning More specifically, for example, P'=((S–$X_i$)+(Go–$X_j$))/((S–A)+(S–N)) is used instead of P=((S–$X_i$)+(Go–$X_j$))/(S–A).

In case that P' is used, for example, if necessary, further the figures of the fourth decimal place and under of P' are omitted and $$Q'=(P'-[P'])\times 1000 \text{ ([ ] denotes Gauss's symbol)}$$
$$\text{(where } 1.000 \leq P' < 2.000)$$

or $$Q'=(P'-([P']+1))\times 1000 \text{ ([ ] denotes Gauss's symbol)}$$
$$\text{(where } P' < 1.000)$$

is calculated. And the necessity of surgically operating on the jaw is decided by deciding whether calculated P' or Q' is equal to or larger than the predetermined value or not, respectively. As an example, described below is a case where $X_i$=B and $X_j$=Me in the equation P'=((S–$X_i$)+(Go–$X_j$))/((S–A)+(S–N)). In case of P'≥1.330 or Q' (or XYZ)≥330, for example, in orthodontic treatment, it can be decided that the surgical operation is adaptable, in other words, the surgical operation on the jaw, mainly the severing operation on the mandible is necessary. For this, for example, for the calculated P' or Q', by deciding whether P'≥1.330 or Q'≥330 or not, it can be decided that the surgical operation is adaptable, in other words, the surgical operation on the jaw is necessary. Therefore, for example, by deciding whether P'≥1.330 or Q'≥330 for the calculated P' or Q', it can be decided that the surgical operation is adaptable, in other words, the surgical operation on the jaw is necessary. Also, for example, in case of 1.270≤P'<1.330 or 270≤Q<330, it is a borderline case. By deciding whether 1.270≤P<1.330 or 270<Q<330 or not, it can be decided whether it is a borderline case or not.

The method of calculating an index for deciding the necessity of surgically operating on the jaw is easily executed by a computer comprising the predetermined programs including equations of P' and Q'. The programs can be stored in various kinds of computer readable record media such as CD-ROMs, etc., for example, or can be provided through the telecommunications lines such as the Internet, etc. In a computer, as necessary data for calculation, for example, the distances (S-A), (S-N), (S-$X_i$) and (Go-$X_j$) in the cephalometric radiogram are entered. Or, for example, the image data to be obtained by cephalometric radiography is taken in a computer, the coordinates of S, A, N, B, Go, Pog, Gn and Me are measured from the image data, the distances (S-A), (S-N), (S-$X_i$) and (Go-$X_j$) are obtained by calculations from the coordinates measured by this, and P' and Q' may be calculated according to the equations using the distances.

Also, the method of deciding the necessity of surgically operating on the jaw can be easily executed by a computer comprising the predetermined programs including equations of P' and Q' or equations for decision of P' and Q'. The programs can be stored in various kinds of computer readable record media such as CD-ROMs, etc., for example, or can be provided through the telecommunications lines such as the Internet, etc. The necessary data for the calculation can be obtained as the same as the method of calculating an index for deciding the necessity of surgically operating on the jaw.

According to the present invention, there is also provided a method of calculating an index for deciding disharmony of the maxilla and mandible, comprising a step of:

calculating $P=((S-X_i)+(Go-X_j))/(S-A)$ using the distance (S-A) between S and A, the distance (S-$X_i$) between S and $X_i$ (i is an integer from 1 to 4. $X_1$=B, $X_2$=Pog, $X_3$=Gn and $X_4$=Me.) and the distance (Go-$X_j$) between Go and $X_j$ (j is an integer from 1 to 4. j=i or j≠i.) which are measured by cephalometric radiography of a patient.

According to the present invention, there is also provided a method of deciding disharmony of the maxilla and mandible, comprising steps of:

calculating $P=((S-X_i)+(Go-X_j))/(S-A)$ using the distance (S-A) between S and A, the distance (S-$X_i$) between S and $X_i$ (i is an integer from 1 to 4. $X_1$=B, $X_2$=Pog, $X_3$=Gn and $X_4$=Me.) and the distance (Go-$X_j$) between Go and $X_j$ (j is an integer from 1 to 4. j=i or j≠i.) which are measured by cephalometric radiography of a patient, or further omitting the figures of the fourth decimal place and under of P, and calculating $Q=(P-[P])\times1000$ ([ ] denotes Gauss's symbol) (where 2.000≤$P$<3.000)

or $Q=(P-([P]+1))\times1000$ ([ ] denotes Gauss's symbol) (where $P$<2.000); and deciding disharmony of the maxilla and mandible by deciding whether calculated P or Q is equal to or larger than the predetermined value or not, respectively.

According to the present invention, there is also provided a method of calculating an index for deciding dentofacial deformity, comprising a step of:

calculating $P=((S-X_i)+(Go-X_j))/(S-A)$ using the distance (S-A) between S and A, the distance (S-$X_i$) between S and $X_i$ (i is an integer from 1 to 4. $X_1$=B, $X_2$=Pog, $X_3$=Gn and $X_4$=Me.) and the distance (Go-$X_j$) between Go and $X_j$ (j is an integer from 1 to 4. j=i or j≠i.) which are measured by cephalometric radiography of a patient.

According to the present invention, there is also provided a method of deciding dentofacial deformity, comprising steps of:

calculating $P=((S-X_i)+(Go-X_j))/(S-A)$ using the distance (S-A) between S and A, the distance (S-$X_i$) between S and $X_i$ (i is an integer from 1 to 4. $X_1$=B, $X_2$=Pog, $X_3$=Gn and $X_4$=Me.) and the distance (Go-$X_j$) between Go and $X_j$ (j is an integer from 1 to 4. j=i or j≠i.) which are measured by cephalometric radiography of a patient, or further omitting the figures of the fourth decimal place and under of P, and calculating $Q=(P-[P])\times1000$ ([ ] denotes Gauss's symbol) (where 2.000≤$P$<3.000)

or $Q=(P-([P]+1))\times1000$ ([ ] denotes Gauss's symbol) (where $P$<2.000); and deciding whether the patient suffers from dentofacial deformity by deciding whether calculated P or Q is equal to or larger than the predetermined value or not, respectively.

In the above-mentioned inventions of the method of calculating an index for deciding disharmony of the maxilla and mandible, the method of deciding disharmony of the maxilla and mandible, the method of calculating an index for deciding dentofacial deformity and the method of deciding dentofacial deformity, unless contrary to the nature, the explanation of the inventions of the method of calculating an index for deciding the necessity of surgically operating on the jaw and the method of deciding the necessity of surgically operating on the jaw come into effect.

Here, the method of calculating an index for deciding disharmony of the maxilla and mandible and the method of deciding disharmony of the maxilla and mandible are effective for deciding disharmony of the maxilla and mandible in various kinds of treatment which are effective to treat according to disharmony of the maxilla and mandible. The treatment includes both the dental treatment and the medical treatment. For example, the dental treatment includes various kinds of treatments which are effective to treat according to disharmony of the maxilla and mandible, specifically, for example, other than orthodontic treatment, also includes prosthesis such as artificial teeth (false teeth), etc.

According to the present invention, there is also provided a method of calculating an index for deciding the necessity of surgically operating on the jaw in orthodontic treatment, comprising a step of:

calculating $P=((S-B)+(Go-B)+(Go-Me))/((S-A)+(Go-A))$ using the distance (S-A) between S and A, the distance (Go-A) between Go and A, the distance (S-B) between S and B, the distance (Go-B) between Go and B and the distance (Go-Me) between Go and Me which are measured by cephalometric radiography of a patient.

According to the present invention, there is also provided a method of deciding the necessity of surgically operating on the jaw in orthodontic treatment, comprising steps of:

calculating $P=((S-B)+(Go-B)+(Go-Me))/((S-A)+(Go-A))$ using the distance (S-A) between S and A, the distance (Go-A) between Go and A, the distance (S-B) between S and B, the distance (Go-B) between Go and B and the distance (Go-Me) between Go and Me which are measured by cephalometric radiography of a patient, or further omitting the figures of the fourth decimal place and under of P and calculating $Q=(P-[P])\times1000$ ([ ] denotes Gauss's symbol) (where $1.000 \le P < 2.000$)

or $Q=(P-([P]+1))\times1000$ ([ ] denotes Gauss's symbol) (where $P<1.000$); and deciding the necessity of surgically operating on the jaw by deciding whether calculated P or Q is equal to or larger than the predetermined value or not, respectively.

According to the present invention, there is also provided a method of calculating an index for deciding disharmony of the maxilla and mandible, comprising a step of:

calculating $P=((S-B)+(Go-B)+(Go-Me))/((S-A)+(Go-A))$ using the distance (S–A) between S and A, the distance (Go–A) between Go and A, the distance (S–B) between S and B, the distance (Go–B) between Go and B and the distance (Go–Me) between Go and Me which are measured by cephalometric radiography of a patient.

According to the present invention, there is also provided a method of deciding disharmony of the maxilla and mandible, comprising steps of:

calculating $P=((S-B)+(Go-B)+(Go-Me))/((S-A)+(Go-A))$ using the distance (S–A) between S and A, the distance (Go–A) between Go and A, the distance (S–B) between S and B, the distance (Go–B) between Go and B and the distance (Go–Me) between Go and Me which are measured by cephalometric radiography of a patient, or further omitting the figures of the fourth decimal place and under of P, and calculating $Q=(P-[P])\times1000$ ([ ] denotes Gauss's symbol) (where $1.000 \le P < 2.000$)

or $Q=(P-([P]+1))\times1000$ ([ ] denotes Gauss's symbol) (where $P<1.000$); and deciding disharmony of the maxilla and mandible by deciding whether calculated P or Q is equal to or larger than the predetermined value or not, respectively.

According to the present invention, there is also provided a method of calculating an index for deciding dentofacial deformity, comprising a step of:

calculating $P=((S-B)+(Go-B)+(Go-Me))/((S-A)+(Go-A))$ using the distance (S–A) between S and A, the distance (Go–A) between Go and A, the distance (S–B) between S and B, the distance (Go–B) between Go and B and the distance (Go–Me) between Go and Me which are measured by cephalometric radiography of a patient.

According to the present invention, there is also provided a method of deciding dentofacial deformity, comprising steps of:

calculating $P=((S-B)+(Go-B)+(Go-Me))/((S-A)+(Go-A))$ using the distance (S–A) between S and A, the distance (Go–A) between Go and A, the distance (S–B) between S and B, the distance (Go–B) between Go and B and the distance (Go–Me) between Go and Me which are measured by cephalometric radiography of a patient, or further omitting the figures of the fourth decimal place and under of P, and calculating $Q=(P-[P])\times1000$ ([ ] denotes Gauss's symbol) (where $1.000 \le P < 2.000$)

or $Q=(P-([P]+1))\times1000$ ([ ] denotes Gauss's symbol) (where $P<1.000$); and deciding whether the patient suffers from dentofacial deformity by deciding whether calculated P or Q is equal to or larger than the predetermined value or not, respectively.

In the above-mentioned inventions of the method of calculating an index for deciding the necessity of surgically operating on the jaw in orthodontic treatment, the method of deciding the necessity of surgically operating on the jaw in orthodontic treatment, the method of calculating an index for deciding disharmony of the maxilla and mandible, the method of deciding disharmony of the maxilla and mandible, the method of calculating an index for deciding dentofacial deformity and the method of deciding dentofacial deformity that use the equation $P=((S-B)+(Go-B)+(Go-Me))/((S-A)+(Go-A))$, unless contrary to the nature, the explanation of each invention mentioned above that use the equation $P=((S-X_i)+(Go-X_j))/(S-A)$ come into effect. Also, the methods of the inventions can be easily executed by a computer comprising the predetermined programs including equation of P and Q or equation for decision of P and Q.

By the way, in the method of deciding the necessity of surgically operating on the jaw in orthodontic treatment, the method of deciding disharmony of the maxilla and mandible and the method of deciding dentofacial deformity, it is effective to consider the degree of growth of the maxilla or mandible in order to make more correct and objective decision. The reason is that it can be the reference for deciding the method of treatment or the reference denoting the difficulty of treatment. More specifically, it is effective to examine whether it is maxillary protrusion or not, what kind of pattern it is in case of maxillary protrusion, whether it is mandibular protrusion or not, what kind of pattern it is in case of mandibular protrusion. The maxillary protrusion is, concretely, classified as follows.

1. Hypogrowth of the maxilla (the maxilla hypogrowth)+hypogrowth of the mandible (the mandible hypogrowth)
2. The maxilla normal+hypogrowth of the mandible
3. Overgrowth of the maxilla+the mandible normal
4. Overgrowth of the maxilla+hypogrowth of the mandible Also, the mandibular protrusion is classified as follows.
1. Hypogrowth of the maxilla+the mandible normal
2. Hypogrowth of the maxilla+overgrowth of the mandible
3. The maxilla normal+overgrowth of the mandible
4. Overgrowth of the maxilla+overgrowth of the mandible For example, serious hypogrowth of the maxilla needs surgically operating on the maxilla in orthodontic treatment or dentofacial deformity treatment.

As a result of earnest study, the inventor of the present invention found effective indices showing the presence or absence or the degree of hypogrowth or overgrowth of the maxilla or hypogrowth or overgrowth of the mandible and worked out inventions mentioned below.

According to the present invention, there is provided a method of calculating an index for deciding hypogrowth or overgrowth of the maxilla, comprising a step of:

calculating P by using at least one equation of following equations (17) to (19) using the distance (S–N) between S and N, the distance (S–A) between S and A and the distance (Go–A) between Go and A which are measured by cephalometric radiography of a patient.

$$P=((S-A)+(Go-A))/(S-N) \qquad (17)$$

$$P=(S-A)/(S-N) \qquad (18)$$

$$P=(S-A)-(S-N) \qquad (19)$$

In case that P is calculated according to the equation (17), as necessary, further the figures of the fourth decimal place and under of P are omitted and $Q=(P-[P])\times 1000$ ([ ] denotes Gauss's symbol) (where $2.000 \leq P<3.000$)

or $Q=(P-([P]+1))\times 1000$ ([ ] denotes Gauss's symbol) (where $P<2.000$)

is calculated.

In case that P is calculated according to the equation (18), as necessary, further the figures of the fourth decimal place and under of P are omitted and $Q=(P-[P])\times 1000$ ([ ] denotes Gauss's symbol) (where $1.000 \leq P<2.000$)

or $Q=(P-([P]+1))\times 1000$ ([ ] denotes Gauss's symbol) (where $P<1.000$)

is calculated.

Hereafter, as necessary, Q or P that is calculated according to the equation (19) is simply referred to an index of hypogrowth of the maxilla. Here, there is more hypogrowth tendency of the maxilla as Q or P that is calculated according to the equation (19) is the less value and there is more overgrowth tendency of the maxilla as Q or P that is calculated according to the equation (19) is the larger value. For example, for Q calculated using P that is calculated according to the equation (17), for example, it can be decided that the maxilla is normal in case that Q is equal to or larger than 200 and equal to or less than 450, the maxilla shows hypogrowth in case that Q is equal to or larger than 100 and less than 200, the maxilla shows serious hypogrowth in case that Q is less than 100, and the maxilla shows overgrowth in case that Q is equal to or larger than 500.

According to the present invention, there is also provided a method of calculating an index for deciding hypogrowth or overgrowth of the mandible, comprising a step of:

calculating P by using at least one equation of following equations (20) to (24) using the distance (S–N) between S and N, the distance (S–A) between S and A, the distance (S–B) between S and B, the distance (Go–B) between Go and B and the distance (Go–Me) between Go and Me which are measured by cephalometric radiography of a patient.

$$P=((S-B)+(Go-B)+(Go-Me))/((S-N)+(S-A)) \quad (20)$$

$$P=((S-B)+(Go-B))/((S-N)+(S-A)) \quad (21)$$

$$P=((S-B)+(Go-B))/(S-N) \quad (22)$$

$$P=(S-B)/(S-N) \quad (23)$$

$$P=(S-B)-(S-N) \quad (24)$$

In case that P is calculated according to the equation (20), (21) or (23), as necessary, further the figures of the fourth decimal place and under of P are omitted and $Q=(P-[P])\times 1000$ ([ ] denotes Gauss's symbol) (where $1.000 \leq P<2.000$)

or $Q=(P-([P]+1))\times 1000$ ([ ] denotes Gauss's symbol) (where $P<1.000$)

is calculated.

In case that P is calculated according to the equation (22), as necessary, further the figures of the fourth decimal place and under of P are omitted and $Q=(P-[P])\times 1000$ ([ ] denotes Gauss's symbol) (where $2.000 \leq P<3.000$)

or $Q=(P-[P]+1)\times 1000$ ([ ] denotes Gauss's symbol) (where $3.000 \leq P<4.000$)

is calculated.

Hereafter, as necessary, Q or P that is calculated according to the equation (24) is simply referred to an index of hypogrowth of the mandible. Here, there is more hypogrowth tendency of the mandible as Q or P that is calculated according to the equation (24) is the less value and there is more overgrowth tendency of the mandible as Q or P that is calculated according to the equation (24) is the larger value. For example, for Q calculated using P that is calculated according to the equation (22), for example, it can be decided that the mandible is normal in case that Q is equal to or larger than 500 and equal to or less than 600, the mandible shows hypogrowth in case that Q is equal to or larger than 400 and less than 500, the mandible shows serious hypogrowth in case that Q is less than 400, the mandible shows overgrowth in case that Q is larger than 600 and less than 900, and the mandible shows serious overgrowth in case that Q is larger than 900.

The ratio of P given by the equation (22) to P given by the equation (17), i.e., $[((S-B)+(Go-B))/(S-N)]/[((S-A)+(Go-A))/(S-N)]=((S-B)+(Go-B))/((S-A)+(Go-A))$, can be used as an index for deciding the necessity of surgically operating on the jaw in orthodontic treatment, an index for deciding disharmony of the maxilla and mandible or an index for deciding dentofacial deformity.

Therefore, according to the present invention, there is provided a method of calculating an index for deciding the necessity of surgically operating on the jaw in orthodontic treatment, comprising a step of:

calculating $P=((S-B)+(Go-B))/((S-A)+(Go-A))$ using the distance (S–A) between S and A, the distance (S–B) between S and B, the distance (Go–A) between Go and A and the distance (Go–B) between Go and B which are measured by cephalometric radiography of a patient.

According to the present invention, there is also provided a method of calculating an index for deciding disharmony of the maxilla and mandible, comprising a step of:

calculating $P=((S-B)+(Go-B))/((S-A)+(Go-A))$ using the distance (S–A) between S and A, the distance (S–B) between S and B, the distance (Go–A) between Go and A and the distance (Go–B) between Go and B which are measured by cephalometric radiography of a patient.

According to the present invention, there is also provided a method of calculating an index for deciding dentofacial deformity, comprising a step of:

calculating $P=((S-B)+(Go-B))/((S-A)+(Go-A))$ using the distance (S–A) between S and A, the distance (S–B) between S and B, the distance (Go–A) between Go and A and the distance (Go–B) between Go and B which are measured by cephalometric radiography of a patient.

In case that $P=((S-B)+(Go-B))/((S-A)+(Go-A))$ is calculated, as necessary, further 2P is calculated and the figures of the fourth decimal place and under of 2P are omitted and $Q=(2P-[2P])\times 1000$ ([ ] denotes Gauss's symbol) (where $2.000<2P<3.000$)

or $Q=(2P-([2P]+1))\times 1000$ ([ ] denotes Gauss's symbol) (where $2P<2.000$)

is calculated.

In the method of calculating an index for deciding hypogrowth or overgrowth of the maxilla, the method of calculating an index for deciding hypogrowth or overgrowth of the mandible or the method of deciding hypogrowth or overgrowth of the maxilla and the method of deciding hypogrowth or overgrowth of the mandible based on the index calculated using those calculating methods, the method of calculating an index for deciding the necessity of surgically operating on the jaw in orthodontic treatment, the method of calculating an index for deciding disharmony of the maxilla and mandible, the method of calculating an index for deciding dentofacial deformity using the equation $P=((S-B)+(Go-B))/((S-A)+(Go-A))$ or the method of deciding the necessity of surgically operating on the jaw, the method of deciding disharmony of the maxilla and mandible and the method of deciding dentofacial deformity based on the index calculated by those calculating methods, unless contrary to the nature, the explanation mentioned above relative to each invention that use the equation $P=((S-X_i)+(Go-X_j))/(S-A)$ come into effect. Also, the methods of the present invention can be easily executed by a computer comprising the predetermined programs including equation of P and Q or equation for decision of P and Q.

Effect of the Invention

According to the present invention, an index for deciding the necessity of surgically operating on the jaw which becomes objective materials for a dentist to decide the necessity of surgically operating on the jaw of a patient in orthodontic treatment of the patient can be easily calculated, and by appropriately combining the results of other inspection methods, the dentist is able to make more correct diagnosis with higher objectivity easily, moreover with a short period of time. Also, an index for deciding disharmony of the maxilla and mandible which becomes objective materials for a dentist or a doctor to decide disharmony of the maxilla and mandible of a patient in dental treatment such as orthodontic treatment, etc. and medical treatment of the patient can be easily calculated, and by appropriately combining the results of other inspection methods, the dentist or doctor is able to make more correct diagnosis easily with higher objectivity, moreover with a short period of time. Also, an index for deciding dentofacial deformity which becomes objective materials for a dentist or a doctor to decide whether a patient suffers from dentofacial deformity or not can be easily calculated, and by appropriately combining the results of other inspection methods, the dentist or doctor is able to make more correct diagnosis easily with higher objectivity, moreover with a short period of time. Also, an index for deciding hypogrowth or overgrowth of the maxilla which becomes the objective materials for a dentist or a doctor to decide the presence or absence or the degree of hypogrowth or overgrowth of the maxilla of a patient can be easily calculated and, by appropriately combining the results of other inspection methods, the dentist or doctor is able to make more correct diagnosis easily with higher objectivity, moreover with a short period of time. Also, an index for deciding hypogrowth or overgrowth of the mandible which becomes objective materials for a dentist or a doctor to decide the presence or absence or the degree of hypogrowth or overgrowth of the mandible can be easily calculated, and by appropriately combining the results of other inspection methods, the dentist or doctor is able to make more correct diagnosis easily with higher objectivity, moreover with a short period of time.

MODES FOR CARRYING OUT THE INVENTION

Modes for carrying out the invention (hereafter referred as "embodiments") will now be explained below.

1. First Embodiment

In the first embodiment, a method of calculating an OPE index as an index for deciding the necessity of surgically operating on the jaw in orthodontic treatment is explained.

Figure 1:
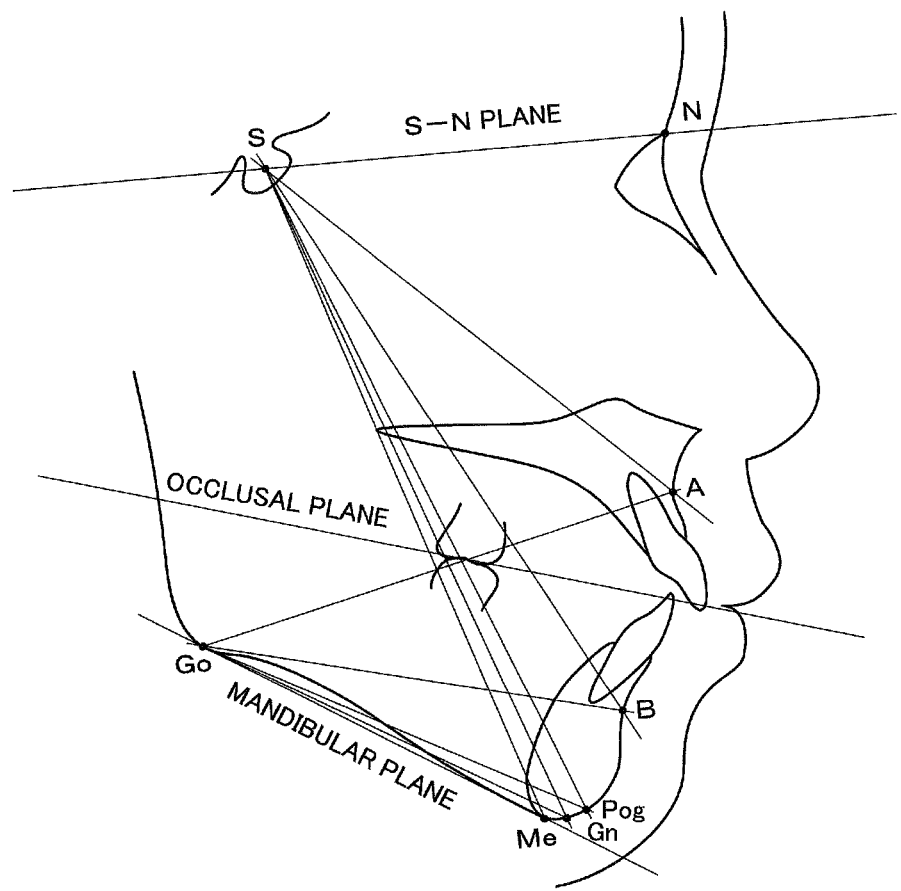
FIG. 1 A schematic drawing for explaining the measured points in a cephalometric radiogram.
Figure 2:
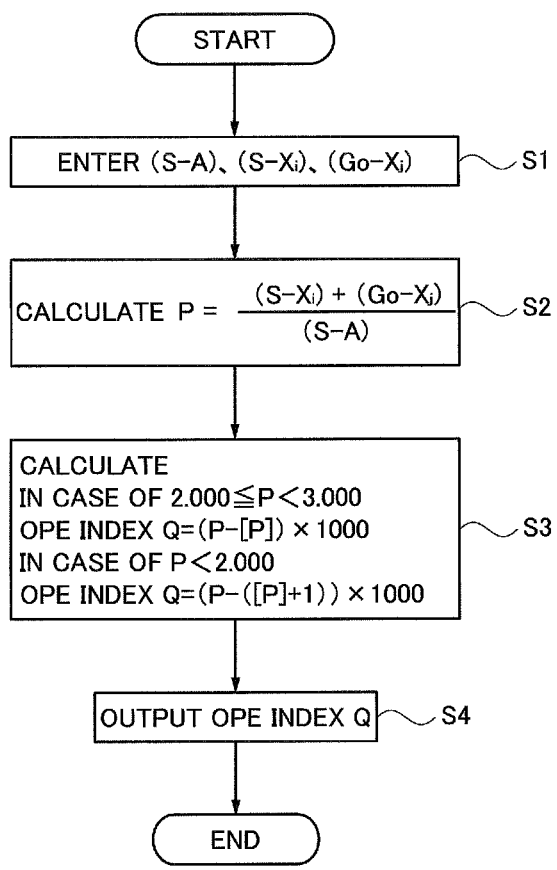
FIG. 2 A flowchart showing a method of calculating an index for deciding the necessity of surgically operating on the jaw in orthodontic treatment according to the first embodiment of the present invention.

FIG. 2 shows a flowchart of the method of calculation. Programs are created according to the flowchart, and are executed on a computer.

Before making the calculation, taking a cephalometric radiogram of a patient to be treated by orthodontic treatment, the distance (S–A) between S and A, the distance (S–$X_i$) between S and $X_i$ and the distance (Go–$X_j$) between Go and $X_j$ are measured. The measurement of the distances can be easily executed by entering the coordinate data of measured points of S, A, $X_i$ ($X_i$=B, $X_2$=Pog, $X_3$=Gn and $X_4$=Me) and Go on the cephalometric radiogram, for example, by using a pen tablet or a digitizer. Or, by taking the image data to be obtained by cephalometric radiography in a computer, and measuring the coordinates of S, A, $X_i$ ($X_i$=B, $X_2$=Pog, $X_3$=Gn and $X_4$=Me) and Go from the image data, the distances (S–A), (S–$X_i$) and (Go–$X_j$) may be obtained by calculations from the measured coordinates.

As shown in FIG. 2, in step S1, the distances (S–A), (S–$X_i$) and (Go–$X_j$) which are measured by the above are entered.

In step S2, from the entered (S–A), (S–$X_i$) and (Go–$X_j$), P is calculated according to $$P=((S-X_i)+(Go-X_j))/(S-A).$$

In step S3, the figures of the fourth decimal place and under of P obtained by the above calculation are omitted, and in case of $2.000 \leq P < 3.000$, an OPE index Q is calculated according to $Q=(P-[P]) \times 1000$, and in case of $P<2.000$, an OPE index Q is calculated according to $Q=(P-([P]+1)) \times 1000$.

In step S4, the OPE index Q calculated as the above is output on a display, for example.

In case that the OPE index Q calculated like this is equal to or larger than the predetermined data ($C_1$), it can be diagnosed that in principle, the severing operation on the mandible is necessary in orthodontic treatment. Also, in case that the OPE index Q is equal to or larger than $C_2$ and less than $C_1$, or in case that the OPE index Q is equal to or larger than $C_1$ but not so different from $C_1$, which is a borderline case, a supplementary analysis is added by the distance (S–N) and Wits analysis. For example, in case that the distance (S–N) is shorter over 2SD than the average, when the result of Wits analysis is equal to or larger than 12 mm, it is decided that the surgical operation is adaptable, in other words, the surgical operation on the jaw is necessary. $C_1$ and $C_2$ can be decided suitably according to choice of any one of the above equations (1) to (16). Generally, for example, $C_1$ is equal to or larger than 400 and less than 680, and $C_2$ is less than $C_1$ by a value equal to or larger than 30 and less than 100.

In case that the OPE index Q is less than $C_2$ and equal to or larger than 0, it can be decided that in orthodontic treatment, the surgical operation on the jaw is not necessary.

In case that the OPE index Q is negative, it means also remarkable hypogrowth of the mandible or overgrowth of the maxilla, and it is necessary to consider the surgical operation on the jaw.

Generally, in addition to the OPE index Q, a dentist finally decides the necessity of surgically operating on the jaw by combining the results of other inspection such as conventional cephalometric analysis, etc. focusing mainly on the angle measurement.

Example 1

Figure 3:
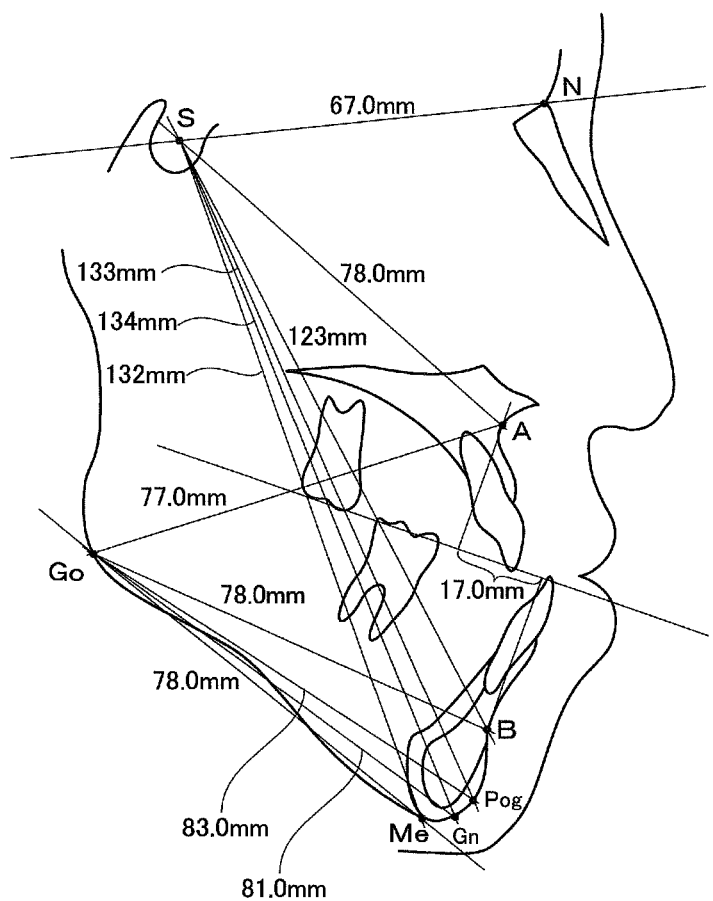
FIG. 3 A tracing made based on a cephalometric radiogram of a patient 1.

A cephalometric radiogram of a patient 1 was taken. It was taken on the central occlusal position or the proportional position (similar in examples 2 to 12 described below). FIG. 3 shows a tracing made based on the cephalometric radiogram.

From FIG. 3, the distances (S–A), (S–B), (S–Pog), (S–Gn), (S–Me), (Go–B), (Go–Pog), (Go–Gn) and (Go–Me) were measured. Measured distances are shown in FIG. 3. Using the data, P was calculated by the equations (1) to (16). The results are as follows. It is to be noted that (S–N)=67.0 mm and Wits=17.0 mm.

$P=(123.0+78.0)/78.0=2.5769$. The OPE index $Q=576$.  Equation (1)

For example, if $C_1$ is set as $C_1=400$, as the OPE index Q is 576, it can be decided that the patient 1 suffers from dentofacial deformity and in orthodontic treatment, the severing operation on the mandible is necessary.

$P=(133.0+78.0)/78.0=2.7051$. The OPE index $Q=705$.  Equation (2)

For example, if $C_1$ is set as $C_1=585$, as the OPE index Q is 705, it can be decided as the same as the case of Equation (1).

$P=(134.0+78.0)/78.0=2.7179$. The OPE index $Q=717$.  Equation (3)

For example, if $C_1$ is set as $C_1=600$, as the OPE index Q is 717, it can be decided as the same as the case of Equation (1).

$P=(132.0+78.0)/78.0=2.6923$. The OPE index $Q=692$.  Equation (4)

For example, if $C_1$ is set as $C_1=585$, as the OPE index Q is 692, it can be decided as the same as the case of Equation (1).

$P=(123.0+81.0)/78.0=2.6153$. The OPE index $Q=615$.  Equation (5)

For example, if $C_1$ is set as $C_1=475$, as the OPE index Q is 615, it can be decided as the same as the case of Equation (1).

$P=(133.0+81.0)/78.0=2.7435$. The OPE index $Q=743$.  Equation (6)

For example, if $C_1$ is set as $C_1=630$, as the OPE index Q is 743, it can be decided as the same as the case of Equation (1).

$$P=(134.0+81.0)/78.0=2.7564.\text{ The OPE index }Q=756. \quad \text{Equation (7)}$$

For example, if $C_1$ is set as $C_1=660$, as the OPE index Q is 756, it can be decided as the same as the case of Equation (1).

$$P=(132.0+81.0)/78.0=2.7307.\text{ The OPE index }Q=730. \quad \text{Equation (8)}$$

For example, if $C_1$ is set as $C_1=650$, as the OPE index Q is 730, it can be decided as the same as the case of Equation (1)

$$P=(123.0+83.0)/78.0=2.6410.\text{ The OPE index }Q=641. \quad \text{Equation (9)}$$

For example, if $C_1$ is set as $C_1=490$, as the OPE index Q is 641, it can be decided as the same as the case of Equation (1).

$$P=(133.0+83.0)/78.0=2.7692.\text{ The OPE index }Q=769. \quad \text{Equation (10)}$$

For example, if $C_1$ is set as $C_1=645$, as the OPE index Q is 769, it can be decided as the same as the case of Equation (1).

$$P=(134.0+83.0)/78.0=2.7820.\text{ The OPE index }Q=782. \quad \text{Equation (11)}$$

For example, if $C_1$ is set as $C_1=675$, as the OPE index Q is 782, it can be decided as the same as the case of Equation (1).

$$P=(132.0+83.0)/78.0=2.7564.\text{ The OPE index }Q=756. \quad \text{Equation (12)}$$

For example, if $C_1$ is set as $C_1=665$, as the OPE index Q is 756, it can be decided as the same as the case of Equation (1).

$$P=(123.0+78.0)/78.0=2.5769.\text{ The OPE index }Q=576. \quad \text{Equation (13)}$$

For example, if $C_1$ is set as $C_1=435$, as the OPE index Q is 576, it can be decided as the same as the case of Equation (1).

$$P=(133.0+78.0)/78.0=2.7050.\text{ The OPE index }Q=705. \quad \text{Equation (14)}$$

For example, if $C_1$ is set as $C_1=575$, as the OPE index Q is 705, it can be decided as the same as the case of Equation (1).

$$P=(134.0+78.0)/78.0=2.7179.\text{ The OPE index }Q=717. \quad \text{Equation (15)}$$

For example, if $C_1$ is set as $C_1=610$, as the OPE index Q is 717, it can be decided as the same as the case of Equation (1).

$$P=(132.0+78.0)/78.0=2.6923.\text{ The OPE index }Q=692. \quad \text{Equation (16)}$$

For example, if $C_1$ is set as $C_1=600$, as the OPE index Q is 692, it can be decided as the same as the case of Equation (1).

Therefore, the necessary severing operation on the mandible was performed. After the severing operation, a cephalometric radiogram of the patient 1 was taken. A tracing made based on the cephalometric radiogram is shown in FIG. 4.

Figure 4:
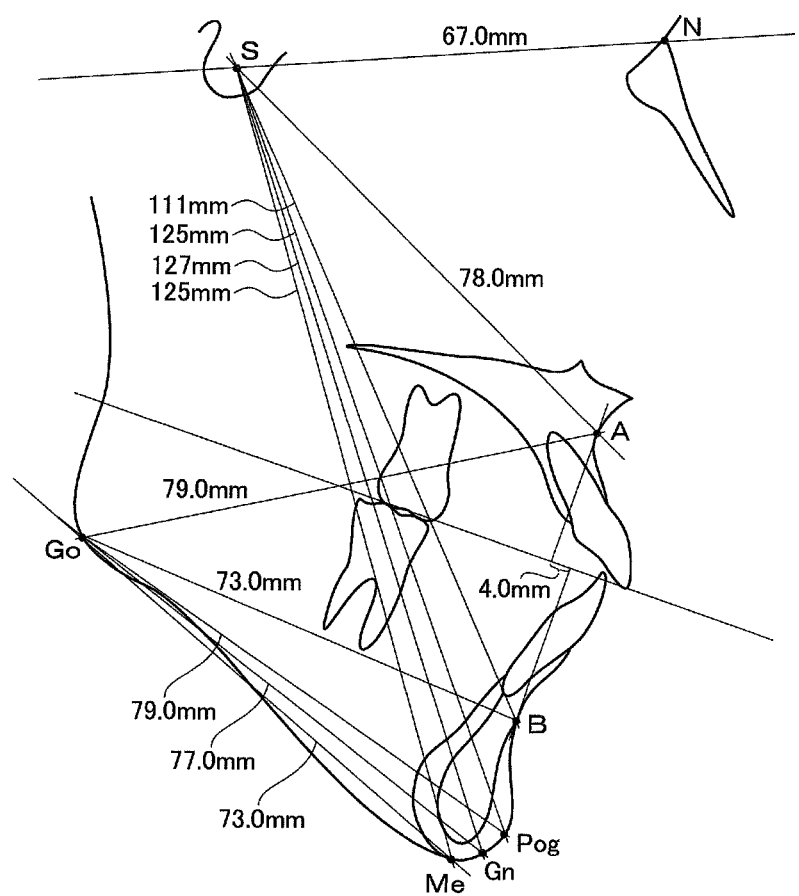
FIG. 4 A tracing made based on a cephalometric radiogram taken after the severing operation on the mandible of the patient 1.

From FIG. 4, the distances (S–A), (S–B), (S–Pog), (S–Gn), (S–Me), (Go–B), (Go–Pog), (Go–Gn) and (Go–Me) were measured. Measured distances are shown in FIG. 4. Using the data, P was calculated by the equations (1) to (16). The results are as follows. It is to be noted that (S–N)=67.0 mm and Wits=4.0 mm.

$$P=(111.0+73.0)/78.0=2.3589.\text{ The OPE index }Q=358. \quad \text{Equation (1)}$$

For $C_1=400$, the OPE index Q is 358, so it can be decided that the patient 1 is able to be treated by orthodontic treatment as a result of the severing operation on the mandible.

$$P=(125.0+73.0)/78.0=2.5384.\text{ The OPE index }Q=538. \quad \text{Equation (2)}$$

For $C_1=585$, the OPE index Q is 538, so it can be decided as the same as the case of Equation (1).

$$P=(127.0+73.0)/78.0=2.5641.\text{ The OPE index }Q=564. \quad \text{Equation (3)}$$

For $C_1=600$, the OPE index Q is 564, so it can be decided as the same as the case of Equation (1).

$$P=(125.0+73.0)/78.0=2.5384.\text{ The OPE index }Q=538. \quad \text{Equation (4)}$$

For $C_1=585$, the OPE index Q is 538, so it can be decided as the same as the case of Equation (1).

$$P=(111.0+77.0)/78.0=2.4102.\text{ The OPE index }Q=410. \quad \text{Equation (5)}$$

For $C_1=475$, the OPE index Q is 410, so it can be decided as the same as the case of Equation (1).

$$P=(125.0+77.0)/78.0=2.5897.\text{ The OPE index }Q=589. \quad \text{Equation (6)}$$

For $C_1=630$, the OPE index Q is 589, so it can be decided as the same as the case of Equation (1).

$$P=(127.0+77.0)/78.0=2.6153.\text{ The OPE index }Q=615. \quad \text{Equation (7)}$$

For $C_1=660$, the OPE index Q is 615, so it can be decided as the same as the case of Equation (1).

$$P=(125.0+77.0)/78.0=2.5897.\text{ The OPE index }Q=589. \quad \text{Equation (8)}$$

For $C_1=650$, the OPE index Q is 589, so it can be decided as the same as the case of Equation (1).

$$P=(111.0+79.0)/78.0=2.4358.\text{ The OPE index }Q=435. \quad \text{Equation (9)}$$

For $C_1=490$, the OPE index Q is 435, so it can be decided as the same as the case of Equation (1).

$$P=(125.0+79.0)/78.0=2.6153.\text{ The OPE index }Q=615. \quad \text{Equation (10)}$$

For $C_1=645$, the OPE index Q is 615, so it can be decided as the same as the case of Equation (1).

$$P=(127.0+79.0)/78.0=2.6410.\text{ The OPE index }Q=641. \quad \text{Equation (11)}$$

For $C_1=675$, the OPE index Q is 641, so it can be decided as the same as the case of Equation (1).

$$P=(125.0+79.0)/78.0=2.6153.\text{ The OPE index }Q=615. \quad \text{Equation (12)}$$

For $C_1=665$, the OPE index Q is 615, so it can be decided as the same as the case of Equation (1).

$$P=(111.0+73.0)/78.0=2.3589.\text{ The OPE index }Q=358. \quad \text{Equation (13)}$$

For $C_1=435$, the OPE index Q is 358, so it can be decided as the same as the case of Equation (1).

$$P=(125.0+73.0)/78.0=2.5384.\text{ The OPE index }Q=538. \quad \text{Equation (14)}$$

For $C_1=575$, the OPE index Q is 538, so it can be decided as the same as the case of Equation (1).

$$P=(127.0+73.0)/78.0=2.5641.\text{ The OPE index }Q=564. \quad \text{Equation (15)}$$

For $C_1=610$, the OPE index Q is 564, so it can be decided as the same as the case of Equation (1).

$$P=(125.0+73.0)/78.0=2.5384.\text{ The OPE index }Q=538. \quad \text{Equation (16)}$$

For $C_1=600$, the OPE index Q is 538, so it can be decided as the same as the case of Equation (1).

Example 2

A cephalometric radiogram of a patient 2 was taken. A tracing made based on the cephalometric radiogram is shown in FIG. 5.

Figure 5:
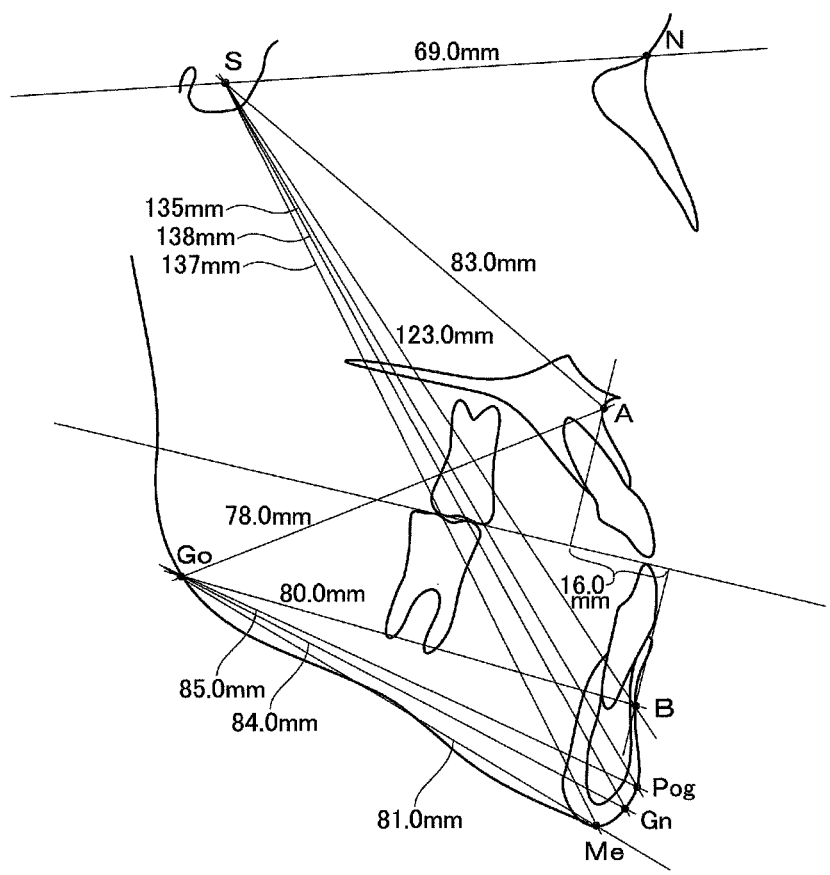
FIG. 5 A tracing made based on a cephalometric radiogram of a patient 2.

From FIG. 5, the distances (S–A), (S–B), (S–Pog), (S–Gn), (S–Me), (Go–B), (Go–Pog), (Go–Gn) and (Go–Me) were measured. Using the data, P was calculated by the Equations (1) to (16). The results are as follows. It is to be noted that (S–N)=69.0 mm and Wits=16.0 mm.

$$P=(123.0+81.0)/83.0=2.4578.\text{ The OPE index }Q=457. \quad \text{Equation (1)}$$

For $C_1=400$, the OPE index Q is 457 and Wits is large as 16.0 mm. Therefore, it can be decided that the patient 2 suffers from dentofacial deformity and in orthodontic treatment, the severing operation on the mandible is necessary.

$$P=(135.0+81.0)/83.0=2.6024.\text{ The OPE index }Q=602. \quad \text{Equation (2)}$$

For $C_1=585$, the OPE index Q is 602 and Wits is large as 16.0 mm, so it can be decided as the same as the case of Equation (1).

$$P=(138.0+81.0)/83.0=2.6385.\text{ The OPE index }Q=638. \quad \text{Equation (3)}$$

For $C_1$=600, the OPE index Q is 638 and Wits is large as 16.0 mm, so it can be decided as the same as the case of Equation (1).

$$P=(137.0+81.0)/83.0=2.6265.\text{ The OPE index }Q=626.\quad\text{Equation (4)}$$

For $C_1$=585, the OPE index Q is 626 and Wits is large as 16.0 mm, so it can be decided as the same as the case of Equation (1).

$$P=(123.0+84.0)/83.0=2.4939.\text{ The OPE index }Q=493.\quad\text{Equation (5)}$$

For $C_1$=475, the OPE index Q is 493 and Wits is large as 16.0 mm, so it can be decided as the same as the case of Equation (1).

$$P=(135.0+84.0)/83.0=2.6385.\text{ The OPE index }Q=638.\quad\text{Equation (6)}$$

For $C_1$=630, the OPE index Q is 638 and Wits is large as 16.0 mm, so it can be decided as the same as the case of Equation (1).

$$P=(138.0+84.0)/83.0=2.6746.\text{ The OPE index }Q=674.\quad\text{Equation (7)}$$

For $C_1$=660, the OPE index Q is 674 and Wits is large as 16.0 mm, so it can be decided as the same as the case of Equation (1).

$$P=(137.0+84.0)/83.0=2.6626.\text{ The OPE index }Q=662.\quad\text{Equation (8)}$$

For $C_1$=650, the OPE index Q is 692 and Wits is large as 16.0 mm, so it can be decided as the same as the case of Equation (1).

$$P=(123.0+85.0)/83.0=2.5060.\text{ The OPE index }Q=506.\quad\text{Equation (9)}$$

For $C_1$=490, the OPE index Q is 506 and Wits is large as 16.0 mm, so it can be decided as the same as the case of Equation (1).

$$P=(135.0+85.0)/83.0=2.6506.\text{ The OPE index }Q=650.\quad\text{Equation (10)}$$

For $C_1$=645, the OPE index Q is 650 and Wits is large as 16.0 mm, so it can be decided as the same as the case of Equation (1).

$$P=(138.0+85.0)/83.0=2.6867.\text{ The OPE index }Q=686.\quad\text{Equation (11)}$$

For $C_1$=675, the OPE index Q is 686 and Wits is large as 16.0 mm, so it can be decided as the same as the case of Equation (1).

$$P=(137.0+85.0)/83.0=2.6746.\text{ The OPE index }Q=674.\quad\text{Equation (12)}$$

For $C_1$=665, the OPE index Q is 674 and Wits is large as 16.0 mm, so it can be decided as the same as the case of Equation (1).

$$P=(123.0+80.0)/83.0=2.4457.\text{ The OPE index }Q=445.\quad\text{Equation (13)}$$

For $C_1$=435, the OPE index Q is 445 and Wits is large as 16.0 mm, so it can be decided as the same as the case of Equation (1).

$$P=(135.0+80.0)/83.0=2.5903.\text{ The OPE index }Q=590.\quad\text{Equation (14)}$$

For $C_1$=575, the OPE index Q is 590 and Wits is large as 16.0 mm, so it can be decided as the same as the case of Equation (1).

$$P=(138.0+80.0)/83.0=2.6265.\text{ The OPE index }Q=626.\quad\text{Equation (15)}$$

For $C_1$=610, the OPE index Q is 626 and Wits is large as 16.0 mm, so it can be decided as the same as the case of Equation (1).

$$P=(137.0+80.0)/83.0=2.6144.\text{ The OPE index }Q=614.\quad\text{Equation (16)}$$

For $C_1$=600, the OPE index Q is 614 and Wits is large as 16.0 mm, so it can be decided as the same as the case of Equation (1).

Therefore, the necessary severing operation on the mandible was performed. After the severing operation, a cephalometric radiogram of the patient 2 was taken. A tracing made based on the cephalometric radiogram is shown in FIG. 6.

Figure 6:
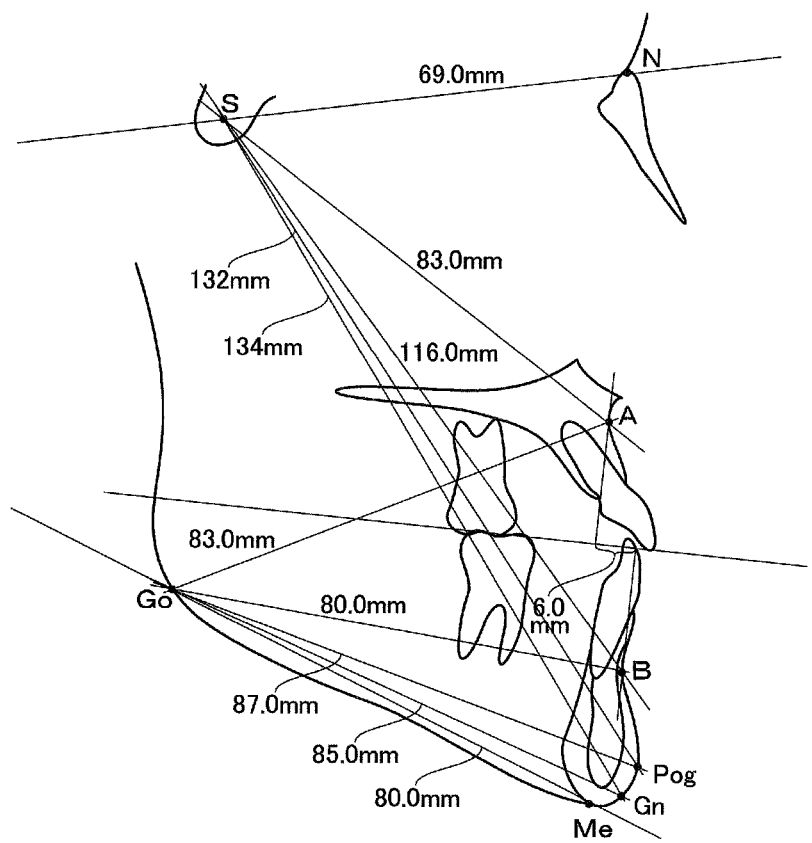
FIG. 6 A tracing made based on a cephalometric radiogram taken after the severing operation on the mandible of the patient 2.

From FIG. 6, the distances (S–A), (S–B), (S–Pog), (S–Gn), (S–Me), (Go–B), (Go–Pog), (Go–Gn) and (Go–Me) were measured. The results are as follows. It is to be noted that (S–N)=69.0 mm and Wits=6.0 mm.

$$P=(116.0+80.0)/83.0=2.3614.\text{ The OPE index }Q=361.\quad\text{Equation (1)}$$

For $C_1$=400, the OPE index Q is 361, so it can be decided that the patient 2 is able to be treated by orthodontic treatment as a result of the severing operation on the mandible.

$$P=(132.0+80.0)/83.0=2.5542.\text{ The OPE index }Q=554.\quad\text{Equation (2)}$$

For $C_1$=585, the OPE index Q is 554, so it can be decided as the same as the case of Equation (1).

$$P=(134.0+80.0)/83.0=2.5783.\text{ The OPE index }Q=578.\quad\text{Equation (3)}$$

For $C_1$=600, the OPE index Q is 578, so it can be decided as the same as the case of Equation (1).

$$P=(133.0+80.0)/83.0=2.5662.\text{ The OPE index }Q=566.\quad\text{Equation (4)}$$

For $C_1$=585, the OPE index Q is 566, so it can be decided as the same as the case of Equation (1).

$$P=(116.0+85.0)/83.0=2.4216.\text{ The OPE index }Q=421.\quad\text{Equation (5)}$$

For $C_1$=475, the OPE index Q is 421, so it can be decided as the same as the case of Equation (1).

$$P=(132.0+85.0)/83.0=2.6144.\text{ The OPE index }Q=614.\quad\text{Equation (6)}$$

For $C_1$=630, the OPE index Q is 614, so it can be decided as the same as the case of Equation (1).

$$P=(134.0+85.0)/83.0=2.6385.\text{ The OPE index }Q=638.\quad\text{Equation (7)}$$

For $C_1$=660, the OPE index Q is 638, so it can be decided as the same as the case of Equation (1).

$$P=(133.0+85.0)/83.0=2.6265.\text{ The OPE index }Q=626.\quad\text{Equation (8)}$$

For $C_1$=650, the OPE index Q is 626, so it can be decided as the same as the case of Equation (1)

$$P=(116.0+87.0)/83.0=2.4457.\text{ The OPE index }Q=445.\quad\text{Equation (9)}$$

For $C_1$=490, the OPE index Q is 445, so it can be decided as the same as the case of Equation (1).

$$P=(132.0+87.0)/83.0=2.6385.\text{ The OPE index }Q=638.\quad\text{Equation (10)}$$

For $C_1$=645, the OPE index Q is 638, so it can be decided as the same as the case of Equation (1).

$$P=(134.0+87.0)/83.0=2.6626.\text{ The OPE index }Q=662.\quad\text{Equation (11)}$$

For $C_1$=675, the OPE index Q is 662, so it can be decided as the same as the case of Equation (1).

$$P=(133.0+87.0)/83.0=2.6506.\text{ The OPE index }Q=650.\quad\text{Equation (12)}$$

For $C_1$=665, the OPE index Q is 650, so it can be decided as the same as the case of Equation (1).

$$P=(116.0+80.0)/83.0=2.3614.\text{ The OPE index }Q=361.\quad\text{Equation (13)}$$

For $C_1$=435, the OPE index Q is 361, so it can be decided as the same as the case of Equation (1).

$$P=(132.0+80.0)/83.0=2.5542.\text{ The OPE index }Q=554.\quad\text{Equation (14)}$$

For $C_1$=575, the OPE index Q is 554, so it can be decided as the same as the case of Equation (1).

$$P=(134.0+80.0)/83.0=2.5783.\text{ The OPE index }Q=578.\quad\text{Equation (15)}$$

For $C_1$=610, the OPE index Q is 578, so it can be decided as the same as the case of Equation (1)

$$P=(133.0+80.0)/83.0=2.5662.\text{ The OPE index }Q=566.\quad\text{Equation (16)}$$

For $C_1=600$, the OPE index Q is 566, so it can be decided as the same as the case of Equation (1)

Example 3

A cephalometric radiogram of a patient 3 was taken. A tracing made based on the cephalometric radiogram is shown in FIG. 7.

Figure 7:
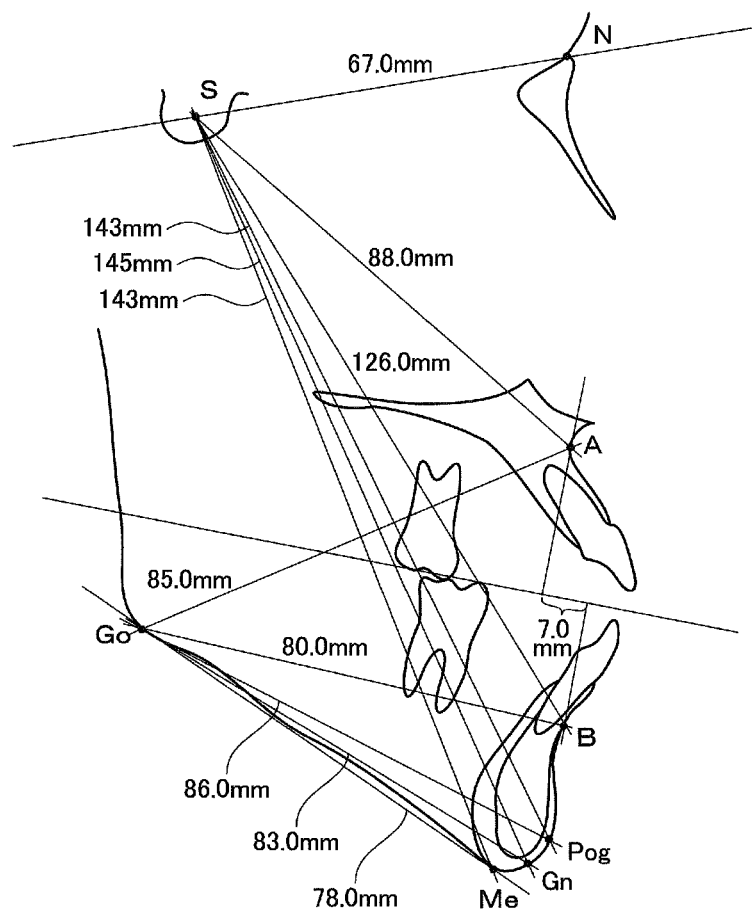
FIG. 7 A tracing made based on a cephalometric radiogram of a patient 3.

From FIG. 7, the distances (S–A), (S–B), (S–Pog), (S–Gn), (S–Me), (Go–B), (Go–Pog), (Go–Gn) and (Go–Me) were measured. Using the data, P was calculated by the Equations (1) to (16). The results are as follows. It is to be noted that (S–N)=67.0 mm and Wits=7.0 mm.

$$P=(126.0+78.0)/88.0=2.3181. \text{ The OPE index } Q=318. \quad \text{Equation (1)}$$

This is a case of light skeletal Class III. However, for $C_1=400$, the OPE index Q is 318, so it can be decided that the patient 3 does not need the surgical operation on the jaw in orthodontic treatment.

$$P=(143.0+78.0)/88.0=2.5113. \text{ The OPE index } Q=511. \quad \text{Equation (2)}$$

This is a case of light skeletal Class III. However, for $C_1=585$, the OPE index Q is 511, so it can be decided as the same as the case of Equation (1).

$$P=(145.0+78.0)/88.0=2.5340. \text{ The OPE index } Q=534. \quad \text{Equation (3)}$$

This is a case of light skeletal Class III. However, for $C_1=600$, the OPE index Q is 534, so it can be decided as the same as the case of Equation (1).

$$P=(143.0+78.0)/88.0=2.5113. \text{ The OPE index } Q=511. \quad \text{Equation (4)}$$

This is a case of light skeletal Class III. However, for $C_1=585$, the OPE index Q is 511, so it can be decided as the same as the case of Equation (1).

$$P=(126.0+83.0)/88.0=2.3750. \text{ The OPE index } Q=375. \quad \text{Equation (5)}$$

This is a case of light skeletal Class III. However, for $C_1=475$, the OPE index Q is 375, so it can be decided as the same as the case of Equation (1).

$$P=(143.0+83.0)/88.0=2.5681. \text{ The OPE index } Q=568. \quad \text{Equation (6)}$$

This is a case of light skeletal Class III. However, for $C_1=630$, the OPE index Q is 568, so it can be decided as the same as the case of Equation (1).

$$P=(145.0+83.0)/88.0=2.5909. \text{ The OPE index } Q=590. \quad \text{Equation (7)}$$

This is a case of light skeletal Class III. However, for $C_1=660$, the OPE index Q is 590, so it can be decided as the same as the case of Equation (1).

$$P=(143.0+83.0)/88.0=2.5681. \text{ The OPE index } Q=568. \quad \text{Equation (8)}$$

This is a case of light skeletal Class III. However, for $C_1=650$, the OPE index Q is 568, so it can be decided as the same as the case of Equation (1).

$$P=(126.0+86.0)/88.0=2.4090. \text{ The OPE index } Q=409. \quad \text{Equation (9)}$$

This is a case of light skeletal Class III. However, for $C_1=490$, the OPE index Q is 409, so it can be decided as the same as the case of Equation (1).

$$P=(143.0+86.0)/88.0=2.6022. \text{ The OPE index } Q=602. \quad \text{Equation (10)}$$

This is a case of light skeletal Class III. However, for $C_1=645$, the OPE index Q is 602, so it can be decided as the same as the case of Equation (1).

$$P=(145.0+86.0)/88.0=2.6250. \text{ The OPE index } Q=625. \quad \text{Equation (11)}$$

This is a case of light skeletal Class III. However, for $C_1=675$, the OPE index Q is 625, so it can be decided as the same as the case of Equation (1).

$$P=(143.0+86.0)/88.0=2.6022. \text{ The OPE index } Q=602. \quad \text{Equation (12)}$$

This is a case of light skeletal Class III. However, for $C_1=665$, the OPE index Q is 602, so it can be decided as the same as the case of Equation (1).

$$P=(126.0+80.0)/88.0=2.3409. \text{ The OPE index } Q=340. \quad \text{Equation (13)}$$

This is a case of light skeletal Class III. However, for $C_1=435$, the OPE index Q is 340, so it can be decided as the same as the case of Equation (1).

$$P=(143.0+80.0)/88.0=2.5340. \text{ The OPE index } Q=534. \quad \text{Equation (14)}$$

This is a case of light skeletal Class III. However, for $C_1=575$, the OPE index Q is 534, so it can be decided as the same as the case of Equation (1).

$$P=(145.0+80.0)/88.0=2.5568. \text{ The OPE index } Q=556. \quad \text{Equation (15)}$$

This is a case of light skeletal Class III. However, for $C_1=610$, the OPE index Q is 556, so it can be decided as the same as the case of Equation (1).

$$P=(143.0+80.0)/88.0=2.5340. \text{ The OPE index } Q=534. \quad \text{Equation (16)}$$

This is a case of light skeletal Class III. However, for $C_1=600$, the OPE index Q is 534, so it can be decided as the same as the case of Equation (1).

Example 4

A cephalometric radiogram of a patient 4 was taken. A tracing made based on the cephalometric radiogram is shown in FIG. 8.

Figure 8:
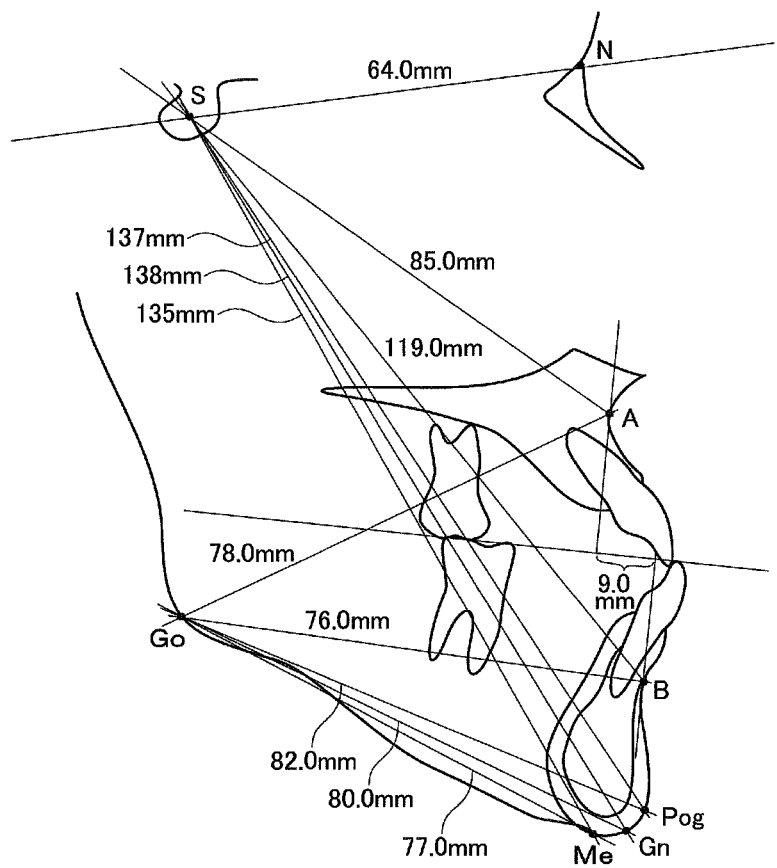
FIG. 8 A tracing made based on a cephalometric radiogram of a patient 4.

From FIG. 8, the distances (S–A), (S–B), (S–Pog), (S–Gn), (S–Me), (Go–B), (Go–Pog), (Go–Gn) and (Go–Me) were measured. Using the data, P was calculated by the Equations (1) to (16). The results are as follows. It is to be noted that (S–N)=64.0 mm and Wits=9.0 mm.

$$P=(119.0+77.0)/85.0=2.3058. \text{ The OPE index } Q=305. \quad \text{Equation (1)}$$

This is a case of skeletal Class III. However, for $C_1=400$, the OPE index Q is 305, so it can be decided that the patient 4 does not need the surgical operation on the jaw in orthodontic treatment.

$$P=(137.0+77.0)/85.0=2.5176. \text{ The OPE index } Q=517. \quad \text{Equation (2)}$$

This is a case of skeletal Class III. However, for $C_1=585$, the OPE index Q is 517, so it can be decided as the same as the case of Equation (1).

$$P=(138.0+77.0)/85.0=2.5294. \text{ The OPE index } Q=529. \quad \text{Equation (3)}$$

This is a case of skeletal Class III. However, for $C_1=600$, the OPE index Q is 529, so it can be decided as the same as the case of Equation (1).

$$P=(135.0+77.0)/85.0=2.4941. \text{ The OPE index } Q=494. \quad \text{Equation (4)}$$

This is a case of skeletal Class III. However, for $C_1=585$, the OPE index Q is 494, so it can be decided as the same as the case of Equation (1).

$$P=(119.0+80.0)/85.0=2.3411. \text{ The OPE index } Q=341. \quad \text{Equation (5)}$$

This is a case of skeletal Class III. However, for $C_1=475$, the OPE index Q is 341, so it can be decided as the same as the case of Equation (1).

$$P=(137.0+80.0)/85.0=2.5529. \text{ The OPE index } Q=552. \quad \text{Equation (6)}$$

This is a case of skeletal Class III. However, for $C_1=630$, the OPE index Q is 552, so it can be decided as the same as the case of Equation (1).

$$P=(138.0+80.0)/85.0=2.5647. \text{ The OPE index } Q=564. \quad \text{Equation (7)}$$

This is a case of skeletal Class III. However, for $C_1=660$, the OPE index Q is 564, so it can be decided as the same as the case of Equation (1).

$$P=(135.0+80.0)/85.0=2.5294. \text{ The OPE index } Q=529. \quad \text{Equation (8)}$$

This is a case of skeletal Class III. However, for $C_1=650$, the OPE index Q is 529, so it can be decided as the same as the case of Equation (1).

$$P=(119.0+82.0)/85.0=2.3647. \text{ The OPE index } Q=364. \quad \text{Equation (9)}$$

This is a case of skeletal Class III. However, for $C_1=490$, the OPE index Q is 364, so it can be decided as the same as the case of Equation (1).

$$P=(137.0+82.0)/85.0=2.5764. \text{ The OPE index } Q=576. \quad \text{Equation (10)}$$

This is a case of skeletal Class III. However, for $C_1=645$, the OPE index Q is 576, so it can be decided as the same as the case of Equation (1).

$$P=(138.0+82.0)/85.0=2.5882. \text{ The OPE index } Q=588. \quad \text{Equation (11)}$$

This is a case of skeletal Class III. However, for $C_1=675$, the OPE index Q is 588, so it can be decided as the same as the case of Equation (1).

$$P=(135.0+82.0)/85.0=2.5529. \text{ The OPE index } Q=552. \quad \text{Equation (12)}$$

This is a case of skeletal Class III. However, for $C_1=665$, the OPE index Q is 552, so it can be decided as the same as the case of Equation (1).

$$P=(119.0+76.0)/85.0=2.2941. \text{ The OPE index } Q=294. \quad \text{Equation (13)}$$

This is a case of skeletal Class III. However, for $C_1=435$, the OPE index Q is 294, so it can be decided as the same as the case of Equation (1).

$$P=(137.0+76.0)/85.0=2.5058. \text{ The OPE index } Q=505. \quad \text{Equation (14)}$$

This is a case of skeletal Class III. However, for $C_1=575$, the OPE index Q is 505, so it can be decided as the same as the case of Equation (1).

$$P=(138.0+76.0)/85.0=2.5176. \text{ The OPE index } Q=517. \quad \text{Equation (15)}$$

This is a case of skeletal Class III. However, for $C_1=610$, the OPE index Q is 517, so it can be decided as the same as the case of Equation (1).

$$P=(135.0+76.0)/85.0=2.4823. \text{ The OPE index } Q=482. \quad \text{Equation (16)}$$

This is a case of skeletal Class III. However, for $C_1=600$, the OPE index Q is 482, so it can be decided as the same as the case of Equation (1).

Example 5

A cephalometric radiogram of a patient 5 was taken. A tracing made based on the cephalometric radiogram is shown in FIG. 9.

Figure 9:
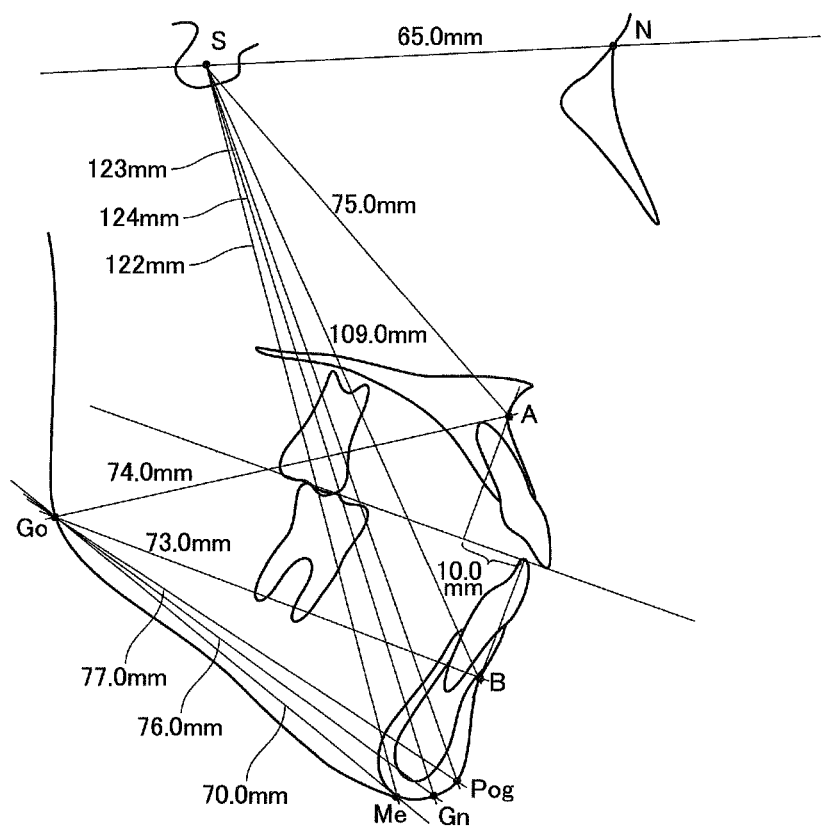
FIG. 9 A tracing made based on a cephalometric radiogram of a patient 5.

From FIG. 9, the distances (S–A), (S–B), (S–Pog), (S–Gn), (S–Me), (Go–B), (Go–Pog), (Go–Gn) and (Go–Me) were measured. Using the data, P was calculated by the Equations (1) to (16). The results are as follows. It is to be noted that (S–N)=65.0 mm and Wits=10.0 mm.

$$P=(109.0+70.0)/75.0=2.3866. \text{ The OPE index } Q=386. \quad \text{Equation (1)}$$

For $C_1=400$, the OPE index Q is 386, so this case is a borderline case. Although the Wits is 10.0 mm and this is quite a strong skeletal case, (S–N)=65.0 mm. Therefore, it can be decided that the surgical operation on the jaw is not necessary in orthodontic treatment.

$$P=(123.0+70.0)/75.0=2.5733. \text{ The OPE index } Q=573. \quad \text{Equation (2)}$$

For $C_1=585$, the OPE index Q is 573, so this case is a borderline case. It can be decided as the same as the case of Equation (1).

$$P=(124.0+70.0)/75.0=2.5866. \text{ The OPE index } Q=586. \quad \text{Equation (3)}$$

For $C_1=600$, the OPE index Q is 586, so this case is a borderline case. It can be decided as the same as the case of Equation (1).

$$P=(122.0+70.0)/75.0=2.5600. \text{ The OPE index } Q=560. \quad \text{Equation (4)}$$

For $C_1=585$, the OPE index Q is 560, so this case is a borderline case. It can be decided as the same as the case of Equation (1).

$$P=(109.0+76.0)/75.0=2.4666. \text{ The OPE index } Q=466. \quad \text{Equation (5)}$$

For $C_1=475$, the OPE index Q is 466, so this case is a borderline case. It can be decided as the same as the case of Equation (1).

$$P=(123.0+76.0)/75.0=2.6533. \text{ The OPE index } Q=653. \quad \text{Equation (6)}$$

For $C_1=630$, the OPE index Q is 653, so this case is a borderline case. It can be decided as the same as the case of Equation (1).

$$P=(124.0+76.0)/75.0=2.6666. \text{ The OPE index } Q=666. \quad \text{Equation (7)}$$

For $C_1=660$, the OPE index Q is 666, so this case is a borderline case. It can be decided as the same as the case of Equation (1).

$$P=(122.0+76.0)/75.0=2.6400. \text{ The OPE index } Q=640. \quad \text{Equation (8)}$$

For $C_1=650$, the OPE index Q is 640, so this case is a borderline case. It can be decided as the same as the case of Equation (1).

$$P=(109.0+77.0)/75.0=2.4800. \text{ The OPE index } Q=480. \quad \text{Equation (9)}$$

For $C_1=490$, the OPE index Q is 480, so this case is a borderline case. It can be decided as the same as the case of Equation (1).

$$P=(123.0+77.0)/75.0=2.6666. \text{ The OPE index } Q=666. \quad \text{Equation (10)}$$

For $C_1=645$, the OPE index Q is 666, so this case is a borderline case. It can be decided as the same as the case of Equation (1).

$$P=(124.0+77.0)/75.0=2.6800. \text{ The OPE index } Q=680. \quad \text{Equation (11)}$$

For $C_1=675$, the OPE index Q is 680, so this case is a borderline case. It can be decided as the same as the case of Equation (1).

$$P=(122.0+77.0)/75.0=2.6533. \text{ The OPE index } Q=653. \quad \text{Equation (12)}$$

For $C_1=665$, the OPE index Q is 653, so this case is a borderline case. It can be decided as the same as the case of Equation (1).

$$P=(109.0+73.0)/75.0=2.4266. \text{ The OPE index } Q=426. \quad \text{Equation (13)}$$

For $C_1=435$, the OPE index Q is 426, so this case is a borderline case. It can be decided as the same as the case of Equation (1).

$$P=(123.0+73.0)/75.0=2.6133. \text{ The OPE index } Q=613. \quad \text{Equation (14)}$$

For $C_1=575$, the OPE index Q is 613, so this case is a borderline case. It can be decided as the same as the case of Equation (1).

$$P=(124.0+73.0)/75.0=2.6266. \text{ The OPE index } Q=626. \quad \text{Equation (15)}$$

For $C_1$=610, the OPE index Q is 626, so this case is a borderline case. It can be decided as the same as the case of Equation (1).

$$P=(122.0+73.0)/75.0=2.6000. \text{ The OPE index } Q=600. \quad \text{Equation (16)}$$

For $C_1$=600, the OPE index Q is 600, so this case is a borderline case. It can be decided as the same as the case of Equation (1).

Example 6

A cephalometric radiogram of a patient 6 was taken. A tracing made based on the cephalometric radiogram is shown in FIG. 10.

Figure 10:
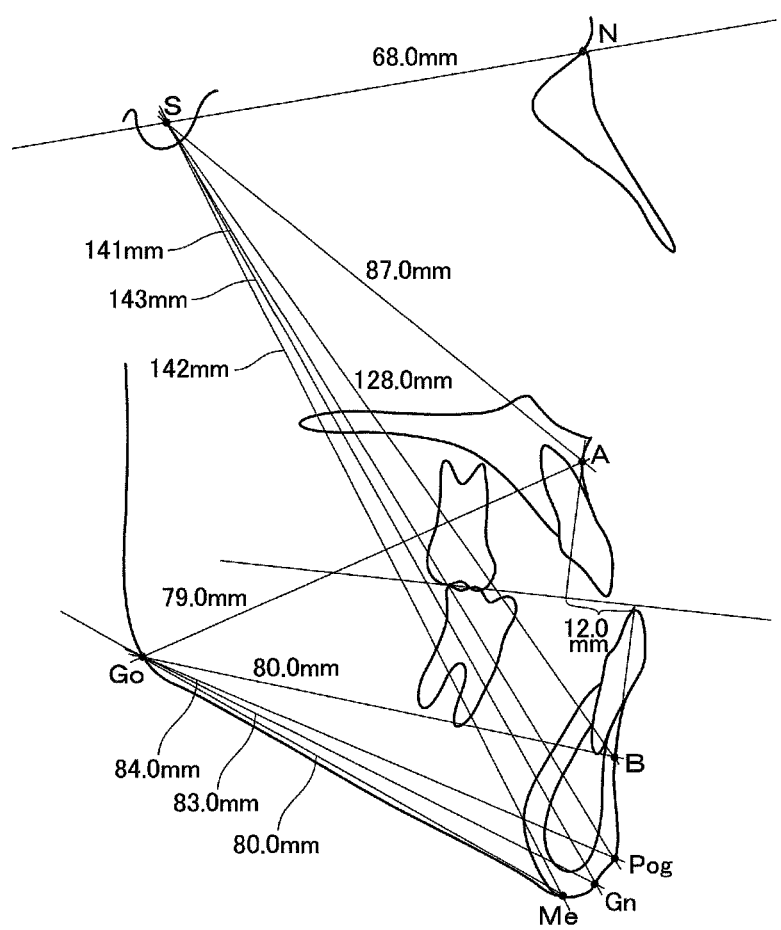
FIG. 10 A tracing made based on a cephalometric radiogram of a patient 6.

From FIG. 10, the distances (S–A), (S–B), (S–Pog), (S–Gn), (S–Me), (Go–B), (Go–Pog), (Go–Gn) and (Go–Me) were measured. Using the data, P was calculated by the Equations (1) to (16). The results are as follows. It is to be noted that (S–N)=68.0 mm and Wits=12.0 mm.

$$P=(128.0+80.0)/87.0=2.3908. \text{ The OPE index } Q=390. \quad \text{Equation (1)}$$

For $C_1$=400, the OPE index Q is 390, so this case is a borderline case. As the Wits is 12.0 mm, which is larger than 10.0 mm and (S–N)=68.0 mm, this case is a case of skeletal Class III. Therefore, it can be decided that the patient 6 suffers from dentofacial deformity and the severing operation on the mandible is necessary.

$$P=(141.0+80.0)/87.0=2.5402. \text{ The OPE index } Q=540. \quad \text{Equation (2)}$$

For $C_1$=585, the OPE index Q is 540, so this case is a borderline case. It can be decided as the same as the case of Equation (1).

$$P=(143.0+80.0)/87.0=2.5632. \text{ The OPE index } Q=563. \quad \text{Equation (3)}$$

For $C_1$=600, the OPE index Q is 563, so this case is a borderline case. It can be decided as the same as the case of Equation (1).

$$P=(142.0+80.0)/87.0=2.5517. \text{ The OPE index } Q=551. \quad \text{Equation (4)}$$

For $C_1$=585, the OPE index Q is 551, so this case is a borderline case. It can be decided as the same as the case of Equation (1).

$$P=(128.0+83.0)/87.0=2.4252. \text{ The OPE index } Q=425. \quad \text{Equation (5)}$$

For $C_1$=475, the OPE index Q is 425, so this case is a borderline case. It can be decided as the same as the case of Equation (1).

$$P=(141.0+83.0)/87.0=2.5747. \text{ The OPE index } Q=574. \quad \text{Equation (6)}$$

For $C_1$=630, the OPE index Q is 574, so this case is a borderline case. It can be decided as the same as the case of Equation (1).

$$P=(143.0+83.0)/87.0=2.5977. \text{ The OPE index } Q=597. \quad \text{Equation (7)}$$

For $C_1$=660, the OPE index Q is 597, so this case is a borderline case. It can be decided as the same as the case of Equation (1).

$$P=(142.0+83.0)/87.0=2.5862. \text{ The OPE index } Q=586. \quad \text{Equation (8)}$$

For $C_1$=650, the OPE index Q is 586, so this case is a borderline case. It can be decided as the same as the case of Equation (1).

$$P=(128.0+84.0)/87.0=2.4367. \text{ The OPE index } Q=436. \quad \text{Equation (9)}$$

For $C_1$=490, the OPE index Q is 436, so this case is a borderline case. It can be decided as the same as the case of Equation (1).

$$P=(141.0+84.0)/87.0=2.5862. \text{ The OPE index } Q=586. \quad \text{Equation (10)}$$

For $C_1$=645, the OPE index Q is 586, so this case is a borderline case. It can be decided as the same as the case of Equation (1).

$$P=(143.0+84.0)/87.0=2.6091. \text{ The OPE index } Q=609. \quad \text{Equation (11)}$$

For $C_1$=675, the OPE index Q is 609, so this case is a borderline case. It can be decided as the same as the case of Equation (1).

$$P=(142.0+84.0)/87.0=2.5977. \text{ The OPE index } Q=597. \quad \text{Equation (12)}$$

For $C_1$=665, the OPE index Q is 597, so this case is a borderline case. It can be decided as the same as the case of Equation (1).

$$P=(128.0+80.0)/87.0=2.3908. \text{ The OPE index } Q=390. \quad \text{Equation (13)}$$

For $C_1$=435, the OPE index Q is 390, so this case is a borderline case. It can be decided as the same as the case of Equation (1).

$$P=(141.0+80.0)/87.0=2.5402. \text{ The OPE index } Q=540. \quad \text{Equation (14)}$$

For $C_1$=575, the OPE index Q is 540, so this case is a borderline case. It can be decided as the same as the case of Equation (1).

$$P=(143.0+80.0)/87.0=2.5632. \text{ The OPE index } Q=563. \quad \text{Equation (15)}$$

For $C_1$=610, the OPE index Q is 563, so this case is a borderline case. It can be decided as the same as the case of Equation (1).

$$P=(142.0+80.0)/87.0=2.5517. \text{ The OPE index } Q=551. \quad \text{Equation (16)}$$

For $C_1$=600, the OPE index Q is 551, so this case is a borderline case. It can be decided as the same as the case of Equation (1).

Therefore, the necessary severing operation on the mandible was performed. After the severing operation, a cephalometric radiogram of the patient 6 was taken. A tracing made based on the cephalometric radiogram is shown in FIG. 11.

Figure 11:
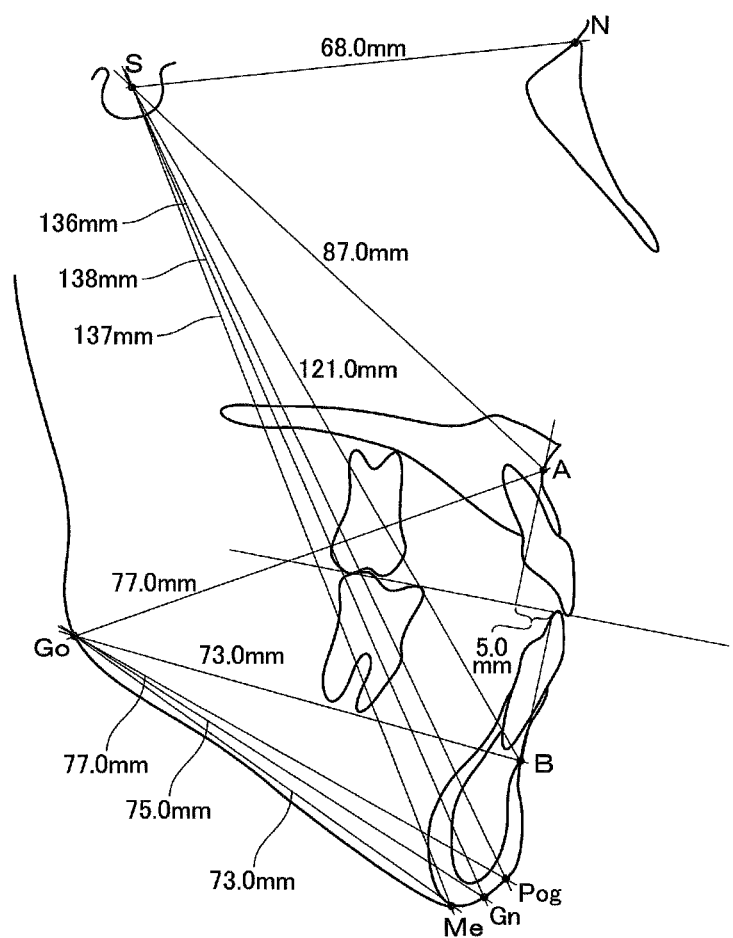
FIG. 11 A tracing made based on a cephalometric radiogram taken after the severing operation on the mandible of the patient 6.

From FIG. 11, the distances (S–A), (S–B), (S–Pog), (S–Gn), (S–Me), (Go–B), (Go–Pog), (Go–Gn) and (Go–Me) were measured. Measured distances are shown in FIG. 11. Using the data, P was calculated by the equations (1) to (16). The results are as follows. It is to be noted that (S–N)=68.0 mm and Wits=5.0 mm.

$$P=(121.0+73.0)/87.0=2.2298. \text{ The OPE index } Q=229. \quad \text{Equation (1)}$$

For $C_1$=400, the OPE index Q is 229, so it can be decided that the patient 6 is able to be treated by orthodontic treatment as a result of the severing operation on the mandible.

$$P=(136.0+73.0)/87.0=2.4022. \text{ The OPE index } Q=402. \quad \text{Equation (2)}$$

For $C_1$=585, the OPE index Q is 402. It can be decided as the same as the case of Equation $$P=(138.0+73.0)/87.0=2.4252. \text{ The OPE index } Q=425. \quad \text{Equation (3)}$$

For $C_1$=600, the OPE index Q is 425. It can be decided as the same as the case of Equation (1).

$$P=(137.0+73.0)/87.0=2.4137. \text{ The OPE index } Q=413. \quad \text{Equation (4)}$$

For $C_1$=585, the OPE index Q is 413. It can be decided as the same as the case of Equation (1).

$$P=(121.0+75.0)/87.0=2.2528. \text{ The OPE index } Q=252. \quad \text{Equation (5)}$$

For $C_1$=475, the OPE index Q is 252. It can be decided as the same as the case of Equation (1).

$$P=(136.0+75.0)/87.0=2.4252. \text{ The OPE index } Q=425. \quad \text{Equation (6)}$$

For $C_1$=630, the OPE index Q is 425. It can be decided as the same as the case of Equation (1).

$$P=(138.0+75.0)/87.0=2.4482. \text{ The OPE index } Q=448. \quad \text{Equation (7)}$$

For $C_1=660$, the OPE index Q is 448. It can be decided as the same as the case of Equation (1).

$$P=(137.0+75.0)/87.0=2.4367. \text{ The OPE index } Q=436. \quad \text{Equation (8)}$$

For $C_1=650$, the OPE index Q is 436. It can be decided as the same as the case of Equation (1).

$$P=(121.0+77.0)/87.0=2.2758. \text{ The OPE index } Q=275. \quad \text{Equation (9)}$$

For $C_1=490$, the OPE index Q is 275. It can be decided as the same as the case of Equation (1).

$$P=(136.0+77.0)/87.0=2.4482. \text{ The OPE index } Q=448. \quad \text{Equation (10)}$$

For $C_1=645$, the OPE index Q is 448. It can be decided as the same as the case of Equation $$P=(138.0+77.0)/87.0=2.4712. \text{ The OPE index } Q=471. \quad \text{Equation (11)}$$

For $C_1=675$, the OPE index Q is 471. It can be decided as the same as the case of Equation (1).

$$P=(137.0+77.0)/87.0=2.4597. \text{ The OPE index } Q=459. \quad \text{Equation (12)}$$

For $C_1=665$, the OPE index Q is 459. It can be decided as the same as the case of Equation (1).

$$P=(121.0+73.0)/87.0=2.2298. \text{ The OPE index } Q=229. \quad \text{Equation (13)}$$

For $C_1=435$, the OPE index Q is 229. It can be decided as the same as the case of Equation (1).

$$P=(136.0+73.0)/87.0=2.4022. \text{ The OPE index } Q=402. \quad \text{Equation (14)}$$

For $C_1=575$, the OPE index Q is 402. It can be decided as the same as the case of Equation (1).

$$P=(138.0+73.0)/87.0=2.4252. \text{ The OPE index } Q=425. \quad \text{Equation (15)}$$

For $C_1=610$, the OPE index Q is 425. It can be decided as the same as the case of Equation (1).

$$P=(137.0+73.0)/87.0=2.4137. \text{ The OPE index } Q=413. \quad \text{Equation (16)}$$

For $C_1=600$, the OPE index Q is 413. It can be decided as the same as the case of Equation (1).

Example 7

A cephalometric radiogram of a patient 7 was taken. A tracing made based on the cephalometric radiogram is shown in FIG. 12.

Figure 12:
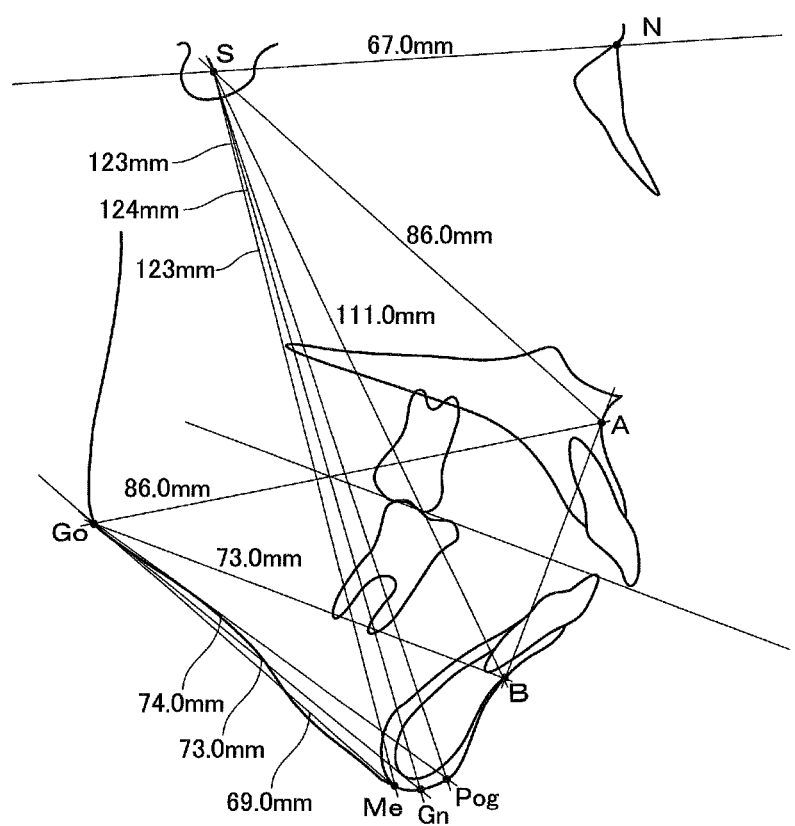
FIG. 12 A tracing made based on a cephalometric radiogram of a patient 7.

From FIG. 12, the distances (S–A), (S–B), (S–Pog), (S–Gn), (S–Me), (Go–B), (Go–Pog), (Go–Gn) and (Go–Me) were measured. The measured distances are shown in FIG. 12. Using the data, P was calculated by the Equations (1) to (16). The results are as follows. It is to be noted that (S–N)=67.0 mm and Wits=0 mm.

$$P=(111.0+69.0)/86.0=2.0930. \text{ The OPE index } Q=93. \quad \text{Equation (1)}$$

For $C_1=400$, the OPE index Q is 93, indicating withdrawing tendency of the mandible. However, it can be decided that the patient 7 does not need the surgical operation on the jaw in orthodontic treatment and orthodontic treatment with a tooth extraction can be adapted.

$$P=(123.0+69.0)/86.0=2.2325. \text{ The OPE index } Q=232. \quad \text{Equation (2)}$$

For $C_1=585$, the OPE index Q is 232, indicating withdrawing tendency of the mandible. However, it can be decided as the same as the case of Equation (1).

$$P=(124.0+69.0)/86.0=2.2441. \text{ The OPE index } Q=244. \quad \text{Equation (3)}$$

For $C_1=600$, the OPE index Q is 244, indicating withdrawing tendency of the mandible. However, it can be decided as the same as the case of Equation (1).

$$P=(123.0+69.0)/86.0=2.2325. \text{ The OPE index } Q=232. \quad \text{Equation (4)}$$

For $C_1=585$, the OPE index Q is 232, indicating withdrawing tendency of the mandible. However, it can be decided as the same as the case of Equation (1).

$$P=(111.0+73.0)/86.0=2.1395. \text{ The OPE index } Q=139. \quad \text{Equation (5)}$$

For $C_1=475$, the OPE index Q is 139, indicating withdrawing tendency of the mandible. However, it can be decided as the same as the case of Equation (1).

$$P=(123.0+73.0)/86.0=2.2790. \text{ The OPE index } Q=279. \quad \text{Equation (6)}$$

For $C_1=630$, the OPE index Q is 279, indicating withdrawing tendency of the mandible. However, it can be decided as the same as the case of Equation (1).

$$P=(124.0+73.0)/86.0=2.2906. \text{ The OPE index } Q=290. \quad \text{Equation (7)}$$

For $C_1=660$, the OPE index Q is 290, indicating withdrawing tendency of the mandible. However, it can be decided as the same as the case of Equation (1).

$$P=(123.0+73.0)/86.0=2.2790. \text{ The OPE index } Q=279. \quad \text{Equation (8)}$$

For $C_1=650$, the OPE index Q is 279, indicating withdrawing tendency of the mandible. However, it can be decided as the same as the case of Equation (1).

$$P=(111.0+74.0)/86.0=2.1511. \text{ The OPE index } Q=151. \quad \text{Equation (9)}$$

For $C_1=490$, the OPE index Q is 151, indicating withdrawing tendency of the mandible. However, it can be decided as the same as the case of Equation (1).

$$P=(123.0+74.0)/86.0=2.2906. \text{ The OPE index } Q=290. \quad \text{Equation (10)}$$

For $C_1=645$, the OPE index Q is 290, indicating withdrawing tendency of the mandible. However, it can be decided as the same as the case of Equation (1).

$$P=(124.0+74.0)/86.0=2.3023. \text{ The OPE index } Q=302. \quad \text{Equation (11)}$$

For $C_1=675$, the OPE index Q is 302, indicating withdrawing tendency of the mandible. However, it can be decided as the same as the case of Equation (1).

$$P=(123.0+74.0)/86.0=2.2906. \text{ The OPE index } Q=290. \quad \text{Equation (12)}$$

For $C_1=665$, the OPE index Q is 290, indicating withdrawing tendency of the mandible. However, it can be decided as the same as the case of Equation (1).

$$P=(111.0+73.0)/86.0=2.1395. \text{ The OPE index } Q=139. \quad \text{Equation (13)}$$

For $C_1=435$, the OPE index Q is 139, indicating withdrawing tendency of the mandible. However, it can be decided as the same as the case of Equation (1).

$$P=(123.0+73.0)/86.0=2.2790. \text{ The OPE index } Q=279. \quad \text{Equation (14)}$$

For $C_1=575$, the OPE index Q is 279, indicating withdrawing tendency of the mandible. However, it can be decided as the same as the case of Equation (1).

$$P=(124.0+73.0)/86.0=2.2906. \text{ The OPE index } Q=290. \quad \text{Equation (15)}$$

For $C_1=610$, the OPE index Q is 290, indicating withdrawing tendency of the mandible. However, it can be decided as the same as the case of Equation (1).

$$P=(123.0+73.0)/86.0=2.2790. \text{ The OPE index } Q=279. \quad \text{Equation (16)}$$

For $C_1=600$, the OPE index Q is 279, indicating withdrawing tendency of the mandible. However, it can be decided as the same as the case of Equation (1).

Example 8

A cephalometric radiogram of a patient 8 was taken. A tracing made based on the cephalometric radiogram is shown in FIG. 13.

Figure 13:
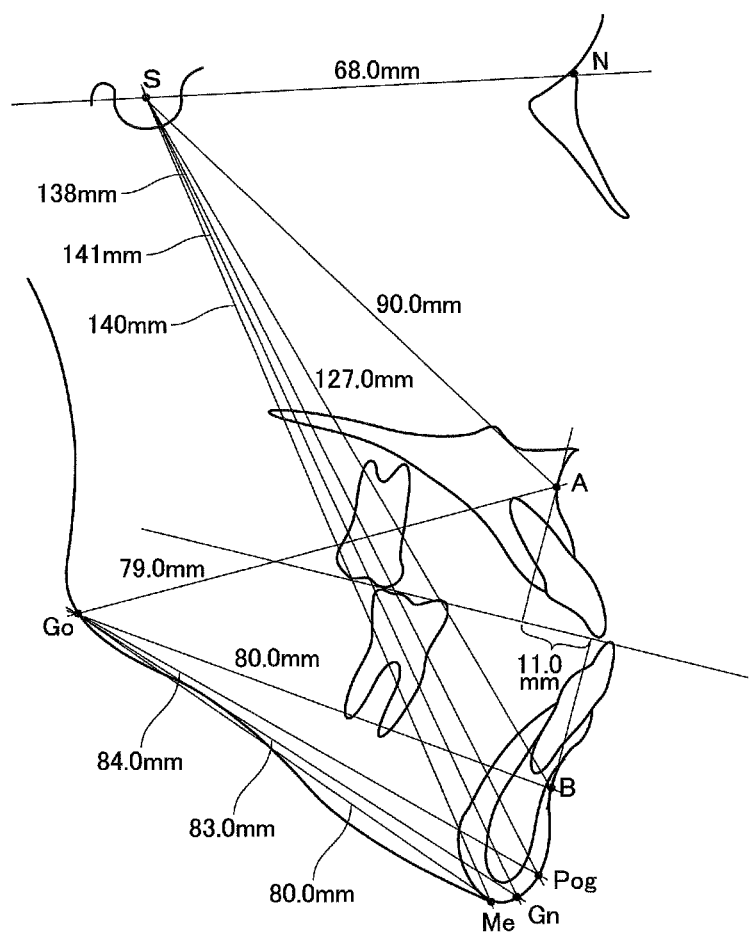
FIG. 13 A tracing made based on a cephalometric radiogram of a patient 8.

From FIG. 13, the distances (S–A), (S–B), (S–Pog), (S–Gn), (S–Me), (Go–B), (Go–Pog), (Go–Gn) and (Go–Me) were measured. The measured distances are shown in FIG. 13. Using the data, P was calculated by the Equations (1) to (16). The results are as follows. It is to be noted that (S–N)=68.0 mm and Wits=11.0 mm.

$P=(127.0+80.0)/90.0=2.3000$. The OPE index $Q=300$.  Equation (1)

For $C_1=400$, the OPE index Q is 300. It can be decided that the patient 8 does not need the surgical operation on the jaw in orthodontic treatment.

$P=(138.0+80.0)/90.0=2.4222$. The OPE index $Q=422$.  Equation (2)

For $C_1=585$, the OPE index Q is 422. It can be decided as the same as the case of Equation (1).

$P=(141.0+80.0)/90.0=2.4555$. The OPE index $Q=455$.  Equation (3)

For $C_1=600$, the OPE index Q is 455. It can be decided as the same as the case of Equation (1).

$P=(140.0+80.0)/90.0=2.4444$. The OPE index $Q=444$.  Equation (4)

For $C_1=585$, the OPE index Q is 444. It can be decided as the same as the case of Equation (1).

$P=(127.0+83.0)/90.0=2.3333$. The OPE index $Q=333$.  Equation (5)

For $C_1=475$, the OPE index Q is 333. It can be decided as the same as the case of Equation (1).

$P=(138.0+83.0)/90.0=2.4555$. The OPE index $Q=455$.  Equation (6)

For $C_1=630$, the OPE index Q is 455. It can be decided as the same as the case of Equation (1).

$P=(141.0+83.0)/90.0=2.4888$. The OPE index $Q=488$.  Equation (7)

For $C_1=660$, the OPE index Q is 488. It can be decided as the same as the case of Equation (1).

$P=(140.0+83.0)/90.0=2.4777$. The OPE index $Q=477$.  Equation (8)

For $C_1=650$, the OPE index Q is 477. It can be decided as the same as the case of Equation (1).

$P=(127.0+84.0)/90.0=2.3444$. The OPE index $Q=344$.  Equation (9)

For $C_1=490$, the OPE index Q is 344. It can be decided as the same as the case of Equation (1).

$P=(138.0+84.0)/90.0=2.4666$. The OPE index $Q=466$.  Equation (10)

For $C_1=645$, the OPE index Q is 466. It can be decided as the same as the case of Equation (1).

$P=(141.0+84.0)/90.0=2.5000$. The OPE index $Q=500$.  Equation (11)

For $C_1=675$, the OPE index Q is 500. It can be decided as the same as the case of Equation (1).

$P=(140.0+84.0)/90.0=2.4888$. The OPE index $Q=488$.  Equation (12)

For $C_1=665$, the OPE index Q is 488. It can be decided as the same as the case of Equation (1).

$P=(127.0+80.0)/90.0=2.3000$. The OPE index $Q=300$.  Equation (13)

For $C_1=435$, the OPE index Q is 300. It can be decided as the same as the case of Equation (1).

$P=(138.0+80.0)/90.0=2.4222$. The OPE index $Q=422$.  Equation (14)

For $C_1=575$, the OPE index Q is 422. It can be decided as the same as the case of Equation (1).

$P=(141.0+80.0)/90.0=2.4555$. The OPE index $Q=455$.  Equation (15)

For $C_1=610$, the OPE index Q is 455. It can be decided as the same as the case of Equation (1).

$P=(140.0+80.0)/90.0=2.4444$. The OPE index $Q=444$.  Equation (16)

For $C_1=600$, the OPE index Q is 444. It can be decided as the same as the case of Equation (1).

Example 9

A cephalometric radiogram of a patient 9 was taken. A tracing made based on the cephalometric radiogram is shown in FIG. 14.

Figure 14:
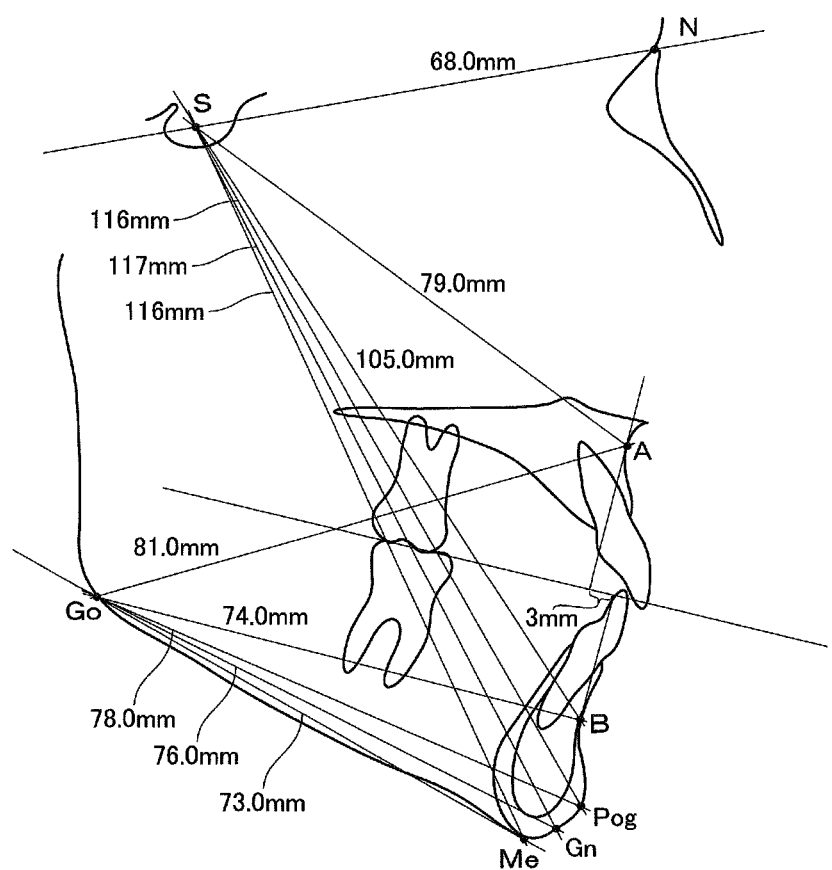
FIG. 14 A tracing made based on a cephalometric radiogram of a patient 9.

From FIG. 14, the distances (S–A), (S–B), (S–Pog), (S–Gn), (S–Me), (Go–B), (Go–Pog), (Go–Gn) and (Go–Me) were measured. The measured distances are shown in FIG. 14. Using the data, P was calculated by the Equations (1) to (16). The results are as follows. It is to be noted that (S–N)=68.0 mm and Wits=3.0 mm.

$P=(105.0+73.0)/79.0=2.2531$. The OPE index $Q=253$.  Equation (1)

For $C_1=400$, the OPE index Q is 253. It can be decided that the patient 9 does not need the surgical operation on the jaw in orthodontic treatment.

$P=(116.0+73.0)/79.0=2.3924$. The OPE index $Q=392$.  Equation (2)

For $C_1=585$, the OPE index Q is 392. It can be decided as the same as the case of Equation (1).

$P=(117.0+73.0)/79.0=2.4050$. The OPE index $Q=405$.  Equation (3)

For $C_1=600$, the OPE index Q is 405. It can be decided as the same as the case of Equation (1).

$P=(116.0+73.0)/79.0=2.3924$. The OPE index $Q=392$.  Equation (4)

For $C_1=585$, the OPE index Q is 392. It can be decided as the same as the case of Equation (1).

$P=(105.0+76.0)/79.0=2.2911$. The OPE index $Q=291$.  Equation (5)

For $C_1=475$, the OPE index Q is 291. It can be decided as the same as the case of Equation (1).

$P=(116.0+76.0)/79.0=2.4303$. The OPE index $Q=430$.  Equation (6)

For $C_1=630$, the OPE index Q is 430. It can be decided as the same as the case of Equation (1).

$P=(117.0+76.0)/79.0=2.4430$. The OPE index $Q=443$.  Equation (7)

For $C_1=660$, the OPE index Q is 443. It can be decided as the same as the case of Equation (1).

$P=(116.0+76.0)/79.0=2.4303$. The OPE index $Q=430$.  Equation (8)

For $C_1=650$, the OPE index Q is 430. It can be decided as the same as the case of Equation (1).

$P=(105.0+78.0)/79.0=2.3164$. The OPE index $Q=316$.  Equation (9)

For $C_1=490$, the OPE index Q is 316. It can be decided as the same as the case of Equation (1).

$P=(116.0+78.0)/79.0=2.4556$. The OPE index $Q=455$.  Equation (10)

For $C_1=645$, the OPE index Q is 455. It can be decided as the same as the case of Equation (1).

$P=(117.0+78.0)/79.0=2.4683$. The OPE index $Q=468$.  Equation (11)

For $C_1=675$, the OPE index Q is 468. It can be decided as the same as the case of Equation (1).

$P=(116.0+78.0)/79.0=2.4556$. The OPE index $Q=455$.  Equation (12)

For $C_1=665$, the OPE index Q is 455. It can be decided as the same as the case of Equation (1).

$P=(105.0+74.0)/79.0=2.2658$. The OPE index $Q=265$.  Equation (13)

For $C_1=435$, the OPE index Q is 265. It can be decided as the same as the case of Equation (1).

$P=(116.0+74.0)/79.0=2.4050$. The OPE index $Q=405$.  Equation (14)

For $C_1=575$, the OPE index Q is 405. It can be decided as the same as the case of Equation (1).

$$P=(117.0+74.0)/79.0=2.4177. \text{ The OPE index } Q=417. \quad \text{Equation (15)}$$

For $C_1=610$, the OPE index Q is 417. It can be decided as the same as the case of Equation (1).

$$P=(116.0+74.0)/79.0=2.4050. \text{ The OPE index } Q=405. \quad \text{Equation (16)}$$

For $C_1=600$, the OPE index Q is 405. It can be decided as the same as the case of Equation (1).

Example 10

A cephalometric radiogram of a patient 10 was taken. A tracing made based on the cephalometric radiogram is shown in FIG. 15.

Figure 15:
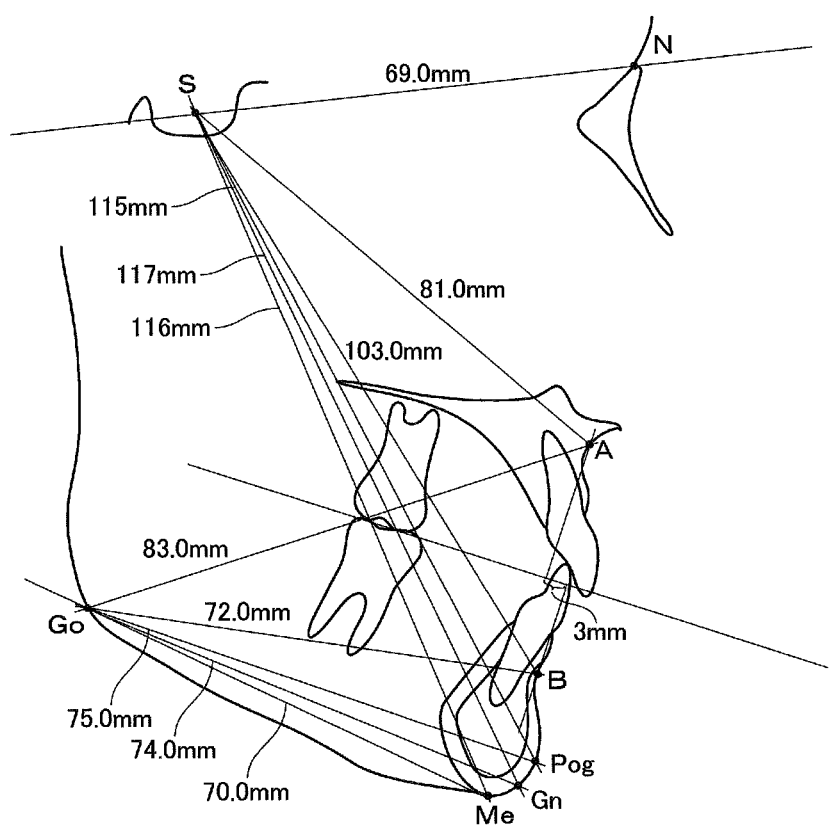
FIG. 15 A tracing made based on a cephalometric radiogram of a patient 10.

From FIG. 15, the distances (S–A), (S–B), (S–Pog), (S–Gn), (S–Me), (Go–B), (Go–Pog), (Go–Gn) and (Go–Me) were measured. The measured distances are shown in FIG. 15. Using the data, P was calculated by the Equations (1) to (16). The results are as follows. It is to be noted that (S–N)=69.0 mm and Wits=3.0 mm.

$$P=(103.0+70.0)/81.0=2.1358. \text{ The OPE index } Q=135. \quad \text{Equation (1)}$$

This case is a non-skeletal case. For $C_1=400$, the OPE index Q is 135. It can be decided that the patient 10 does not need the surgical operation on the jaw in orthodontic treatment and orthodontic treatment with a non-tooth extraction can be adapted.

$$P=(115.0+70.0)/81.0=2.2839. \text{ The OPE index } Q=283. \quad \text{Equation (2)}$$

This case is a non-skeletal case. For $C_1=585$, the OPE index Q is 283. It can be decided as the same as the case of Equation (1).

$$P=(117.0+70.0)/81.0=2.3086. \text{ The OPE index } Q=308. \quad \text{Equation (3)}$$

This case is a non-skeletal case. For $C_1=600$, the OPE index Q is 308. It can be decided as the same as the case of Equation (1).

$$P=(116.0+70.0)/81.0=2.2962. \text{ The OPE index } Q=296. \quad \text{Equation (4)}$$

This case is a non-skeletal case. For $C_1=585$, the OPE index Q is 296. It can be decided as the same as the case of Equation (1).

$$P=(103.0+74.0)/81.0=2.1851. \text{ The OPE index } Q=185. \quad \text{Equation (5)}$$

This case is a non-skeletal case. For $C_1=475$, the OPE index Q is 185. It can be decided as the same as the case of Equation (1).

$$P=(115.0+74.0)/81.0=2.3333. \text{ The OPE index } Q=333. \quad \text{Equation (6)}$$

This case is a non-skeletal case. For $C_1=630$, the OPE index Q is 333. It can be decided as the same as the case of Equation (1).

$$P=(117.0+74.0)/81.0=2.3580. \text{ The OPE index } Q=358. \quad \text{Equation (7)}$$

This case is a non-skeletal case. For $C_1=660$, the OPE index Q is 358. It can be decided as the same as the case of the Equation (1).

$$P=(116.0+74.0)/81.0=2.3456. \text{ The OPE index } Q=345. \quad \text{Equation (8)}$$

This case is a non-skeletal case. For $C_1=650$, the OPE index Q is 345. It can be decided as the same as the case of Equation (1).

$$P=(103.0+75.0)/81.0=2.1975. \text{ The OPE index } Q=197. \quad \text{Equation (9)}$$

This case is a non-skeletal case. For $C_1=490$, the OPE index Q is 197. It can be decided as the same as the case of Equation (1).

$$P=(115.0+75.0)/81.0=2.3456. \text{ The OPE index } Q=345. \quad \text{Equation (10)}$$

This case is a non-skeletal case. For $C_1=645$, the OPE index Q is 345. It can be decided as the same as the case of Equation (1).

$$P=(117.0+75.0)/81.0=2.3703. \text{ The OPE index } Q=370. \quad \text{Equation (11)}$$

This case is a non-skeletal case. For $C_1=675$, the OPE index Q is 370. It can be decided as the same as the case of Equation (1).

$$P=(116.0+75.0)/81.0=2.3580. \text{ The OPE index } Q=358. \quad \text{Equation (12)}$$

This case is a non-skeletal case. For $C_1=665$, the OPE index Q is 358. It can be decided as the same as the case of Equation (1).

$$P=(103.0+72.0)/81.0=2.1604. \text{ The OPE index } Q=160. \quad \text{Equation (13)}$$

This case is a non-skeletal case. For $C_1=435$, the OPE index Q is 160. It can be decided as the same as the case of Equation (1).

$$P=(115.0+72.0)/81.0=2.3086. \text{ The OPE index } Q=308. \quad \text{Equation (14)}$$

This case is a non-skeletal case. For $C_1=575$, the OPE index Q is 308. It can be decided as the same as the case of Equation (1).

$$P=(117.0+72.0)/81.0=2.3333. \text{ The OPE index } Q=333. \quad \text{Equation (15)}$$

This case is a non-skeletal case. For $C_1=610$, the OPE index Q is 333. It can be decided as the same as the case of Equation (1).

$$P=(116.0+72.0)/81.0=2.3209. \text{ The OPE index } Q=320. \quad \text{Equation (16)}$$

This case is a non-skeletal case. For $C_1=600$, the OPE index Q is 320. It can be decided as the same as the case of Equation (1).

Example 11

A cephalometric radiogram of a patient 11 was taken. A tracing made based on the cephalometric radiogram is shown in FIG. 16.

Figure 16:
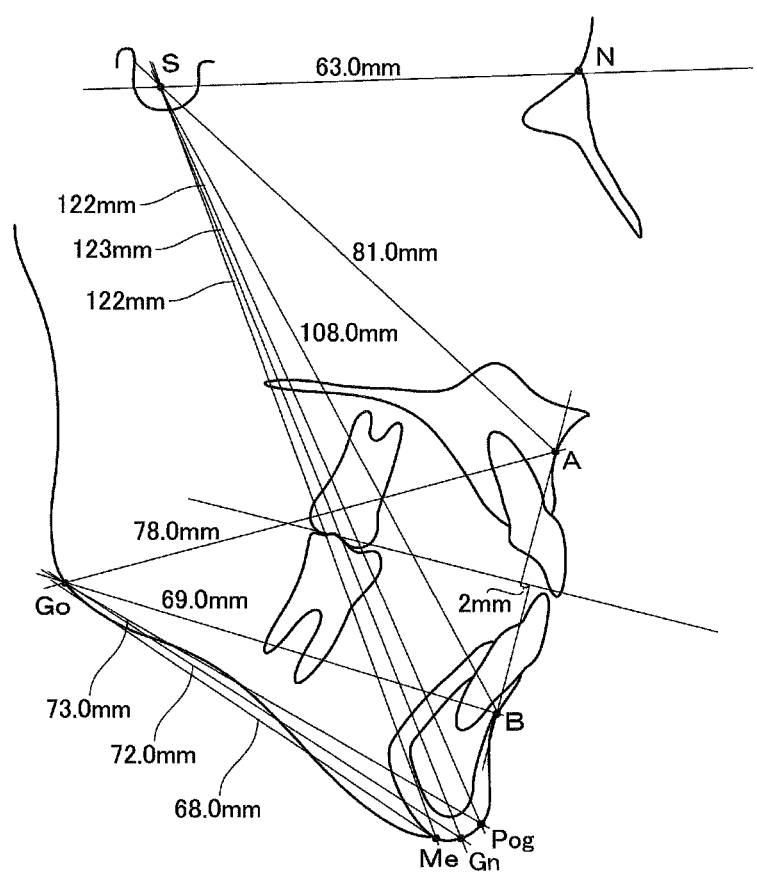
FIG. 16 A tracing made based on a cephalometric radiogram of a patient 11.

From FIG. 16, the distances (S–A), (S–B), (S–Pog), (S–Gn), (S–Me), (Go–B), (Go–Pog), (Go–Gn) and (Go–Me) were measured. The measured distances are shown in FIG. 16. Using the data, P was calculated by the Equations (1) to (16). The results are as follows. It is to be noted that (S–N)=63.0 mm and Wits=2.0 mm.

$$P=(108.0+68.0)/81.0=2.1728. \text{ The OPE index } Q=172. \quad \text{Equation (1)}$$

For $C_1=400$, the OPE index Q is 172 and Wits is 2.0 mm. This case is a non-skeletal case. It can be decided that the patient 11 does not need the surgical operation on the jaw in orthodontic treatment and orthodontic treatment with a non-tooth extraction can be adapted.

$$P=(122.0+68.0)/81.0=2.3456. \text{ The OPE index } Q=345. \quad \text{Equation (2)}$$

For $C_1=585$, the OPE index Q is 345 and Wits is 2.0 mm. This case is a non-skeletal case. It can be decided as the same as the case of Equation (1).

$$P=(123.0+68.0)/81.0=2.3580. \text{ The OPE index } Q=358. \quad \text{Equation (3)}$$

For $C_1=600$, the OPE index Q is 358 and Wits is 2.0 mm. This case is a non-skeletal case. It can be decided as the same as the case of Equation (1).

$$P=(122.0+68.0)/81.0=2.3456. \text{ The OPE index } Q=345. \quad \text{Equation (4)}$$

For $C_1=585$, the OPE index Q is 345 and Wits is 2.0 mm. This case is a non-skeletal case. It can be decided as the same as the case of Equation (1).

$$P=(108.0+72.0)/81.0=2.2222. \text{ The OPE index } Q=222. \quad \text{Equation (5)}$$

For $C_1=475$, the OPE index Q is 222 and Wits is 2.0 mm. This case is a non-skeletal case. It can be decided as the same as the case of Equation (1).

$$P=(122.0+72.0)/81.0=2.3950. \text{ The OPE index } Q=395. \quad \text{Equation (6)}$$

For $C_1=630$, the OPE index Q is 395 and Wits is 2.0 mm. This case is a non-skeletal case. It can be decided as the same as the case of Equation (1).

$$P=(123.0+72.0)/81.0=2.4074. \text{ The OPE index } Q=407. \quad \text{Equation (7)}$$

For $C_1=660$, the OPE index Q is 407 and Wits is 2.0 mm. This case is a non-skeletal case. It can be decided as the same as the case of Equation (1).

$$P=(122.0+72.0)/81.0=2.3950. \text{ The OPE index } Q=395. \quad \text{Equation (8)}$$

For $C_1=650$, the OPE index Q is 395 and Wits is 2.0 mm. This case is a non-skeletal case. It can be decided as the same as the case of Equation (1).

$$P=(108.0+73.0)/81.0=2.2345. \text{ The OPE index } Q=234. \quad \text{Equation (9)}$$

For $C_1=490$, the OPE index Q is 234 and Wits is 2.0 mm. This case is a non-skeletal case. It can be decided as the same as the case of Equation (1).

$$P=(122.0+73.0)/81.0=2.4074. \text{ The OPE index } Q=407. \quad \text{Equation (10)}$$

For $C_1=645$, the OPE index Q is 407 and Wits is 2.0 mm. This case is a non-skeletal case. It can be decided as the same as the case of Equation (1).

$$P=(123.0+73.0)/81.0=2.4197. \text{ The OPE index } Q=419. \quad \text{Equation (11)}$$

For $C_1=675$, the OPE index Q is 419 and Wits is 2.0 mm. This case is a non-skeletal case. It can be decided as the same as the case of Equation (1).

$$P=(122.0+73.0)/81.0=2.4074. \text{ The OPE index } Q=407. \quad \text{Equation (12)}$$

For $C_1=665$, the OPE index Q is 407 and Wits is 2.0 mm. This case is a non-skeletal case. It can be decided as the same as the case of Equation (1).

$$P=(108.0+69.0)/81.0=2.1851. \text{ The OPE index } Q=185. \quad \text{Equation (13)}$$

For $C_1=435$, the OPE index Q is 185 and Wits is 2.0 mm. This case is a non-skeletal case. It can be decided as the same as the case of Equation (1).

$$P=(122.0+69.0)/81.0=2.3580. \text{ The OPE index } Q=358. \quad \text{Equation (14)}$$

For $C_1=575$, the OPE index Q is 358 and Wits is 2.0 mm. This case is a non-skeletal case. It can be decided as the same as the case of Equation (1).

$$P=(123.0+69.0)/81.0=2.3703. \text{ The OPE index } Q=370. \quad \text{Equation (15)}$$

For $C_1=610$, the OPE index Q is 370 and Wits is 2.0 mm. This case is a non-skeletal case. It can be decided as the same as the case of Equation (1).

$$P=(122.0+69.0)/81.0=2.3580. \text{ The OPE index } Q=358. \quad \text{Equation (16)}$$

For $C_1=600$, the OPE index Q is 358 and Wits is 2.0 mm. This case is a non-skeletal case. It can be decided as the same as the case of Equation (1).

Example 12

A cephalometric radiogram of a patient 12 was taken. A tracing made based on the cephalometric radiogram is shown in FIG. 17.

Figure 17:
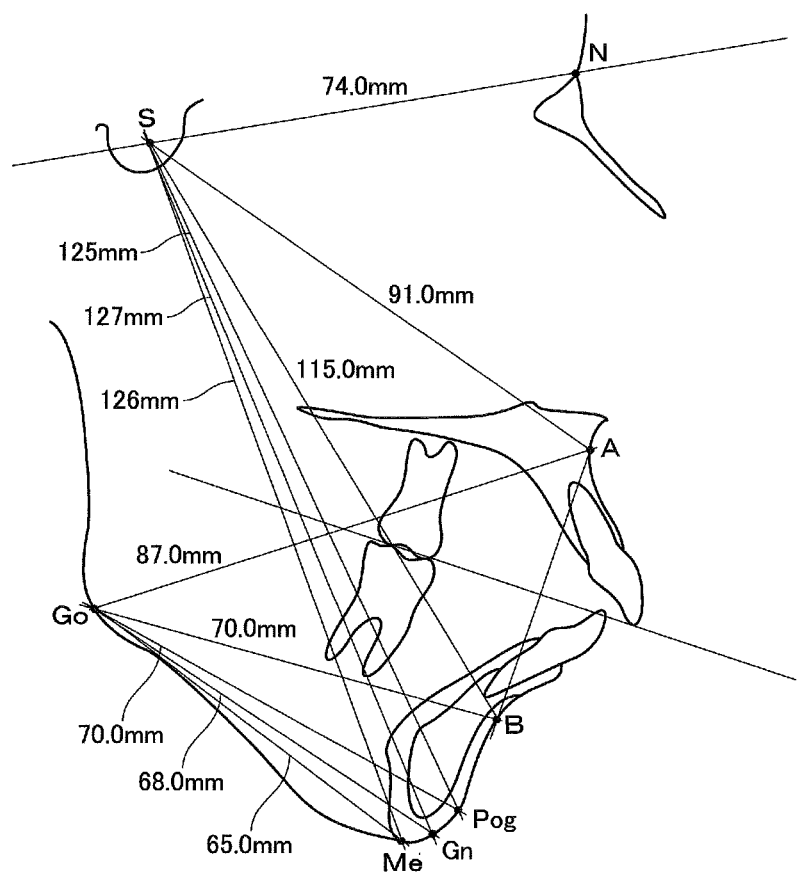
FIG. 17 A tracing made based on a cephalometric radiogram of a patient 12.

From FIG. 17, the distances (S-A), (S-B), (S-Pog), (S-Gn), (S-Me), (Go-B), (Go-Pog), (Go-Gn) and (Go-Me) were measured. The measured distances are shown in FIG. 17. Using the data, P was calculated by the Equations (1) to (16). The results are as follows. It is to be noted that (S-N)=74.0 mm and Wits=0 mm.

$$P=(115.0+65.0)/91.0=1.9780. \text{ The OPE index } Q=-22. \quad \text{Equation (1)}$$

For $C_1=400$, the OPE index Q is -22. Generally, in case of Q<100, the necessity of the surgical operation on the jaw in orthodontic treatment increases. However, this case is a case showing a strong hypogrowth tendency of the mandible. Therefore, it can be decided that the patient 12 does not need the surgical operation on the jaw in orthodontic treatment.

$$P=(125.0+65.0)/91.0=2.0879. \text{ The OPE index } Q=87. \quad \text{Equation (2)}$$

For $C_1=585$, the OPE index Q is 87. Generally, in case of Q<100, the necessity of the surgical operation on the jaw in orthodontic treatment increases. However, this case is a case showing a strong hypogrowth tendency of the mandible. Therefore, it can be decided as the same as the case of Equation (1).

$$P=(127.0+65.0)/91.0=2.1098. \text{ The OPE index } Q=109. \quad \text{Equation (3)}$$

For $C_1=600$, the OPE index Q is 109. Generally, in case of Q<120, the necessity of the surgical operation on the jaw in orthodontic treatment increases. However, this case is a case showing a strong hypogrowth tendency of the mandible. Therefore, it can be decided as the same as the case of Equation (1).

$$P=(126.0+65.0)/91.0=2.0989. \text{ The OPE index } Q=98. \quad \text{Equation (4)}$$

For $C_1=585$, the OPE index Q is 98. Generally, in case of Q<100, the necessity of the surgical operation on the jaw in orthodontic treatment increases. However, this case is a case showing a strong hypogrowth tendency of the mandible. Therefore, it can be decided as the same as the case of Equation (1).

$$P=(115.0+68.0)/91.0=2.0109. \text{ The OPE index } Q=10. \quad \text{Equation (5)}$$

For $C_1=475$, the OPE index Q is 10. Generally, in case of Q<100, the necessity of the surgical operation on the jaw in orthodontic treatment increases. However, this case is a case showing a strong hypogrowth tendency of the mandible. Therefore, it can be decided as the same as the case of Equation (1).

$$P=(125.0+68.0)/91.0=2.1208. \text{ The OPE index } Q=120. \quad \text{Equation (6)}$$

For $C_1=630$, the OPE index Q is 120. Generally, in case of Q<130, the necessity of the surgical operation on the jaw in orthodontic treatment increases. However, this case is a case showing a strong hypogrowth tendency of the mandible. Therefore, it can be decided as the same as the case of Equation (1).

$$P=(127.0+68.0)/91.0=2.1428. \text{ The OPE index } Q=142. \quad \text{Equation (7)}$$

For $C_1=660$, the OPE index Q is 142. Generally, in case of Q<160, the necessity of the surgical operation on the jaw in orthodontic treatment increases. However, this case is a case showing a strong hypogrowth tendency of the mandible. Therefore, it can be decided as the same as the case of Equation (1).

$$P=(126.0+68.0)/91.0=2.1318. \text{ The OPE index } Q=131. \quad \text{Equation (8)}$$

For $C_1=650$, the OPE index Q is 131. Generally, in case of Q<150, the necessity of the surgical operation on the jaw in orthodontic treatment increases. However, this case is a case showing a strong hypogrowth tendency of the mandible. Therefore, it can be decided as the same as the case of Equation (1).

$$P=(115.0+70.0)/91.0=2.0329. \text{ The OPE index } Q=32. \quad \text{Equation (9)}$$

For $C_1$=490, the OPE index Q is 32. Generally, in case of Q<100, the necessity of the surgical operation on the jaw in orthodontic treatment increases. However, this case is a case showing a strong hypogrowth tendency of the mandible. Therefore, it can be decided as the same as the case of Equation (1).

$$P=(125.0+70.0)/91.0=2.1428. \text{ The OPE index } Q=142. \quad \text{Equation (10)}$$

For $C_1$=645, the OPE index Q is 142. Generally, in case of Q<150, the necessity of the surgical operation on the jaw in orthodontic treatment increases. However, this case is a case showing a strong hypogrowth tendency of the mandible. Therefore, it can be decided as the same as the case of Equation (1).

$$P=(127.0+70.0)/91.0=2.1648. \text{ The OPE index } Q=164. \quad \text{Equation (11)}$$

For $C_1$=675, the OPE index Q is 164. Generally, in case of Q<180, the necessity of the surgical operation on the jaw in orthodontic treatment increases. However, this case is a case showing a strong hypogrowth tendency of the mandible. Therefore, it can be decided as the same as the case of Equation (1).

$$P=(126.0+70.0)/91.0=2.1538. \text{ The OPE index } Q=153. \quad \text{Equation (12)}$$

For $C_1$=665, the OPE index Q is 153. Generally, in case of Q<150, the necessity of the surgical operation on the jaw in orthodontic treatment increases. However, this case is a case showing a strong hypogrowth tendency of the mandible. Therefore, it can be decided as the same as the case of Equation (1).

$$P=(115.0+70.0)/91.0=2.0329. \text{ The OPE index } Q=32. \quad \text{Equation (13)}$$

For $C_1$=435, the OPE index Q is 32. Generally, in case of Q<100, the necessity of the surgical operation on the jaw in orthodontic treatment increases. However, this case is a case showing a strong hypogrowth tendency of the mandible. Therefore, it can be decided as the same as the case of Equation (1).

$$P=(125.0+70.0)/91.0=2.1428. \text{ The OPE index } Q=142. \quad \text{Equation (14)}$$

For $C_1$=575, the OPE index Q is 142. Generally, in case of Q<160, the necessity of the surgical operation on the jaw in orthodontic treatment increases. However, this case is a case showing a strong hypogrowth tendency of the mandible. Therefore, it can be decided as the same as the case of Equation (1).

$$P=(127.0+70.0)/91.0=2.1648. \text{ The OPE index } Q=164. \quad \text{Equation (15)}$$

For $C_1$=610, the OPE index Q is 164. Generally, in case of Q<200, the necessity of the surgical operation on the jaw in orthodontic treatment increases. However, this case is a case showing a strong hypogrowth tendency of the mandible. Therefore, it can be decided as the same as the case of Equation (1).

$$P=(126.0+70.0)/91.0=2.1538. \text{ The OPE index } Q=153. \quad \text{Equation (16)}$$

For $C_1$=600, the OPE index Q is 153. Generally, in case of Q<190, the necessity of the surgical operation on the jaw in orthodontic treatment increases. However, this case is a case showing a strong hypogrowth tendency of the mandible. Therefore, it can be decided as the same as the case of Equation (1).

As explained, according to the method of calculating an index for deciding the necessity of surgically operating on the jaw according to the first embodiment, the OPE index Q can be calculated by using the distances (S–A), (S–$X_i$) and (Go–$X_j$) which are measured by cephalometric radiography. And, based on the OPE index Q, without being influenced by the experience of a dentist, the necessity of the surgical operation on the jaw in orthodontic treatment can be decided correctly with a short period of time, moreover with a certain objectivity.

2. Second Embodiment

In the second embodiment, a method of deciding the necessity of surgically operating on the jaw in orthodontic treatment is explained.

Figure 18:
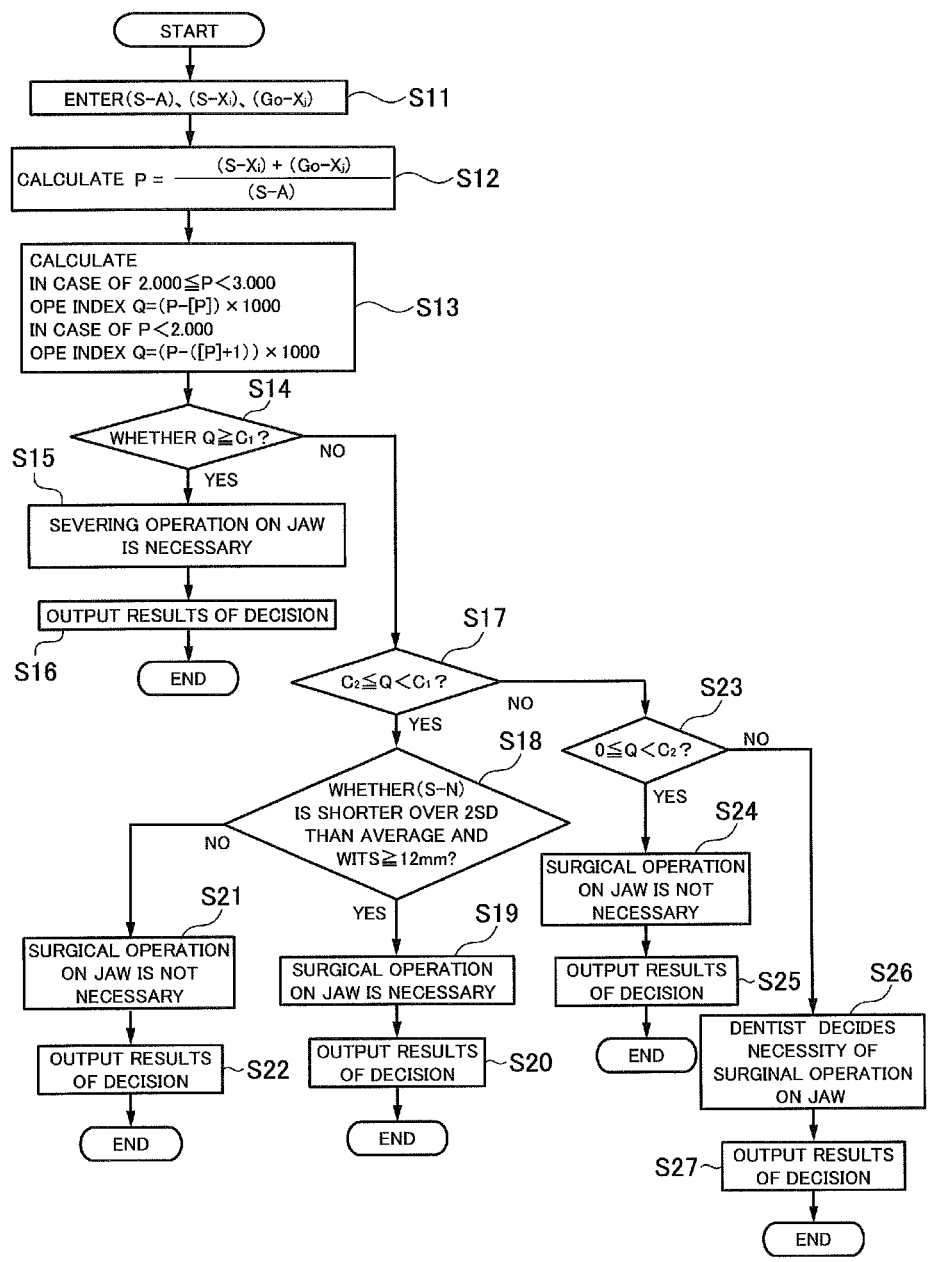
FIG. 18 A flowchart showing a method of deciding the necessity of surgically operating on the jaw in orthodontic treatment according to the second embodiment of the present invention.

A flowchart of the method of deciding the necessity of surgically operating on the jaw is shown in FIG. 18. According to the flowchart, a program is created, and is executed on a computer.

As the same as the first embodiment, before executing the method of deciding the necessity of surgically operating on the jaw, the distances (S–A), (S–$X_i$) and (Go–$X_j$) are measured.

As shown in FIG. 18, in step S11, the distances (S–A), (S–$X_i$) and (Go–$X_j$) which are measured as the above are entered.

In step S12, from the entered (S–A), (S–$X_i$) and (Go–$X_j$), P is calculated according to $$P=((S-X_i)+(Go-X_j))/(S-A).$$

In step S13, from P obtained by the calculation of the above, whether 2.000≤P<3.000 or P<2.000 is decided. As a result of the decision, in case of 2.000≤P<3.000, omitting the figures of the fourth decimal place and under of P, the OPE index Q is calculated according to $Q=(P-[P])\times1000$, and in case of $P<2.000$, the OPE index $Q$ is calculated according to $Q=(P-([P]+1))\times1000.$ In step S14, it is decided whether the OPE index Q calculated in this way is equal to or larger than $C_1$ or not.

In step S15, in case that the OPE index Q is equal to or larger than $C_1$, it is decided that the severing operation on the mandible is necessary in orthodontic treatment.

In step S16, the result of the decision that the severing operation on the jaw is necessary is output on a display, for example.

In case that Q is decided not equal to or larger than $C_1$ in step S14, in step S17, it is decided whether Q is equal to or larger than $C_2$ and less than $C_1$ or not.

In case that the OPE index Q is equal to or larger than $C_2$ and less than $C_1$, in step S18, it is decided whether the distance (S–N) is shorter over 2SD than the average, and Wits is equal to or larger than 12 mm or not. If applicable, in step S19, it is decided that the surgical operation on the jaw is necessary.

When being decided that the surgical operation on the jaw is necessary, in step S20, the result of the decision is output on a display, for example.

In step S18, when being decided that the distance (S–N) is not shorter over 2SD than the average, and Wits is not equal to or larger than 12 mm, in step S21, it is decided that the surgical operation on the jaw is not necessary.

When being decided that the surgical operation on the jaw is not necessary, in step S22, the result of the decision is output on a display, for example.

In case that Q is decided not equal to or larger than $C_2$ and less than $C_1$ in step S17, in step S23, it is decided whether Q is equal to and larger than 0 and less than $C_2$ or not.

When being decided that the OPE index Q is equal to or larger than 0 and less than $C_2$, in step S24, it is decided that the surgical operation on the jaw is not necessary.

When being decided that the surgical operation on the jaw is not necessary, in step S25, the result of the decision is output on a display, for example.

In case that the OPE index Q is not decided to be equal to or larger than 0 and less than $C_2$, the OPE index Q becomes negative. In this case, in step S26, a dentist decides the necessity of the surgical operation on the jaw, and in step S27, the result of diagnosis is output on a display, for example.

According to the method of deciding the necessity of surgically operating on the jaw according to the second embodiment, based on the OPE index Q to be calculated using the distances (S–A), (S–$X_i$) and (Go–$X_j$) which are measured by cephalometric radiography, the necessity of the surgical operation on the jaw in orthodontic treatment can be decided correctly with a short period of time, moreover with a certain objectivity without being influenced by the experience of a dentist.

3. Third Embodiment

In the third embodiment, an index for deciding disharmony of the maxilla and mandible is calculated by a method as the same as the method of calculating an index for deciding the necessity of surgically operating on the jaw in orthodontic treatment which is explained in the first embodiment.

According to the third embodiment, an index for deciding disharmony of the maxilla and mandible can be easily calculated. And based on the index for deciding disharmony of the maxilla and mandible, in dental treatment such as orthodontic treatment and medical treatment, disharmony of the maxilla and mandible can be decided correctly with a short period of time, moreover with a certain objectivity without being influenced by the experience of a dentist or a doctor.

4. Fourth Embodiment

In the fourth embodiment, a method of deciding disharmony of the maxilla and mandible is carried out by a method as the same as the method of deciding the necessity of surgically operating on the jaw in orthodontic treatment which is explained in the second embodiment.

According to the fourth embodiment, based on the index for deciding disharmony of the maxilla and mandible, in dental treatment such as orthodontic treatment and medical treatment, disharmony of the maxilla and mandible can be decided correctly with a short period of time, moreover with a certain objectivity without being influenced by the experience of a dentist or a doctor.

5. Fifth Embodiment

In the fifth embodiment, an index for deciding dentofacial deformity is calculated by a method as the same as the method of calculating an index for deciding the necessity of surgically operating on the jaw in orthodontic treatment which is explained in the first embodiment.

According to the fifth embodiment, the index for deciding dentofacial deformity can be easily calculated. And based on the index for deciding dentofacial deformity, the decision of dentofacial deformity can be done correctly with a short period of time, moreover with a certain objectivity without being influenced by the experience of a dentist or a doctor.

6. Sixth Embodiment

In the sixth embodiment, a method of deciding dentofacial deformity is carried out by a method as the same as the method of deciding the necessity of surgically operating on the jaw in orthodontic treatment which is explained in the second embodiment.

According to the sixth embodiment, based on the index for deciding detofacial deformity, the decision of dentofacial deformity can be done correctly with a short period of time, moreover with a certain objectivity without being influenced by the experience of a dentist or a doctor.

7. Seventh Embodiment

In the seventh embodiment, a method of calculating an OPE index for deciding the necessity of surgically operating on the jaw in orthodontic treatment is explained.

Figure 19:
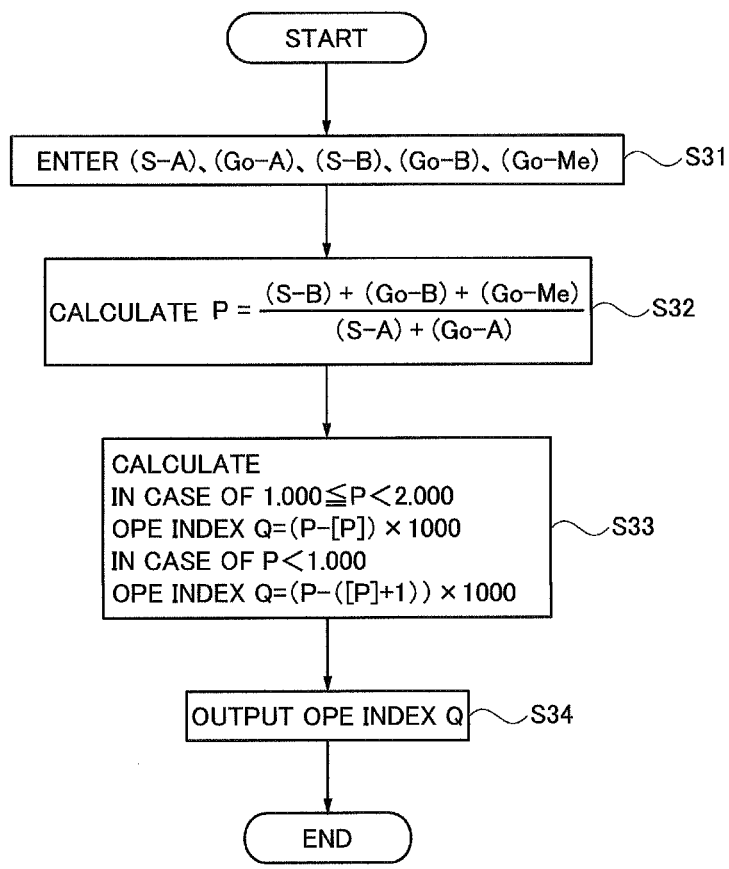
FIG. 19 A flowchart showing a method of calculating an index for deciding the necessity of surgically operating on the jaw in orthodontic treatment according to the seventh embodiment of the present invention.

A flowchart of the method of the calculation is shown in FIG. 19. According to the flowchart, a program is created, and is executed on a computer.

Before making the calculation, taking a cephalometric radiogram of a patient to be treated by orthodontic treatment, the distances (S–A), (Go–A), (S–B), (Go–B) and (Go–Me) are measured. The measurement of these distances are executed by the method which is explained before.

As shown in FIG. 19, in step S31, the distances (S–A), (Go–A), (S–B), (Go–B) and (Go–Me) which are measured by the above are entered.

In step S32, from the entered (S–A), (Go–A), (S–B), (Go–B) and (Go–Me), P is calculated according to $$P=((S-B)+(Go-B)+(Go-Me))/((S-A)+(Go-A)). \tag{25}$$

In step S33, omitting the figures of the fourth decimal place and under of P obtained by the calculation, in case of $1.000 \leq P < 2.000$, the OPE index Q is calculated according to $$Q=(P-[P]) \times 1000, \text{ and in case of } P<1.000,$$

the OPE index Q is calculated according to $$Q=(P-([P]+1)) \times 1000.$$

In step S34, the OPE index Q calculated as the above is output on a display, for example.

In case that the OPE index Q calculated as the above is equal to or larger than $C_3$, it can be diagnosed that the severing operation on the mandible is necessary in orthodontic treatment. Also, in a borderline case that the OPE index Q is equal to or larger than $C_4$ and less than $C_3$, a supplementary analysis is added by Wits analysis. In case that the result of Wits analysis is equal to or larger than 12 mm, it is decided that the surgical operation is adaptable, in other words, the surgical operation on the jaw is necessary. $C_3$ and $C_4$ can be decided suitably.

In case that the OPE index Q is less than $C_4$ and equal to or larger than 0, it can be diagnosed that the surgical operation on the jaw is not necessary in orthodontic treatment.

In case that the OPE index Q is negative, which denotes a remarkable hypogrowth tendency of the mandible or overgrowth tendency of the maxilla, it is necessary to consider the surgical operation on the jaw.

Generally, in addition to the OPE index Q, a dentist finally decides the necessity of surgically operating on the jaw by combining other inspection results such as the conventional cephalometric analysis focusing mainly on angle measurement, etc.

Example 13

From FIG. 3 showing the tracing made based on the cephalometric radiogram of the patient 1 taken in the example 1, the distances (S–A), (Go–A), (S–B), (Go–B) and (Go–Me) were measured. The results are: (S–A)=78.0 mm, (Go–A)=77.0 mm, (S–B)=123.0 mm, (Go–B)=78.0 mm and (Go–Me)=78.0 mm. Using the data, the calculation of P is given as follows: (123.0+78.0+78.0)/(78.0+77.0)=1.8000. Therefore, the OPE index Q is 800.

For example, if $C_3$ is set as $C_3$=740, the OPE index Q is 800, so it can be decided that the patient 1 needs the severing operation on the mandible in orthodontic treatment.

Therefore, the necessary severing operation on the mandible was performed. From FIG. 4 showing the tracing made based on the cephalometric radiogram after the severing operation on the mandible of the patient 1 taken in the example 1, the distances (S–A), (Go–A), (S–B), (Go–B) and (Go–Me) were measured. The results are: (S–A)=78.0 mm, (Go–A)=79.0 mm, (S–B)=111.0 mm, (Go–B)=73.0 mm and (Go–Me)=73.0 mm. Using the data, the calculation of P is given as follows: (111.0+73.0+73.0)/(78.0+79.0)=1.6369. Therefore, the OPE index Q is 636.

For $C_3$=740, the OPE index Q is 636, so it can be decided that the patient 1 is able to be treated by orthodontic treatment as a result of the severing operation on the mandible.

Example 14

From FIG. 5 showing the tracing made based on the cephalometric radiogram of the patient 2 taken in the example 2, the distances (S–A), (Go–A), (S–B), (Go–B) and (Go–Me) were measured. The results are: (S–A)=83.0 mm, (Go–A)=78.0 mm, (S–B)=123.0 mm, (Go–B)=80.0 mm and (Go–Me)=81.0 mm. Using the data, the calculation of P is given as follows: (123.0+80.0+81.0)/(83.0+78.0)=1.7639. Therefore, the OPE index Q is 763.

For $C_3$=740, the OPE index Q is 763, so it can be decided that the patient 2 needs the severing operation on the mandible in orthodontic treatment.

Therefore, the necessary severing operation on the mandible was performed. From FIG. 6 showing the tracing made based on the cephalometric radiogram taken after the severing operation of the mandible of the patient 2, the distances (S–A), (Go–A), (S–B), (Go–B) and (Go–Me) were measured. The results are: (S–A)=83.0 mm, (Go–A)=83.0 mm, (S–B)=116.0 mm, (Go–B)=80.0 mm and (Go–Me)=80.0 mm. Using the data, the calculation of P is given as follows: (116.0+80.0+80.0)/(83.0+83.0)=1.6626. Therefore, the OPE index Q is 662.

For $C_3$=740, the OPE index Q is 662, so it can be decided that the patient 2 is able to be treated by orthodontic treatment as a result of the severing operation on the mandible.

Example 15

From FIG. 7 showing the tracing made based on the cephalometric radiogram of the patient 3 taken in the example 3, the distances (S–A), (Go–A), (S–B), (Go–B) and (Go–Me) were measured. The results are: (S–A)=88.0 mm, (Go–A)=85.0 mm, (S–B)=126.0 mm, (Go–B)=80.0 mm and (Go–Me)=78.0 mm. Using the data, the calculation of P is given as follows: (126.0+80.0+78.0)/(88.0+85.0)=1.6416. Therefore, the OPE index Q is 641.

This is a case of light skeletal class III. However, for $C_3$=740 the OPE index Q is 641, so it can be decided that the patient 3 does not need the surgical operation on the jaw in orthodontic treatment.

Example 16

From FIG. 8 showing the tracing made based on the cephalometric radiogram of the patient 4 taken in the example 4, the distances (S–A), (Go–A), (S–B), (Go–B) and (Go–Me) were measured. The results are: (S–A)=85.0 mm, (Go–A)=78.0 mm, (S–B)=119.0 mm, (Go–B)=76.0 mm and (Go–Me)=77.0 mm. Using the data, the calculation of P is given as follows: (119.0+76.0+77.0)/(85.0+78.0)=1.6687. Therefore, the OPE index Q is 668.

This is a case of skeletal class III. However, for $C_3$=740 the OPE index Q is 668, so it can be decided that the patient 4 does not need the surgical operation on the jaw in orthodontic treatment.

Example 17

From FIG. 9 showing the tracing made based on the cephalometric radiogram of the patient 5 taken in the example 5, the distances (S–A), (Go–A), (S–B), (Go–B) and (Go–Me) were measured. The results are: (S–A)=75.0 mm, (Go–A)=74.0 mm, (S–B)=109.0 mm, (Go–B)=73.0 mm and (Go–Me)=70.0 mm. Using the data, the calculation of P is given as follows: (109.0+73.0+70.0)/(75.0+74.0)=1.6912. Therefore, the OPE index Q is 691.

For $C_3$=740 the OPE index Q is 691, so it is a borderline case. Wits is 10.0 mm, which shows a very strong skeletal case. However, the Wits is equal to or less than 12 mm, further with (S–N)=65.0 mm, so it can be decided that the surgical operation on the jaw is not necessary in orthodontic treatment.

Example 18

From FIG. 10 showing the tracing made based on the cephalometric radiogram of the patient 6 taken in the example 6, the distances (S–A), (Go–A), (S–B), (Go–B) and (Go–Me) were measured. The results are: (S–A)=87.0 mm, (Go–A)=79.0 mm, (S–B)=128.0 mm, (Go–B)=80.0 mm and (Go–Me)=80.0 mm. Using the data, the calculation of P is given as follows: (128.0+80.0+80.0)/(87.0+79.0)=1.7349. Therefore, the OPE index Q is 734.

For $C_3$=740 the OPE index Q is 734, so it is a borderline case. As Wits is 12.0 mm, further with (S–N)=68.0 mm, it shows a skeletal class III, and it can be decided that the patient 6 suffers from dentofacial deformity, and can be decided that the severing operation on the mandible is necessary.

Therefore, the necessary severing operation on the mandible was performed. From FIG. 11 showing the tracing made based on the cephalometric radiogram taken after the severing operation on the mandible of the patient 6, the distances (S–A), (Go–A), (S–B), (Go–B) and (Go–Me) were measured. The results are: (S–A)=87.0 mm, (Go–A)=77.0 mm, (S–B)=121.0 mm, (Go–B)=73.0 mm and (Go–Me)=73.0 mm. Using the data, the calculation of P is given as follows: (121.0+73.0+73.0)/(87.0+77.0)=1.6280. Therefore, the OPE index Q is 628.

For $C_3$=740 the OPE index Q is 628, so it can be decided that the patient 6 can be treated by orthodontic treatment as a result of the severing operation on the mandible.

Example 19

From FIG. 12 showing the tracing made based on the cephalometric radiogram of the patient 7 taken in the example 7, the distances (S–A), (Go–A), (S–B), (Go–B) and (Go–Me) were measured. The results are: (S–A)=86.0 mm, (Go–A)=86.0 mm, (S–B)=111.0 mm, (Go–B)=73.0 mm and (Go–Me)=69.0 mm. Using the data, the calculation of P is given as follows: (111.0+73.0+69.0)/(86.0+86.0)=1.4709. Therefore, the OPE index Q is 470.

For $C_3=740$ the OPE index Q is 470, so there is a withdrawing tendency of the mandible. However, it can be decided that the patient 7 does not need the surgical operation on the jaw in orthodontic treatment, and orthodontic treatment with a tooth extracting treatment is adaptable.

Example 20

From FIG. 13 showing the tracing made based on the cephalometric radiogram of the patient 8 taken in the example 8, the distances (S–A), (Go–A), (S–B), (Go–B) and (Go–Me) were measured. The results are: (S–A)=90.0 mm, (Go–A)=79.0 mm, (S–B)=127.0 mm, (Go–B)=80.0 mm and (Go–Me)=80.0 mm. Using the data, the calculation of P is given as follows: (127.0+80.0+80.0)/(90.0+79.0)=1.6982. Therefore, the OPE index Q is 698.

For $C_3=740$ the OPE index Q is 698, so it can be decided that the patient 8 does not need the surgical operation on the jaw in orthodontic treatment.

Example 21

From FIG. 14 showing the tracing made based on the cephalometric radiogram of the patient 9 taken in the example 9, the distances (S–A), (Go–A), (S–B), (Go–B) and (Go–Me) were measured. The results are: (S–A)=79.0 mm, (Go–A)=81.0 mm, (S–B)=105.0 mm, (Go–B)=74.0 mm and (Go–Me)=73.0 mm. Using the data, the calculation of P is given as follows (105.0+74.0+73.0)/(79.0+81.0)=1.575. Therefore, the OPE index Q is 575.

For $C_3=740$ the OPE index Q is 575, so it can be decided that the patient 9 does not need the surgical operation on the jaw in orthodontic treatment.

Example 22

From FIG. 15 showing the tracing made based on the cephalometric radiogram of the patient 10 taken in the example 10, the distances (S–A), (Go–A), (S–B), (Go–B) and (Go–Me) were measured. The results are: (S–A)=81.0 mm, (Go–A)=83.0 mm, (S–B)=103.0 mm, (Go–B)=72.0 mm and (Go–Me)=70.0 mm. Using the data, the calculation of P is given as follows: (103.0+72.0+70.0)/(81.0+83.0)=1.4939. Therefore, the OPE index Q is 493.

This is a case of non-skeletal. However, for $C_3=740$ the OPE index Q is 493, so it can be decided that the patient 10 does not need the surgical operation on the jaw in orthodontic treatment, and orthodontic treatment with a non-tooth extraction is adaptable.

Example 23

From FIG. 16 showing the tracing made based on the cephalometric radiogram of the patient 11 taken in the example 11, the distances (S–A), (Go–A), (S–B), (Go–B) and (Go–Me) were measured. The results are: (S–A)=81.0 mm, (Go–A)=78.0 mm, (S–B)=108.0 mm, (Go–B)=69.0 mm and (Go–Me)=68.0 mm. Using the data, the calculation of P is given as follows: (108.0+69.0+68.0)/(81.0+78.0)=1.5408. Therefore, the OPE index Q is 540.

For $C_3=740$ the OPE index Q is 540, and Wits is 2.0 mm, which shows a non-skeletal case. However, it can be decided that the patient 11 does not need the surgical operation on the jaw in orthodontic treatment, and orthodontic treatment with a non-tooth extraction is adaptable.

Example 24

From FIG. 17 showing the tracing made based on the cephalometric radiogram of the patient 12 taken in the example 12, the distances (S–A), (Go–A), (S–B), (Go–B) and (Go–Me) were measured. The results are: (S–A)=91.0 mm, (Go–A)=87.0 mm, (S–B)=115.0 mm, (Go–B)=70.0 mm and (Go–Me)=65.0 mm. Using the data, the calculation of P is given as follows: (115.0+70.0+65.0)/(91.0+87.0)=1.4044. Therefore, the OPE index Q is 404.

For $C_3=740$ the OPE index Q is 404, so it is a borderline case. The patient 12 has a strong hypogrowth tendency of the mandible, and it can be decided that the patient 12 does not need the surgical operation on the jaw in orthodontic treatment.

As explained, by the method of calculating an index for deciding the necessity of surgically operating on the jaw according to the seventh embodiment, using the distances (S–A), (Go–A), (S–B), (Go–B) and (Go–Me) which are measured by cephalometric radiography, the OPE index Q can be calculated. And based on the OPE index Q, without being influenced by the experience of a dentist, the necessity of the surgical operation on the jaw in orthodontic treatment can be diagnosed correctly with a short period of time, moreover with a certain objectivity.

8. Eighth Embodiment

In the eighth embodiment, a method of deciding the necessity of surgically operating on the jaw in orthodontic treatment is explained.

Figure 20:
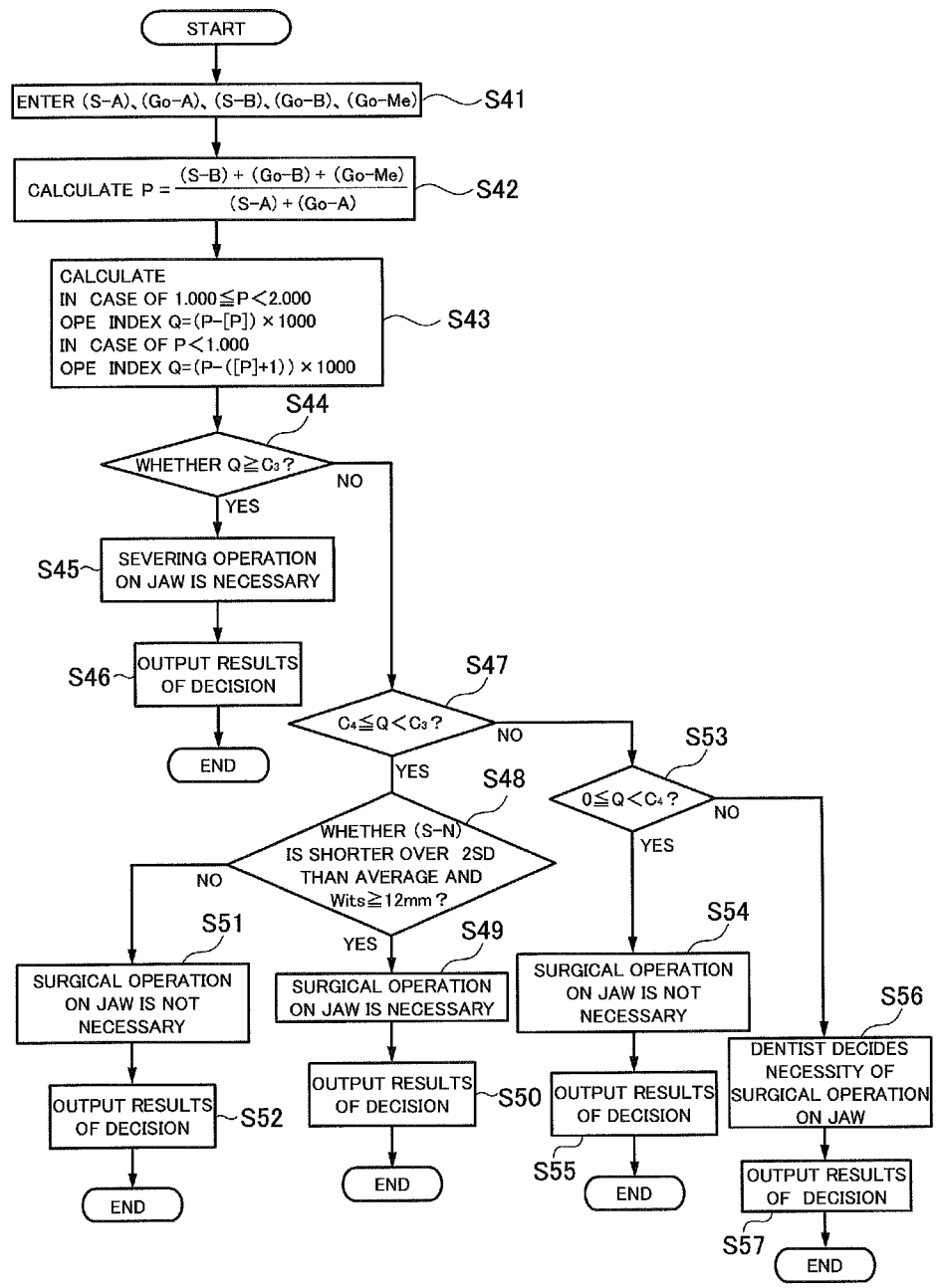
FIG. 20 A flowchart showing a method of deciding the necessity of surgically operating on the jaw in orthodontic treatment according to the eighth embodiment of the present invention.

A flowchart of the method of deciding the necessity of surgically operating on the jaw is shown in FIG. 20. A program is created according to the flowchart, and is executed on a computer.

As the same as the eighth embodiment, before executing the method of deciding the necessity of surgically operating on the jaw, the distances (S–A), (Go–A), (S–B), (Go–B) and (Go–Me) are measured.

As shown in FIG. 20, in step S41, the distances (S–A), (Go–A), (S–B), (Go–B) and (Go–Me) which are measured by the above are entered.

In step S42, from the entered (S–A), (Go–A), (S–B), (Go–B) and (Go–Me), P is calculated according to $P=((S-B)+(Go-B)+(Go-Me))/((S-A)+(Go-A))$.

In step S43, from P obtained by the calculation, it is decided whether $1.000 \leq P < 2.000$ or $P < 1.000$. As a result of the decision, in case of $1.000 \leq P < 2.000$, omitting the figures of the fourth decimal place and under of P, the OPE index Q is calculated according to $Q=(P-[P]) \times 1000$ and in case of $P < 1.000$, the OPE index Q is calculated according to $Q=(P-([P]+1)) \times 1000$.

In step S44, the OPE index Q calculated as the above is decided whether equal to or larger than $C_3$ or not.

In step S45, in case that the OPE index Q is equal to or larger than $C_3$, it is decided that the severing operation on the mandible is necessary in orthodontic treatment.

In step S46, the result of the decision that the severing operation of the mandible is necessary is output on a display, for example.

In case that Q is decided not to be equal to or larger than $C_3$ in step S44, in step S47, it is decided whether Q is equal to or larger than $C_4$ and less than $C_3$ or not.

In step S48, in case that the OPE index Q is equal to or larger than $C_4$ and less than $C_3$, it is decided whether Wits is equal to or larger than 12 mm or not. If Wits is equal to or larger than 12 mm, in step S49, it is decided that the surgical operation on the jaw is necessary.

When being decided that the surgical operation on the jaw is necessary, in step S50, the result of the decision is output on a display, for example.

In step S48, when Wits is decided not to be equal to or larger than 12 mm, in step S41, it is decided that the surgical operation on the jaw is not necessary.

When being decided that the surgical operation on the jaw is not necessary, in step S52, the result of the decision is output on a display, for example.

In case that Q is decided not equal to or larger than $C_4$ and less than $C_3$ in step S47, in step S53, it is decided whether Q is equal to or larger than 0 and less than $C_4$ or not.

When the OPE index Q is decided equal to or larger than 0 and less than $C_4$, in step S54, it is decided that the surgical operation on the jaw is not necessary.

When being decided that the surgical operation on the jaw is not necessary, in step S55, the result of the decision is output on a display, for example.

In case that the OPE index Q is not decided to be equal to or larger than 0 and less than $C_4$, the OPE index Q becomes negative. In this case, in step S56, a dentist decides the necessity of the surgical operation on the jaw, and in step S57, the result of the decision is output on a display, for example.

By the method of deciding the necessity of surgically operating on the jaw according to the eighth embodiment, based on the OPE index Q to be calculated by using the distances (S–A), (Go–A), (S–B), (Go–B) and (Go–Me) which are measured by cephalometric radiography, without being influenced by the experience of a dentist, the necessity of the surgical operation on the jaw in orthodontic treatment can be decided correctly with a short period of time, moreover with a certain objectivity.

9. Ninth Embodiment

In the ninth embodiment, an index for deciding disharmony of the maxilla and mandible is calculated by a method as the same as the method of calculating an index for deciding the necessity of surgically operating on the jaw in orthodontic treatment explained in the seventh embodiment.

According to the ninth embodiment, the index for deciding disharmony of the maxilla and mandible can be calculated easily. And based on the index for deciding disharmony of the maxilla and mandible, without being influenced by the experience of a dentist or a doctor, disharmony of the maxilla and mandible in dental treatment such as orthodontic treatment, etc. or medical treatment can be decided correctly with a short period of time, moreover with a certain objectivity.

10. Tenth Embodiment

In the tenth embodiment, a method of deciding disharmony of the maxilla and mandible is carried out by a method as the same as the method of deciding the necessity of surgically operating on the jaw in orthodontic treatment as explained in the eighth embodiment.

According to the tenth embodiment, based on the index for deciding disharmony of the maxilla and mandible, without being influenced by the experience of a dentist or a doctor, disharmony of the maxilla and mandible in dental treatment such as orthodontic treatment, etc. or medical treatment can be decided correctly with a short period of time, moreover with a certain objectivity.

11. Eleventh Embodiment

In the eleventh embodiment, an index for deciding dentofacial deformity is calculated by a method as the same as the method of calculating an index for deciding the necessity of surgically operating on the jaw in orthodontic treatment explained in the seventh embodiment.

According to the eleventh embodiment, the index for deciding dentofacial deformity can be calculated easily. And based on the index for deciding dentofacial deformity, without being influenced by the experience of a dentist or a doctor, dentofacial deformity can be decided correctly with a short period of time, moreover with a certain objectivity.

12. Twelfth Embodiment

In the twelfth embodiment, a method of deciding dentofacial deformity is carried out by a method as the same as the method of deciding the necessity of surgically operating on the jaw in orthodontic treatment as explained in the eighth embodiment.

According to the twelfth embodiment, based on the index for deciding dentofacial deformity, without being influenced by the experience of a dentist or a doctor, dentofacial deformity can be decided correctly with a short period of time, moreover with a certain objectivity.

13. Thirteenth Embodiment

In the thirteenth embodiment, a method of calculating an index for hypogrowth of the maxilla is explained.

Before calculating, a cephalometric radiograph of a patient is taken, and the distances (S–N), (S–A) and (Go–A) are measured. These distances can be measured by the method which was explained before.

At first, in step S61, the distances (S–N), (S–A) and (Go–A) which are measured by the above are entered.

In step S62, from the entered (S–N), (S–A) and (Go–A), P is calculated according to $$P=((S-A)+(Go-A))/(S-N). \qquad (17)$$

In step S63, from P obtained by the calculation, omitting the figures of the fourth decimal place and under of P, in case of 2.000≤P<3.000, the index Q for hypogrowth of the maxilla is calculated according to $$Q=(P-[P])\times 1000$$

and in case of P<2.000, the index Q for hypogrowth of the maxilla is calculated according to $$Q=(P-([P]+1))\times 1000.$$

In step S64, the index Q for hypogrowth of the maxilla calculated as the above is output on a display, for example.

From the index Q for hypogrowth of the maxilla calculated as the above, it can be decided objectively about the presence or absence of hypogrowth or overgrowth of the maxilla or the degree of hypogrowth or overgrowth of the maxilla.

Example 25

From FIG. 3 showing the tracing made based on the cephalometric radiograph of the patient 1 taken in the example 1, the distances (S–N), (S–A) and (Go–A) were measured. The results are: (S–N)=67.0 mm, (S–A)=78.0 mm and (Go–A)=77.0 mm. Using the data, the calculation of P is given as follows: (78.0+77.0)/67.0=2.3134. Therefore, the index Q for hypogrowth of the maxilla is 313, and the patient 1 can be decided that the maxilla is normal.

From FIG. 4 showing the tracing made based on the cephalometric radiograph after the severing operation on the mandible of the patient 1 taken in the example 1, the distances (S–N), (S–A) and (Go–A) were measured. The results are: (S–N)=67.0 mm, (S–A)=78.0 mm and (Go–A)=79.0 mm. Using the data, the calculation of P is given as follows: (78.0+79.0)/67.0=2.3432. Therefore, the index Q for hypogrowth of the maxilla is 343, and the patient 1 can be decided that the maxilla is normal.

Example 26

From FIG. 5 showing the tracing made based on the cephalometric radiogram of the patient 2 taken in the example 2, the distances (S–N), (S–A) and (Go–A) were measured. The results are: (S–N)=69.0 mm, (S–A)=83.0 mm and (Go–A)=78.0 mm. Using the data, the calculation of P is given as follows: (83.0+78.0)/69.0=2.3333. Therefore, the index Q for hypogrowth of the maxilla is 333, and the patient 2 can be decided that the maxilla is normal.

From FIG. 6 showing the tracing made based on the cephalometric radiogram after the severing operation on the mandible of the patient 2, the distances (S–N), (S–A) and (Go–A) were measured. The results are: (S–N)=69.0 mm, (S–A)=83.0 mm and (Go–A)=83.0 mm. Using the data, the calculation of P is given as follows: (83.0+83.0)/69.0=2.4057. Therefore, the index Q for hypogrowth of the maxilla is 405, and the patient 2 can be decided that the maxilla is normal.

Example 27

From FIG. 7 showing the tracing made based on the cephalometric radiogram of the patient 3 taken in the example 3, the distances (S–N), (S–A) and (Go–A) were measured. The results are: (S–N)=67.0 mm, (S–A)=88.0 mm and (Go–A)=85.0 mm. Using the data, the calculation of P is given as follows: (88.0+85.0)/67.0=2.5820. Therefore, the index Q for hypogrowth of the maxilla is 582, and the patient 3 can be decided that there is overgrowth of the maxilla.

Example 28

From FIG. 8 showing the tracing made based on the cephalometric radiogram of the patient 4 taken in the example 4, the distances (S–N), (S–A) and (Go–A) were measured. The results are: (S–N)=64.0 mm, (S–A)=85.0 mm and (Go–A)=78.0 mm. Using the data, the calculation of P is given as follows: (85.0+78.0)/64.0=2.5468. Therefore, the index Q for hypogrowth of the maxilla is 546, and the patient 4 can be decided that there is overgrowth of the maxilla.

Example 29

From FIG. 9 showing the tracing made based on the cephalometric radiogram of the patient 5 taken in the example 5, the distances (S–N), (S–A) and (Go–A) were measured. The results are: (S–N)=65.0 mm, (S–A)=75.0 mm and (Go–A)=74.0 mm. Using the data, the calculation of P is given as follows: (75.0+74.0)/65.0=2.2923. Therefore, the index Q for hypogrowth of the maxilla is 292, and the patient 5 can be decided that the maxilla is normal.

Example 30

From FIG. 10 showing the tracing made based on the cephalometric radiogram of the patient 6 taken in the example 6, the distances (S–N), (S–A) and (Go–A) were measured. The results are: (S–N)=68.0 mm, (S–A)=87.0 mm and (Go–A)=79.0 mm. Using the data, the calculation of P is given as follows: (87.0+79.0)/68.0=2.4411. Therefore, the index Q for hypogrowth of the maxilla is 441, and the patient 6 can be decided that the maxilla is normal.

From FIG. 11 showing the tracing made based on the cephalometric radiogram after the severing operation on the mandible of the patient 6, the distances (S–N), (S–A) and (Go–A) were measured. The results are: (S–N)=68.0 mm, (S–A)=87.0 mm and (Go–A)=77.0 mm. Using the data, the calculation of P is given as follows: (87.0+77.0)/68.0=2.4117. Therefore, the index Q for hypogrowth of the maxilla is 411, and the patient 6 can be decided that the maxilla is normal.

Example 31

From FIG. 12 showing the tracing made based on the cephalometric radiogram of the patient 7 taken in the example 7, the distances (S–N), (S–A) and (Go–A) were measured. The results are: (S–N)=67.0 mm, (S–A)=86.0 mm and (Go–A)=86.0 mm. Using the data, the calculation of P is given as follows: (86.0+86.0)/67.0=2.5671. Therefore, the index Q for hypogrowth of the maxilla is 567, and the patient 7 can be decided that there is overgrowth of the maxilla.

Example 32

From FIG. 13 showing the tracing made based on the cephalometric radiogram of the patient 8 taken in the example 8, the distances (S–N), (S–A) and (Go–A) were measured. The results are: (S–N)=68.0 mm, (S–A)=90.0 mm and (Go–A)=79.0 mm. Using the data, the calculation of P is given as follows: (90.0+79.0)/68.0=2.4852. Therefore, the index Q for hypogrowth of the maxilla is 485, and the patient 8 can be decided that there is overgrowth of the maxilla.

Example 33

From FIG. 14 showing the tracing made based on the cephalometric radiogram of the patient 9 taken in the example 9, the distances (S–N), (S–A) and (Go–A) were measured. The results are: (S–N)=68.0 mm, (S–A)=79.0 mm and (Go–A)=81.0 mm. Using the data, the calculation of P is given as follows: (79.0+81.0)/68.0=2.3529. Therefore, the index Q for hypogrowth of the maxilla is 352, and the patient 9 can be decided that the maxilla is normal.

Example 34

From FIG. 15 showing the tracing made based on the cephalometric radiogram of the patient 10 taken in the example 10, the distances (S–N), (S–A) and (Go–A) were measured. The results are: (S–N)=69.0 mm, (S–A)=81.0 mm and (Go–A)=83.0 mm. Using the data, the calculation of P is given as follows: (81.0+83.0)/69.0=2.3768. Therefore, the index Q for hypogrowth of the maxilla is 376, and the patient 10 can be decided that the maxilla is normal.

Example 35

From FIG. 16 showing the tracing made based on the cephalometric radiogram of the patient 11 taken in the example 11, the distances (S–N), (S–A) and (Go–A) were measured. The results are: (S–N)=63.0 mm, (S–A)=81.0 mm and (Go–A)=78.0 mm. Using the data, the calculation of P is given as follows: (81.0+78.0)/63.0=2.5238. Therefore, the index Q for hypogrowth of the maxilla is 523, and the patient 11 can be decided that there is overgrowth of the maxilla.

Example 36

From FIG. 17 showing the tracing made based on the cephalometric radiogram of the patient 12 taken in the example 12, the distances (S–N), (S–A) and (Go–A) were measured. The results are: (S–N)=74.0 mm, (S–A)=91.0 mm and (Go–A)=87.0 mm. Using the data, the calculation of P is given as follows: (91.0+87.0)/74.0=2.4054. Therefore, the index Q for hypogrowth of the maxilla is 405, and the patient 12 can be decided that the maxilla is normal.

Example 37

Figure 21:
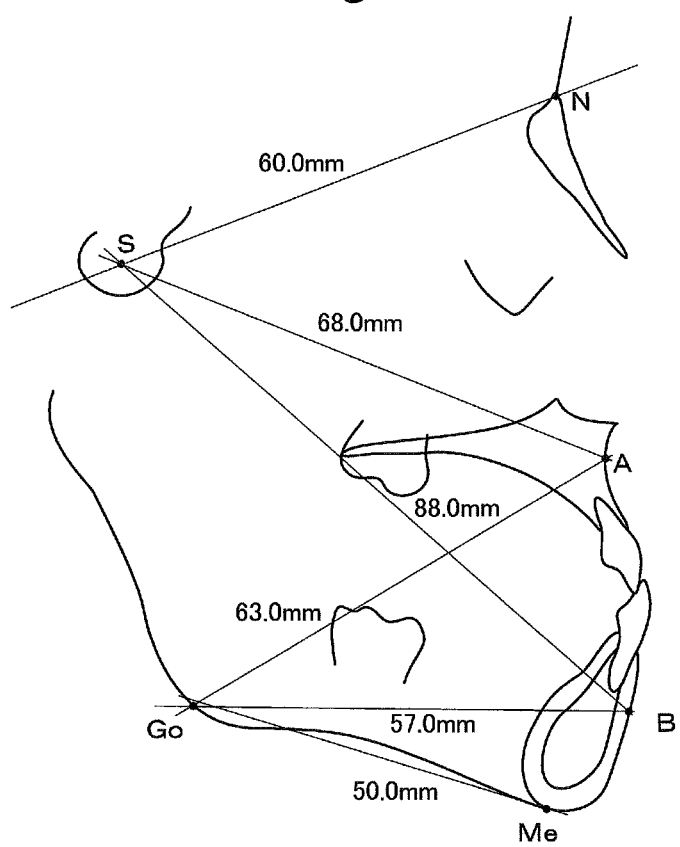
FIG. 21 A tracing made based on a cephalometric radiogram of a patient 13.

A cephalometric radiogram of a patient 13 was taken. A tracing made based on the cephalometric radiogram is shown in FIG. 21. From FIG. 21, the distances (S–N), (S–A) and (Go–A) were measured. The results are: (S–N)=60.0 mm, (S–A)=68.0 mm and (Go–A)=63.0 mm. Using the data, the calculation of P is given as follows: (68.0+63.0)/60.0=2.1833. Therefore, the index Q for hypogrowth of the maxilla is 183, and the patient 13 can be decided that there is hypogrowth of the maxilla. Using the distances (S–A), (S–B) and (Go–Me) obtained from FIG. 21, the OPE index Q was calculated by the Equation (1). From P=(88.0+50.0)/68.0=2.0294, Q=29.

Figure 22:
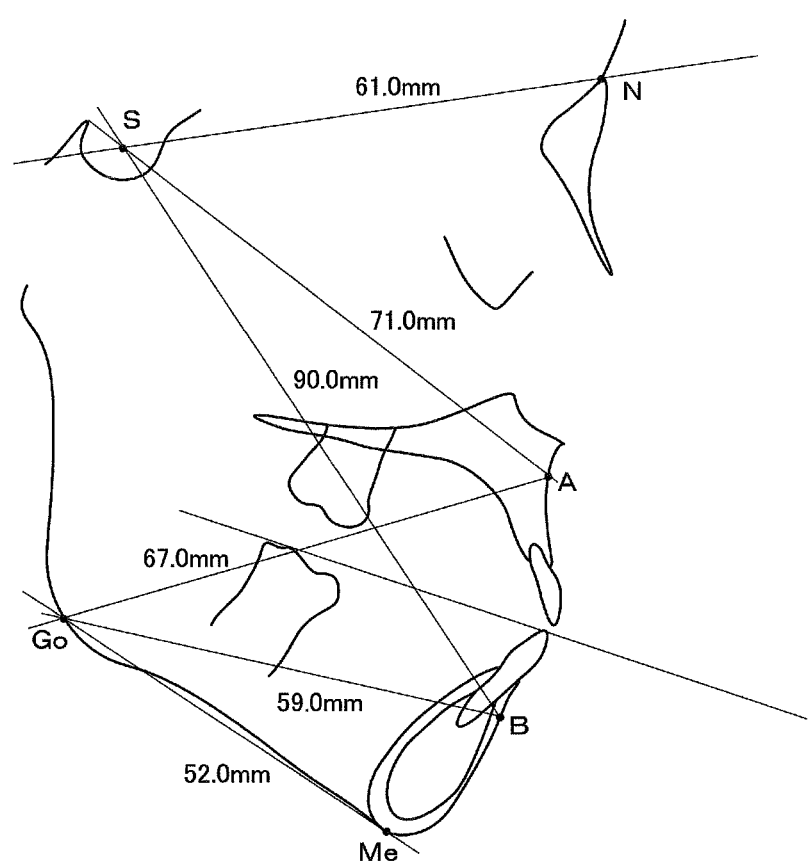
FIG. 22 A tracing made based on a cephalometric radiogram of the patient 13 after using a facial mask.

A proper facial mask was attached to the face of the patient 13 for improvement of hypogrowth of the maxilla. After using the facial mask for two years, a cephalometric radiogram of the patient 13 was taken. A tracing made based on the cephalometric radiogram is shown in FIG. 22. From FIG. 22, (S–N)=61.0 mm, (S–A)=71.0 mm and (Go–A)=67.0 mm. Using the data, the calculation of P is given as follows: (71.0+67.0)/61.0=2.2622. Therefore, the index Q for hypogrowth of the maxilla is 262, so it is understood that the maxilla was improved to be normal. Using the distances (S–A), (S–B) and (Go–Me) obtained from FIG. 22, the OPE index Q was calculated by the Equation (1). From P=(90.0+52.0)/71.0=2.0000, Q=0.

Example 38

Figure 23:
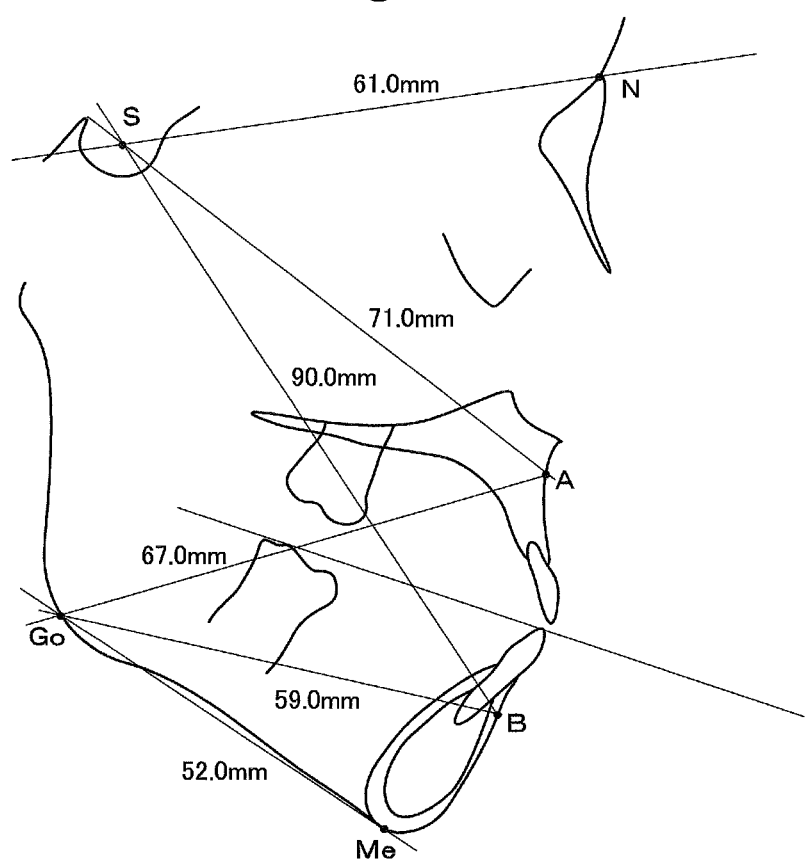
FIG. 23 A tracing made based on a cephalometric radiogram of a patient 14.

A cephalometric radiogram of a patient 14 was taken. A tracing made based on the cephalometric radiogram is shown in FIG. 23. From FIG. 23, (S–N)=69.0 mm, (S–A)=77.0 mm and (Go–A)=76.0 mm. Using the data, the calculation of P is given as follows: (77.0+76.0)/69.0=2.2173. Therefore, the index Q for hypogrowth of the maxilla is 217, and the patient 14 can be decided that the maxilla is normal. Using the distances (S–A), (S–B) and (Go–Me) obtained from FIG. 23, the OPE index Q was calculated by the Equation (1). From P=(110.0+73.0)/77.0=2.3766, Q=376.

Figure 24:
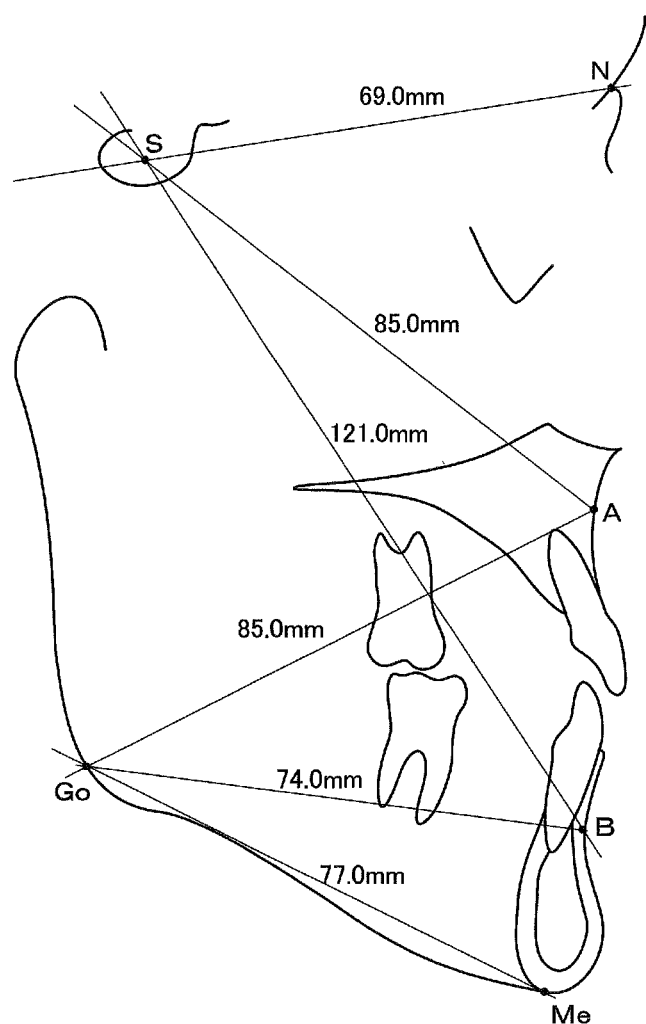
FIG. 24 A tracing made based on a cephalometric radiogram taken after the severing operation on the mandible of the patient 14.

As the OPE index Q, which is calculated by the Equation (1), is 376, it is a borderline case. Accordingly, the severing operation on the mandible was performed. After 7 years from the severing operation on the mandible, a cephalometric radiogram of the patient 14 was taken. A tracing made based on the cephalometric radiogram is shown in FIG. 24. From FIG. 24, (S–N)=69.0 mm, (S–A)=85.0 mm and (Go–A)=85.0 mm. Using the data, the calculation of P is given as follows: (85.0+85.0)/69.0=2.4637. Therefore, the index Q for hypogrowth of the maxilla is 463, and the patient 14 can be decided that the maxilla is normal. Using the distances (S–A), (S–B) and (Go–Me) obtained from FIG. 24, the OPE index Q was calculated by the Equation (1). From P=(121.0+77.0)/85.0=2.3294, Q=329.

Example 39

Figure 25:
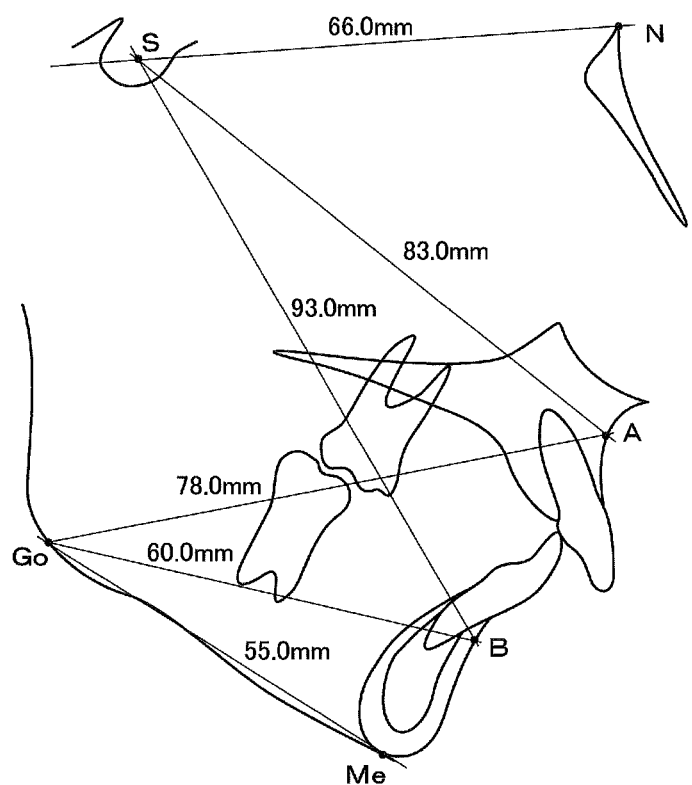
FIG. 25 A tracing made based on a cephalometric radiogram of a patient 15.

A cephalometric radiogram of a patient 15 was taken. A tracing made based on the cephalometric radiogram is shown in FIG. 25. From FIG. 25, (S–N)=66.0 mm, (S–A)=83.0 mm and (Go–A)=78.0 mm. Using the data, the calculation of P is given as follows: (83.0+78.0)/66.0=2.4393. Therefore, the index Q for hypogrowth of the maxilla is 439, and the patient 15 can be decided that the maxilla is normal. Using the distances (S–A), (S–B) and (Go–Me) obtained from FIG. 25, the OPE index Q was calculated by the Equation (1). From P=(93.0+55.0)/83.0=1.7831, Q=−217.

Figure 26:
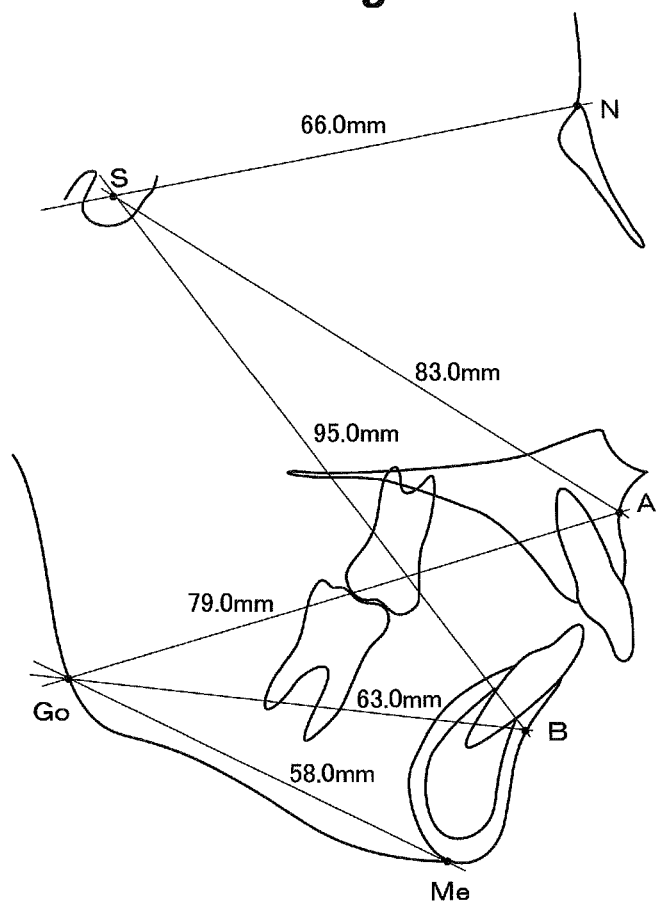
FIG. 26 A tracing made based on a cephalometric radiogram of the patient 15 after using a headgear.

As the patient 15 can be decided that there is hypogrowth of the mandible, as will be described later, a proper headgear was attached to the head of the patient 15 for improvement of hypogrowth of the mandible. After using the headgear for one year and 9 months, a cephalometric radiogram of the patient 15 was taken. A tracing made based on the cephalometric radiogram is shown in FIG. 26. From FIG. 26, (S–N)=66.0 mm, (S–A)=83.0 mm and (Go–A)=79.0 mm. Using the data, the calculation of P is given as follows: (83.0+79.0)/66.0=2.4545. Therefore, the index Q for hypogrowth of the maxilla is 454, so it is understood that the maxilla is maintained to be normal. Using the distances (S–A), (S–B) and (Go–Me) obtained from FIG. 26, the OPE index Q was calculated by the Equation (1). From P=(95.0+58.0)/83.0=1.8433, Q=−157.

Figure 27:
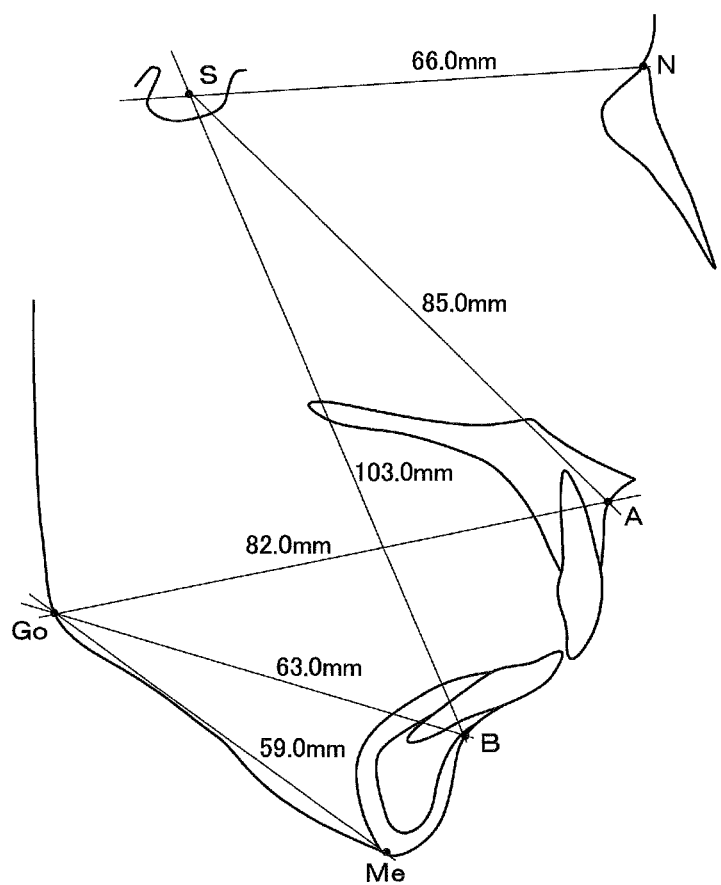
FIG. 27 A tracing made based on a cephalometric radiogram of the patient 15 after using the headgear for a long time further.

After using the headgear for 3 years and 2 months more, a cephalometric radiogram of the patient 15 was taken. A tracing made based on the cephalometric radiogram is shown in FIG. 27. From FIG. 27, (S–N)=66.0 mm, (S–A)=85.0 mm and (Go–A)=82.0 mm. Using the data, the calculation of P is given as follows: (85.0+82.0)/66.0=2.5303. Therefore, the index Q for hypogrowth of the maxilla is 530, so it is understood that the maxilla shows an overgrowth tendency. Using the distances (S–A), (S–B) and (Go–Me) obtained from FIG. 27, the OPE index Q was calculated by the Equation (1). From P=(103.0+59.0)/85.0=1.9058, Q=−95.

Example 40

Figure 28:
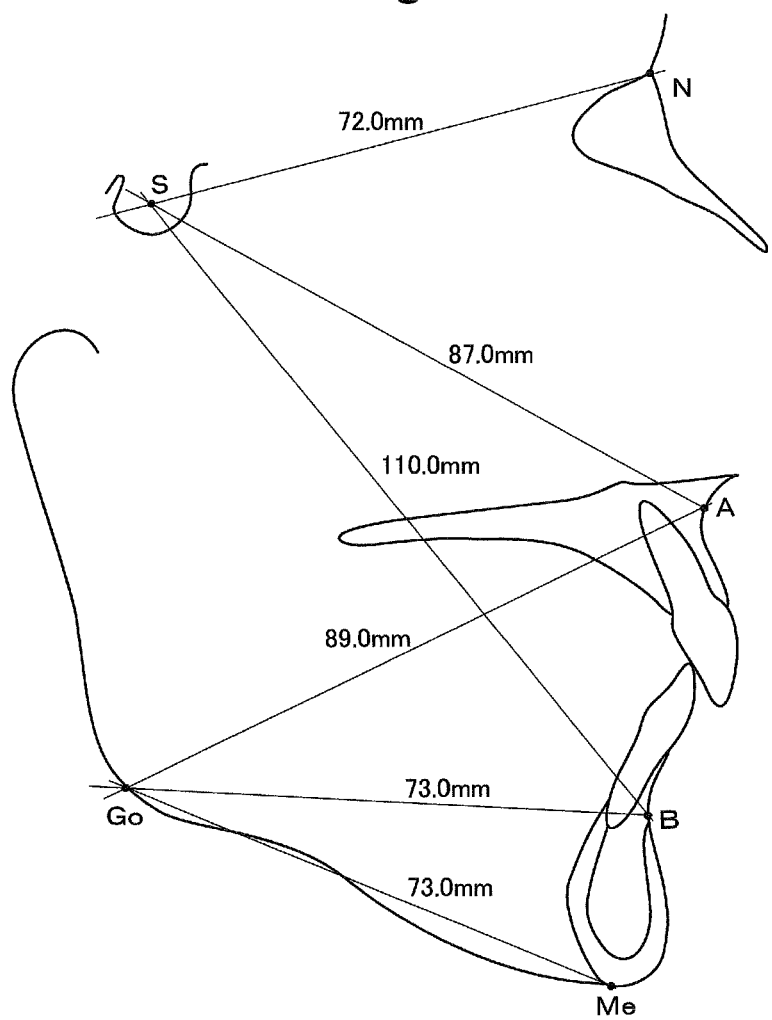
FIG. 28 A tracing made based on a cephalometric radiogram of a patient 16.

A cephalometric radiogram of a patient 16 was taken. A tracing made based on the cephalometric radiogram is shown in FIG. 28. From FIG. 28, (S–N)=72.0 mm, (S–A)=87.0 mm and (Go–A)=89.0 mm. Using the data, the calculation of P is given as follows: (87.0+89.0)/72.0=2.4444. Therefore, the index Q for hypogrowth of the maxilla is 444, and the patient 16 can be decided that the maxilla is normal. Using the distances (S–A), (S–B) and (Go–Me) obtained from FIG. 28, the OPE index Q was calculated by the Equation (1). From P=(110.0+73.0)/87.0=2.1034, Q=103.

Example 41

Figure 29:
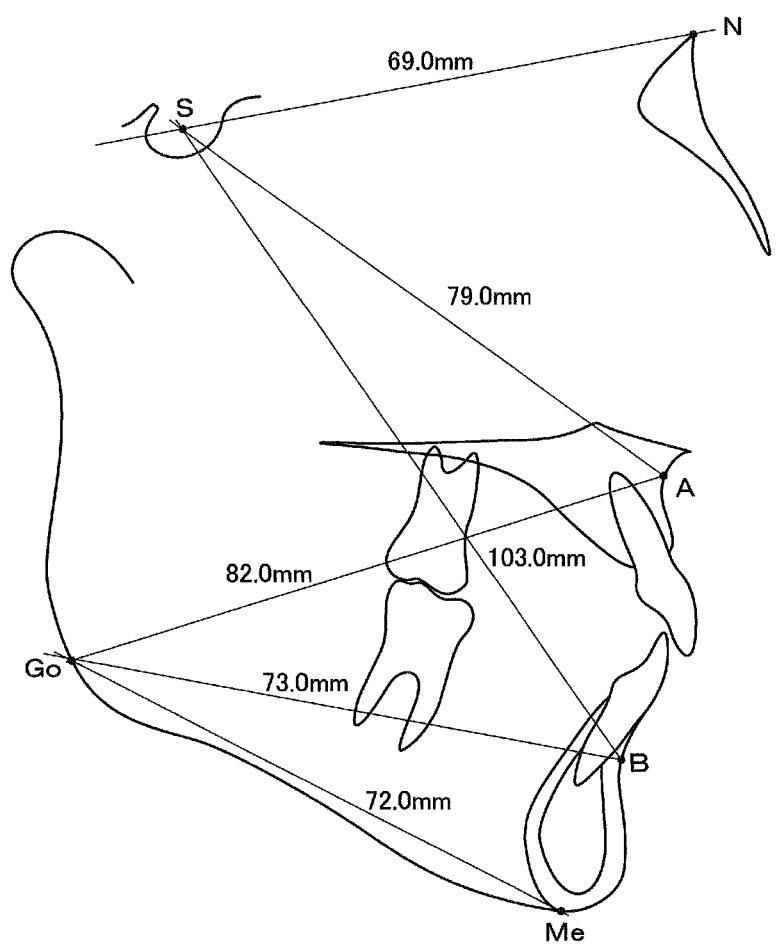
FIG. 29 A tracing made based on a cephalometric radiogram of a patient 17.

A cephalometric radiogram of a patient 17 was taken. A tracing made based on the cephalometric radiogram of the patient 17 is shown in FIG. 29. From FIG. 29, (S–N)=69.0 mm, (S–A)=79.0 mm and (Go–A)=82.0 mm. Using the data, the calculation of P is given as follows: (79.0+82.0)/69.0=2.3333. Therefore, the index Q for hypogrowth of the maxilla is 333, and the patient 17 can be decided that the maxilla is normal. Using the distances (S–A), (S–B) and (Go–Me) obtained from FIG. 29, the OPE index Q was calculated by the Equation (1). From P=(103.0+72.0)/79.0=2.2151, Q=215.

Example 42

Figure 30:
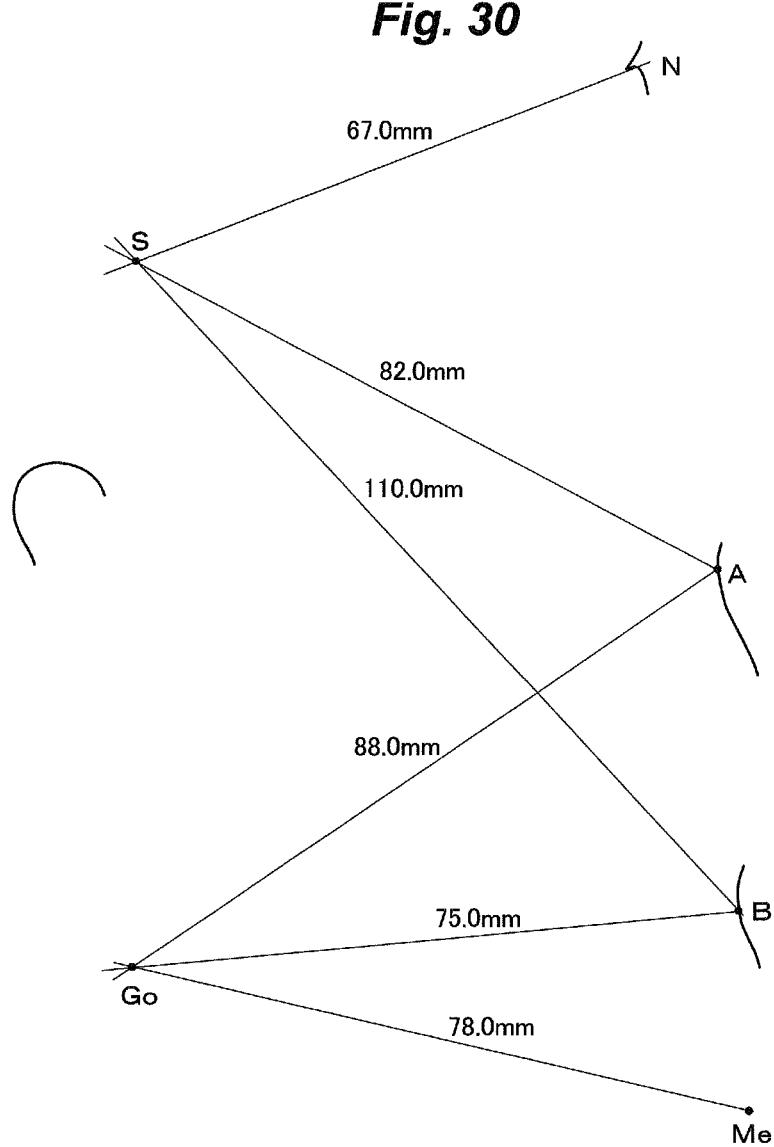
FIG. 30 A tracing made based on a cephalometric radiogram of a patient 18.

A cephalometric radiogram of a patient 18 was taken. A tracing made based on the cephalometric radiogram is shown in FIG. 30. From FIG. 30, (S–N)=67.0 mm, (S–A)=82.0 mm and (Go–A)=88.0 mm. Using the data, the calculation of P is given as follows: (82.0+88.0)/67.0=2.5373. Therefore, the index Q for hypogrowth of the maxilla is 537, and the patient 18 can be decided that there is overgrowth of the maxilla. Using the distances (S–A), (S–B) and (Go–Me) obtained from FIG. 30, the OPE index Q was calculated by the Equation (1). From P=(110.0+78.0)/82.0=2.2926, Q=292.

Example 43

Figure 31:
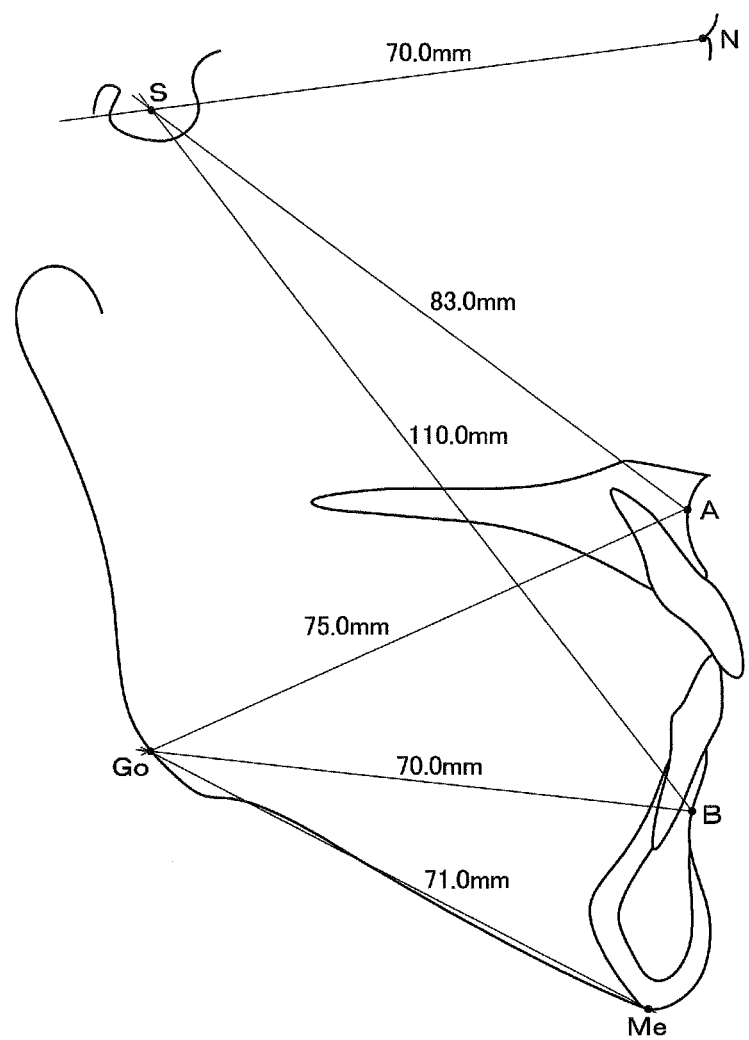
FIG. 31 A tracing made based on a cephalometric radiogram of a patient 19.

A cephalometric radiogram of a patient 19 was taken. A tracing made based on the cephalometric radiogram is shown in FIG. 31. From FIG. 31, (S–N)=70.0 mm, (S–A)=83.0 mm and (Go–A)=75.0 mm. Using the data, the calculation of P is given as follows: (83.0+75.0)/70.0=2.2571. Therefore, the index Q for hypogrowth of the maxilla is 257, and the patient 19 can be decided that the maxilla is normal. Using the distances (S–A), (S–B) and (Go–Me) obtained from FIG. 31, the OPE index Q was calculated by the Equation (1). From P=(110.0+71.0)/83.0=2.1807, Q=180.

Example 44

Figure 32:
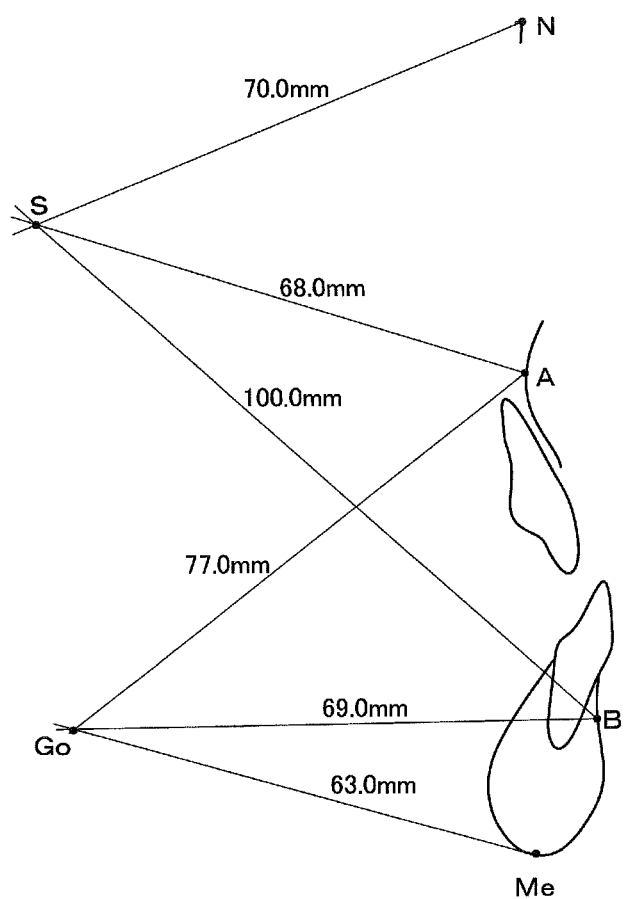
FIG. 32 A tracing made based on a cephalometric radiogram of a patient 20.

A cephalometric radiogram of a patient 20 was taken. A tracing made based on the cephalometric radiogram is shown in FIG. 32. From FIG. 32, (S–N)=70.0 mm, (S–A)=68.0 mm and (Go–A)=77.0 mm. Using the data, the calculation of P is given as follows: (68.0+77.0)/70.0=2.0714. Therefore, the index Q for hypogrowth of the maxilla is 71, and the patient 20 can be decided that there is serious hypogrowth of the maxilla. Using the distances (S–A), (S–B) and (Go–Me) obtained from FIG. 32, the OPE index Q was calculated by the Equation (1). From P=(100.0+63.0)/68.0=2.3970, Q=397.

Example 45

Figure 33:
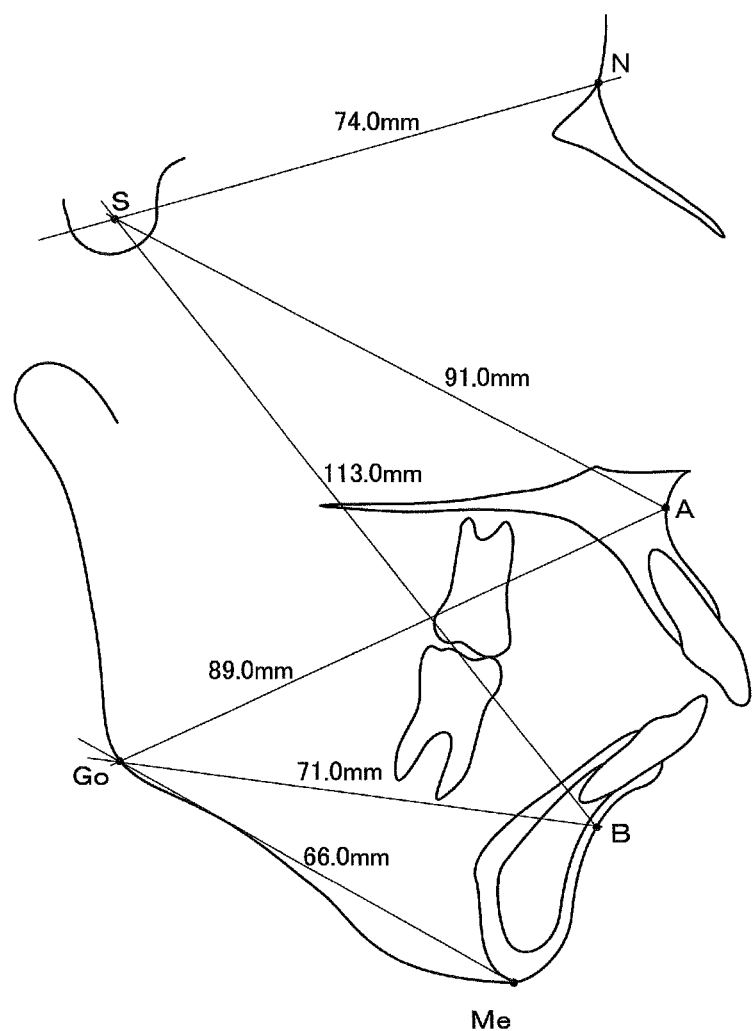
FIG. 33 A tracing made based on a cephalometric radiogram of a patient 21.

A cephalometric radiogram of a patient 21 was taken. A tracing made based on the cephalometric radiogram is shown in FIG. 33. From FIG. 33, (S–N)=74.0 mm, (S–A)=91.0 mm and (Go–A)=89.0 mm. Using the data, the calculation of P is given as follows: (91.0+89.0)/74.0=2.4324. Therefore, the index Q for hypogrowth of the maxilla is 432, and the patient 21 can be decided that the maxilla is normal. Using the distances (S–A), (S–B) and (Go–Me) obtained from FIG. 33, the OPE index Q was calculated by the Equation (1). From P=(113.0+66.0)/91.0=1.9670, Q=–32.

As explained, according to the method of calculating an index for hypogrowth of the maxilla of the thirteenth embodiment, using the distances (S–N), (S–A) and (Go–A) which are measured by cephalometric radiography, the index Q for hypogrowth of the maxilla can be calculated. And based on the index Q for hypogrowth of the maxilla, the presence or absence or the degree of hypogrowth of the maxilla or overgrowth of the maxilla can be decided without being influenced by the experience of a dentist or a doctor, and decided correctly with a short period of time, moreover with a certain objectivity.

14. Fourteenth Embodiment

In the fourteenth embodiment, a method of calculating an index for hypogrowth of the maxilla is explained.

Before calculating, a cephalometric radiogram of a patient is taken, and the distances (S–N) and (S–A) are measured. These distances can be measured by the method which was explained before.

At first, in step S71, the distances (S–N) and (S–A) which are measured by the above are entered.

In step S72, from the entered (S–N) and (S–A), P is calculated according to $$P = (S-A)/(S-N). \tag{18}$$

In step S73, from P obtained by the calculation of the above, omitting the figures of the fourth decimal place and under of P, in case of 1.000≤P<2.000, the index Q for hypogrowth of the maxilla is calculated according to $$Q = (P - [P]) \times 1000$$

and in case of P<1.000, the index Q for hypogrowth of the maxilla is calculated according to $$Q = (P - ([P]+1)) \times 1000.$$

In step S74, the index Q for hypogrowth of the maxilla calculated as the above is output on a display, for example.

From the index Q for hypogrowth of the maxilla calculated as the above, the presence or absence or the degree of hypogrowth of the maxilla or overgrowth of the maxilla can be decided objectively.

Example 46

From FIG. 3 showing the tracing made based on the cephalometric radiogram of the patient 1 taken in the example 1, the distances (S–N) and (S–A) were measured. The results are: (S–N)=67.0 mm and (S–A)=78.0 mm. Using the data, the calculation of P is given as follows: 78.0/67.0=1.1641. Therefore, the index Q for hypogrowth of the maxilla is 164.

From FIG. 4 showing the tracing made based on the cephalometric radiogram of the patient 1 after the severing operation on the mandible taken in the example 1, the distances (S–N) and (S–A) were measured. The results are: (S–N)=67.0 mm and (S–A)=78.0 mm. Using the data, the calculation of P is given as follows: 78.0/67.0=1.1641. Therefore, the index Q for hypogrowth of the maxilla is 164.

Example 47

From FIG. 5 showing the tracing made based on the cephalometric radiogram of the patient 2 taken in the example 2, the distances (S–N) and (S–A) were measured. The results are: (S–N)=69.0 mm and (S–A)=83.0 mm. Using the data, the calculation of P is given as follows: 83.0/69.0=1.2028. Therefore, the index Q for hypogrowth of the maxilla is 202.

From FIG. 6 showing the tracing made based on the cephalometric radiogram of the patient 2 after the severing operation on the mandible, the distances (S–N) and (S–A) were measured. The results are: (S–N)=69.0 mm and (S–A)=83.0 mm. Using the data, the calculation of P is given as follows: 83.0/69.0=1.2028. Therefore, the index Q for hypogrowth of the maxilla is 202.

Example 48

From FIG. 7 showing the tracing made based on the cephalometric radiogram of the patient 3 taken in the example 3, the distances (S–N) and (S–A) were measured. The results are: (S–N)=67.0 mm and (S–A)=88.0 mm. Using the data, the calculation of P is given as follows: 88.0/67.0=1.3134. Therefore, the index Q for hypogrowth of the maxilla is 313.

Example 49

From FIG. 8 showing the tracing made based on the cephalometric radiogram of the patient 4 taken in the example 4, the distances (S–N) and (S–A) were measured. The results are: (S–N)=64.0 mm and (S–A)=85.0 mm. Using the data, the calculation of P is given as follows: 85.0/64.0=1.3281. Therefore, the index Q for hypogrowth of the maxilla is 328.

Example 50

From FIG. 9 showing the tracing made based on the cephalometric radiogram of the patient 5 taken in the example 5, the distances (S–N) and (S–A) were measured. The results are: (S–N)=65.0 mm and (S–A)=75.0 mm. Using the data, the calculation of P is given as follows: 75.0/65.0=1.1538. Therefore, the index Q for hypogrowth of the maxilla is 153.

Example 51

From FIG. 10 showing the tracing made based on the cephalometric radiogram of the patient 6 taken in the example 6, the distances (S–N) and (S–A) were measured. The results are: (S–N)=68.0 mm and (S–A)=87.0 mm. Using the data, the calculation of P is given as follows: 87.0/68.0=1.2794. Therefore, the index Q for hypogrowth of the maxilla is 279.

From FIG. 11 showing the tracing made based on the cephalometric radiogram of the patient 6 after the severing operation on the mandible, the distances (S–N) and (S–A) were measured. The results are: (S–N)=68.0 mm and (S–A)=87.0 mm. Using the data, the calculation of P is given as follows: 87.0/68.0=1.2794. Therefore, the index Q for hypogrowth of the maxilla is 279.

Example 52

From FIG. 12 showing the tracing made based on the cephalometric radiogram of the patient 7 taken in the example 7, the distances (S–N) and (S–A) were measured. The results are: (S–N)=67.0 mm and (S–A)=86.0 mm. Using the data, the calculation of P is given as follows: 86.0/67.0=1.2835. Therefore, the index Q for hypogrowth of the maxilla is 283.

Example 53

From FIG. 13 showing the tracing made based on the cephalometric radiogram of the patient 8 taken in the example 8, the distances (S–N) and (S–A) were measured. The results are: (S–N)=68.0 mm and (S–A)=90.0 mm. Using the data, the calculation of P is given as follows: 90.0/68.0=1.3235. Therefore, the index Q for hypogrowth of the maxilla is 323.

Example 54

From FIG. 14 showing the tracing made based on the cephalometric radiogram of the patient 9 taken in the example 9, the distances (S–N) and (S–A) were measured. The results are: (S–N)=68.0 mm and (S–A)=79.0 mm. Using the data, the calculation of P is given as follows: 79.0/68.0=1.1617. Therefore, the index Q for hypogrowth of the maxilla is 161.

Example 55

From FIG. 15 showing the tracing made based on the cephalometric radiogram of the patient 10 taken in the example 10, the distances (S–N) and (S–A) were measured. The results are: (S–N)=69.0 mm and (S–A)=81.0 mm. Using the data, the calculation of P is given as follows: 81.0/69.0=1.1739. Therefore, the index Q for hypogrowth of the maxilla is 173.

Example 56

From FIG. 16 showing the tracing made based on the cephalometric radiogram of the patient 11 taken in the example 11, the distances (S–N) and (S–A) were measured. The results are: (S–N)=63.0 mm and (S–A)=81.0 mm. Using the data, the calculation of P is given as follows: 81.0/63.0=1.2857. Therefore, the index Q for hypogrowth of the maxilla is 285.

Example 57

From FIG. 17 showing the tracing made based on the cephalometric radiogram of the patient 12 taken in the example 12, the distances (S–N) and (S–A) were measured. The results are: (S–N)=74.0 mm and (S–A)=91.0 mm. Using the data, the calculation of P is given as follows: 91.0/74.0=1.2297. Therefore, the index Q for hypogrowth of the maxilla is 229.

As explained, according to the method of calculating an index for hypogrowth of the maxilla of the fourteenth embodiment, using the distances (S–N) and (S–A) which are measured by cephalometric radiography, the index Q for hypogrowth of the maxilla can be calculated. And based on the index Q for hypogrowth of the maxilla, the presence or absence or the degree of hypogrowth of the maxilla or overgrowth of the maxilla can be decided without being influenced by the experience of a dentist or a doctor, and decided correctly with a short period of time, moreover with a certain objectivity.

15. Fifteenth Embodiment

In the fifteenth embodiment, a method of calculating an index for hypogrowth of the maxilla is explained.

Before calculating, a cephalometric radiogram of a patient is taken, and the distances (S–N) and (S–A) are measured. These distances can be measured by the method which was explained before.

At first, in step S81, the distances (S–N) and (S–A) which are measured by the above are entered.

In step S82, from the entered (S–N) and (S–A), P is calculated according to $$P=(S-A)-(S-N). \tag{19}$$

In step S83, the index P for hypogrowth of the maxilla calculated as the above is output on a display, for example.

From the index P for hypogrowth of the maxilla calculated as the above, the presence or absence or the degree of hypogrowth of the maxilla or overgrowth of the maxilla can be decided objectively.

Example 58

From FIG. 3 showing the tracing made based on the cephalometric radiogram of the patient 1 taken in the example 1, the distances (S–N) and (S–A) were measured. The results are: (S–N)=67.0 mm and (S–A)=78.0 mm. Using the data, the calculation of P is given as follows: 78.0−67.0=11 mm. Therefore, the index P for hypogrowth of the maxilla is 11 mm.

From FIG. 4 showing the tracing made based on the cephalometric radiogram of the patient 1 after the severing operation on the mandible taken in the example 1, the distances (S–N) and (S–A) were measured. The results are: (S–N)= 67.0 mm and (S–A)=78.0 mm. Using the calculation of P is given as follows: 78.0−67.0=11 mm. Therefore, the index P for hypogrowth of the maxilla is 11 mm.

Example 59

From FIG. 5 showing the tracing made based on the cephalometric radiogram of the patient 2 taken in the example 2, the distances (S−N) and (S−A) were measured. The results are: (S−N)=69.0 mm and (S−A)=83.0 mm. Using the data, the calculation of P is given as follows: 83.0−69.0=14 mm. Therefore, the index P for hypogrowth of the maxilla is 14 mm.

From FIG. 6 showing the tracing made based on the cephalometric radiogram of the patient 2 after the severing operation on the mandible, the distances (S−N) and (S−A) were measured. The results are: (S−N)=69.0 mm and (S−A)=83.0 mm. Using the data, the calculation of P is given as follows: 83.0−69.0=14 mm. Therefore, the index P for hypogrowth of the maxilla is 14 mm.

Example 60

From FIG. 7 showing the tracing made based on the cephalometric radiogram of the patient 3 taken in the example 3, the distances (S−N) and (S−A) were measured. The results are: (S−N)=67.0 mm and (S−A)=88.0 mm. Using the data, the calculation of P is given as follows: 88.0−67.0=21 mm. Therefore, the index P for hypogrowth of the maxilla is 21 mm.

Example 61

From FIG. 8 showing the tracing made based on the cephalometric radiogram of the patient 4 taken in the example 4, the distances (S−N) and (S−A) were measured. The results are: (S−N)=64.0 mm and (S−A)=85.0 mm. Using the data, the calculation of P is given as follows: 85.0−64.0=21 mm. Therefore, the index P for hypogrowth of the maxilla is 21 mm.

Example 62

From FIG. 9 showing the tracing made based on the cephalometric radiogram of the patient 5 taken in the example 5, the distances (S−N) and (S−A) were measured. The results are: (S−N)=65.0 mm and (S−A)=75.0 mm. Using the data, the calculation of P is given as follows: 75.0−65.0=10 mm. Therefore, the index P for hypogrowth of the maxilla is 10 mm.

Example 63

From FIG. 10 showing the tracing made based on the cephalometric radiogram of the patient 6 taken in the example 6, the distances (S−N) and (S−A) were measured. The results are: (S−N)=68.0 mm and (S−A)=87.0 mm. Using the data, the calculation of P is given as follows: 87.0−68.0=19 mm. Therefore, the index P for hypogrowth of the maxilla is 19 mm.

From FIG. 11 showing the tracing made based on the cephalometric radiogram of the patient 6 after the severing operation on the mandible, the distances (S−N) and (S−A) were measured. The results are: (S−N)=68.0 mm and (S−A)=87.0 mm. Using the data, the calculation of P is given as follows: 87.0−68.0=19 mm. Therefore, the index P for hypogrowth of the maxilla is 19 mm.

Example 64

From FIG. 12 showing the tracing made based on the cephalometric radiogram of the patient 7 taken in the example 7, the distances (S−N) and (S−A) were measured. The results are: (S−N)=67.0 mm and (S−A)=86.0 mm. Using the data, the calculation of P is given as follows: 86.0−67.0=19 mm. Therefore, the index P for hypogrowth of the maxilla is 19 mm.

Example 65

From FIG. 13 showing the tracing made based on the cephalometric radiogram of the patient 8 taken in the example 8, the distances (S−N) and (S−A) were measured. The results are: (S−N)=68.0 mm and (S−A)=90.0 mm. Using the data, the calculation of P is given as follows: 90.0−68.0=22 mm. Therefore, the index P for hypogrowth of the maxilla is 22 mm.

Example 66

From FIG. 14 showing the tracing made based on the cephalometric radiogram of the patient 9 taken in the example 9, the distances (S−N) and (S−A) were measured. The results are: (S−N)=68.0 mm and (S−A)=79.0 mm. Using the data, the calculation of P is given as follows: 79.0−68.0=11 mm. Therefore, the index P for hypogrowth of the maxilla is 11 mm.

Example 67

From FIG. 15 showing the tracing made based on the cephalometric radiogram of the patient 10 taken in the example 10, the distances (S−N) and (S−A) were measured. The results are: (S−N)=69.0 mm and (S−A)=81.0 mm. Using the data, the calculation of P is given as follows: 81.0−69.0=12 mm. Therefore, the index P for hypogrowth of the maxilla is 12 mm.

Example 68

From FIG. 16 showing the tracing made based on the cephalometric radiogram of the patient 11 taken in the example 11, the distances (S−N) and (S−A) were measured. The results are: (S−N)=63.0 mm and (S−A)=81.0 mm. Using the data, the calculation of P is given as follows: 81.0−63.0=18 mm. Therefore, the index P for hypogrowth of the maxilla is 18 mm.

Example 69

From FIG. 17 showing the tracing made based on the cephalometric radiogram of the patient 12 taken in the example 12, the distances (S−N) and (S−A) were measured. The results are: (S−N)=74.0 mm and (S−A)=91.0 mm. Using the data, the calculation of P is given as follows: 91.0−74.0=17 mm. Therefore, the index P for hypogrowth of the maxilla is 17 mm.

As explained, according to the method of calculating an index for hypogrowth of the maxilla of the fifteenth embodiment, using the distances (S−N) and (S−A) which are measured by cephalometric radiography, the index P for hypogrowth of the maxilla can be calculated. And based on the index P for hypogrowth of the maxilla, the presence or absence or the degree of hypogrowth of the maxilla or overgrowth of the maxilla can be decided without being influenced by the experience of a dentist or a doctor, and decided correctly with a short period of time, moreover with a certain objectivity.

16. Sixteenth Embodiment

In the sixteenth embodiment, a method of calculating an index for hypogrowth of the mandible is explained.

Before calculating, a cephalometric radiogram of a patient is taken, and the distances (S–N), (S–A), (S–B), (Go–B) and (Go–Me) are measured. These distances can be measured by the method which was explained before.

At first, in step S91, the distances (S–N), (S–A), (S–B), (Go–B) and (Go–Me) which are measured by the above are entered.

In step S92, from the entered (S–N), (S–A), (S–B), (Go–B) and (Go–Me), P is calculated according to $$P=((S-B)+(Go-B)+(Go-Me))/((S-N)+(S-A)). \quad (20)$$

In step S93, from P obtained by the calculation of the above, omitting the figures of the fourth decimal place and under of P, in case of $1.000 \leq P < 2.000$, the index Q for hypogrowth of the mandible is calculated according to $$Q=(P-[P]) \times 1000$$

and in case of P<1.000, the index Q for hypogrowth of the mandible is calculated according to $$Q=(P-([P]+1)) \times 1000.$$

In step S94, the index Q for hypogrowth of the mandible calculated as the above is output on a display, for example.

From the index Q for hypogrowth of the mandible calculated as the above, the presence or absence or the degree of hypogrowth of the mandible or overgrowth of the mandible can be decided objectively.

Example 70

From FIG. 3 showing the tracing made based on the cephalometric radiogram of the patient 1 taken in the example 1, the distances (S–N), (S–A), (S–B), (Go–B) and (Go–Me) were measured. The results are: (S–N)=67.0 mm, (S–A)=78.0 mm, (S–B)=123 mm, (Go–B)=78.0 mm and (Go–Me)=78.0 mm. Using the data, the calculation of P is given as follows: (123.0+78.0+78.0)/(67.0+78.0)=1.9241. Therefore, the index Q for hypogrowth of the mandible is 924.

From FIG. 4 showing the tracing made based on the cephalometric radiogram of the patient 1 after the severing operation on the mandible taken in the example 1, the distances (S–N), (S–A), (S–B), (Go–B) and (Go–Me) were measured. The results are: (S–N)=67.0 mm, (S–A)=78.0 mm, (S–B)=111 mm, (Go–B)=73.0 mm and (Go–Me)=73.0 mm. Using the data, the calculation of P is given as follows: (111.0+73.0+73.0)/(67.0+78.0)=1.7724. Therefore, the index Q for hypogrowth of the mandible is 772.

Example 71

From FIG. 5 showing the tracing made based on the cephalometric radiogram of the patient 2 taken in the example 2, the distances (S–N), (S–A), (S–B), (Go–B) and (Go–Me) were measured. The results are: (S–N)=69.0 mm, (S–A)=83.0 mm, (S–B)=123 mm, (Go–B)=80.0 mm and (Go–Me)=81.0 mm. Using the data, the calculation of P is given as follows: (123.0+80.0+81.0)/(69.0+83.0)=1.8684. Therefore, the index Q for hypogrowth of the mandible is 868.

From FIG. 6 showing the tracing made based on the cephalometric radiogram of the patient 2 after the severing operation on the mandible, the distances (S–N), (S–A), (S–B), (Go–B) and (Go–Me) were measured. The results are: (S–N)=69.0 mm, (S–A)=83.0 mm, (S–B)=116 mm, (Go–B)=80.0 mm and (Go–Me)=80.0 mm. Using the data, the calculation of P is given as follows: (116.0+80.0+80.0)/(69.0+83.0)=1.8157. Therefore, the index Q for hypogrowth of the mandible is 815.

Example 72

From FIG. 7 showing the tracing made based on the cephalometric radiogram of the patient 3 taken in the example 3, the distances (S–N), (S–A), (S–B), (Go–B) and (Go–Me) were measured. The results are: (S–N)=67.0 mm, (S–A)=88.0 mm, (S–B)=126.0 mm, (Go–B)=80.0 mm and (Go–Me)=78.0 mm. Using the data, the calculation of P is given as follows: (126.0+80.0+78.0)/(67.0+88.0)=1.8322. Therefore, the index Q for hypogrowth of the mandible is 832.

Example 73

From FIG. 8 showing the tracing made based on the cephalometric radiogram of the patient 4 taken in the example 4, the distances (S–N), (S–A), (S–B), (Go–B) and (Go–Me) were measured. The results are: (S–N)=64.0 mm, (S–A)=85.0 mm, (S–B)=119.0 mm, (Go–B)=76.0 mm and (Go–Me)=77.0 mm. Using the data, the calculation of P is given as follows: (119.0+76.0+77.0)/(64.0+85.0)=1.8255. Therefore, the index Q for hypogrowth of the mandible is 825.

Example 74

From FIG. 9 showing the tracing made based on the cephalometric radiogram of the patient 5 taken in the example 5, the distances (S–N), (S–A), (S–B), (Go–B) and (Go–Me) were measured. The results are: (S–N)=65.0 mm, (S–A)=75.0 mm, (S–B)=109.0 mm, (Go–B)=73.0 mm and (Go–Me)=70.0 mm. Using the data, the calculation of P is given as follows: (109.0+73.0+70.0)/(65.0+75.0)=1.8000. Therefore, the index Q for hypogrowth of the mandible is 800.

Example 75

From FIG. 10 showing the tracing made based on the cephalometric radiogram of the patient 6 taken in the example 6, the distances (S–N), (S–A), (S–B), (Go–B) and (Go–Me) were measured. The results are: (S–N)=68.0 mm, (S–A)=87.0 mm, (S–B)=128.0 mm, (Go–B)=80.0 mm and (Go–Me)=80.0 mm. Using the data, the calculation of P is given as follows: (128.0+80.0+80.0)/(68.0+87.0)=1.8580. Therefore, the index Q for hypogrowth of the mandible is 858.

From FIG. 11 showing the tracing made based on the cephalometric radiogram of the patient 6 after the severing operation on the mandible, the distances (S–N), (S–A), (S–B), (Go–B) and (Go–Me) were measured. The results are: (S–N)=68.0 mm, (S–A)=87.0 mm, (S–B)=121.0 mm, (Go–B)=73.0 mm and (Go–Me)=73.0 mm. Using the data, the calculation of P is given as follows: (121.0+73.0+73.0)/(68.0+87.0)=1.7225. Therefore, the index Q for hypogrowth of the mandible is 722.

Example 76

From FIG. 12 showing the tracing made based on the cephalometric radiogram of the patient 7 taken in the example 7, the distances (S–N), (S–A), (S–B), (Go–B) and (Go–Me) were measured. The results are: (S–N)=67.0 mm, (S–A)=

86.0 mm, (S–B)=111.0 mm, (Go–B)=73.0 mm and (Go–Me)=69.0 mm. Using the data, the calculation of P is given as follows: (111.0+73.0+69.0)/(67.0+86.0)=1.6535. Therefore, the index Q for hypogrowth of the mandible is 653.

Example 77

From FIG. 13 showing the tracing made based on the cephalometric radiogram of the patient 8 taken in the example 8, the distances (S–N), (S–A), (S–B), (Go–B) and (Go–Me) were measured. The results are: (S–N)=68.0 mm, (S–A)=90.0 mm, (S–B)=127.0 mm, (Go–B)=80.0 mm and (Go–Me)=80.0 mm. Using the data, the calculation of P is given as follows: (127.0+80.0+80.0)/(68.0+90.0)=1.8164. Therefore, the index Q for hypogrowth of the mandible is 816.

Example 78

From FIG. 14 showing the tracing made based on the cephalometric radiogram of the patient 9 taken in the example 9, the distances (S–N), (S–A), (S–B), (Go–B) and (Go–Me) were measured. The results are: (S–N)=68.0 mm, (S–A)=79.0 mm, (S–B)=105.0 mm, (Go–B)=74.0 mm and (Go–Me)=73.0 mm. Using the data, the calculation of P is given as follows: (105.0+74.0+73.0)/(68.0+79.0)=1.7142. Therefore, the index Q for hypogrowth of the mandible is 714.

Example 79

From FIG. 15 showing the tracing made based on the cephalometric radiogram of the patient 10 taken in the example 10, the distances (S–N), (S–A), (S–B), (Go–B) and (Go–Me) were measured. The results are: (S–N)=69.0 mm, (S–A)=81.0 mm, (S–B)=103.0 mm, (Go–B)=72.0 mm and (Go–Me)=70.0 mm. Using the data, the calculation of P is given as follows: (103.0+72.0+70.0)/(69.0+81.0)=1.6333. Therefore, the index Q for hypogrowth of the mandible is 633.

Example 80

From FIG. 16 showing the tracing made based on the cephalometric radiogram of the patient 11 taken in the example 11, the distances (S–N), (S–A), (S–B), (Go–B) and (Go–Me) were measured. The results are: (S–N)=63.0 mm, (S–A)=81.0 mm, (S–B)=108.0 mm, (Go–B)=69.0 mm and (Go–Me)=68.0 mm. Using the data, the calculation of P is given as follows: (108.0+69.0+68.0)/(63.0+81.0)=1.7013. Therefore, the index Q for hypogrowth of the mandible is 701.

Example 81

From FIG. 17 showing the tracing made based on the cephalometric radiogram of the patient 12 taken in the example 12, the distances (S–N), (S–A), (S–B), (Go–B) and (Go–Me) were measured. The results are: (S–N)=74.0 mm, (S–A)=91.0 mm, (S–B)=115.0 mm, (Go–B)=70.0 mm and (Go–Me)=65.0 mm. Using the data, the calculation of P is given as follows: (115.0+70.0+65.0)/(74.0+91.0)=1.5151. Therefore, the index Q for hypogrowth of the mandible is 515.

As explained, according to the method of calculating an index for hypogrowth of the mandible of the sixteenth embodiment, using the distances (S–N), (S–A), (S–B), (Go–B) and (Go–Me) which are measured by cephalometric radiography, the index Q for hypogrowth of the mandible can be calculated. And based on the index Q for hypogrowth of the mandible, the presence or absence or the degree of hypogrowth of the mandible or overgrowth of the mandible can be decided without being influenced by the experience of a dentist or a doctor, and decided correctly with a short period of time, moreover with a certain objectivity.

17. Seventeenth Embodiment

In the seventeenth embodiment, a method of calculating an index for hypogrowth of the mandible is explained.

Before calculating, a cephalometric radiogram of a patient is taken, and the distances (S–N), (S–A), (S–B) and (Go–B) are measured. These distances can be measured by the method which was explained before.

At first, in step S101, the distances (S–N), (S–A), (S–B) and (Go–B) which are measured by the above are entered.

In step S102, from the entered (S–N), (S–A), (S–B) and (Go–B), P is calculated according to $$P = ((S-B) + (Go-B))/((S-N) + (S-A)). \quad (21)$$

In step S103, from P obtained by the calculation of the above, omitting the figures of the fourth decimal place and under of P, in case of 1.000≤P<2.000, the index Q for hypogrowth of the mandible is calculated according to $$Q = (P - [P]) \times 1000$$

and in case of P<1.000, the index Q for hypogrowth of the mandible is calculated according to $$Q = (P - ([P]+1)) \times 1000.$$

In step S104, the index Q for hypogrowth of the mandible calculated as the above is output on a display, for example.

From the index Q for hypogrowth of the mandible calculated as the above, the presence or absence or the degree of hypogrowth or overgrowth of the mandible can be decided objectively.

Example 82

From FIG. 3 showing the tracing made based on the cephalometric radiogram of the patient 1 taken in the example 1, the distances (S–N), (S–A), (S–B) and (Go–B) were measured. The results are: (S–N)=67.0 mm, (S–A)=78.0 mm, (S–B)=123 mm and (Go–B)=78.0 mm. Using the data, the calculation of P is given as follows: (123.0+78.0)/(67.0+78.0)=1.3862. Therefore, the index Q for hypogrowth of the mandible is 386.

From FIG. 4 showing the tracing made based on the cephalometric radiogram of the patient 1 after the severing operation on the mandible taken in the example 1, the distances (S–N), (S–A), (S–B) and (Go–B) were measured. The results are: (S–N)=67.0 mm, (S–A)=78.0 mm, (S–B)=111 mm and (Go–B)=73.0 mm. Using the data, the calculation of P is given as follows: (111.0+73.0)/(67.0+78.0)=1.2689. Therefore, the index Q for hypogrowth of the mandible is 268.

Example 83

From FIG. 5 showing the tracing made based on the cephalometric radiogram of the patient 2 taken in the example 2, the distances (S–N), (S–A), (S–B) and (Go–B) were measured. The results are: (S–N)=69.0 mm, (S–A)=83.0 mm, (S–B)=123 mm and (Go–B)=80.0 mm. Using the data, the calculation of P is given as follows: (123.0+80.0)/(69.0+83.0)=1.3355. Therefore, the index Q for hypogrowth of the mandible is 335.

From FIG. 6 showing the tracing made based on the cephalometric radiogram of the patient 2 after the severing operation on the mandible, the distances (S–N), (S–A), (S–B) and (Go–B) were measured. The results are: (S–N)=69.0 mm, (S–A)=83.0 mm, (S–B)=116 mm and (Go–B)=80.0 mm. Using the data, the calculation of P is given as follows: (116.0+80.0)/(69.0+83.0)=1.2894. Therefore, the index Q for hypogrowth of the mandible is 289.

Example 84

From FIG. 7 showing the tracing made based on the cephalometric radiogram of the patient 3 taken in the example 3, the distances (S–N), (S–A), (S–B) and (Go–B) were measured. The results are: (S–N)=67.0 mm, (S–A)=88.0 mm, (S–B)=126.0 mm, (Go–B)=80.0 mm. Using the data, the calculation of P is given as follows: (126.0+80.0)/(67.0+88.0)=1.3290. Therefore, the index Q for hypogrowth of the mandible is 329.

Example 85

From FIG. 8 showing the tracing made based on the cephalometric radiogram of the patient 4 taken in the example 4, the distances (S–N), (S–A), (S–B) and (Go–B) were measured. The results are: (S–N)=64.0 mm, (S–A)=85.0 mm, (S–B)=119.0 mm and (Go–B)=76.0 mm. Using the data, the calculation of P is given as follows: (119.0+76.0)/(64.0+85.0)=1.3087. Therefore, the index Q for hypogrowth of the mandible is 308.

Example 86

From FIG. 9 showing the tracing made based on the cephalometric radiogram of the patient 5 taken in the example 5, the distances (S–N), (S–A), (S–B) and (Go–B) were measured. The results are: (S–N)=65.0 mm, (S–A)=75.0 mm, (S–B)=109.0 mm and (Go–B)=73.0 mm. Using the data, the calculation of P is given as follows: (109.0+73.0)/(65.0+75.0)=1.3000. Therefore, the index Q for hypogrowth of the mandible is 300.

Example 87

From FIG. 10 showing the tracing made based on the cephalometric radiogram of the patient 6 taken in the example 6, the distances (S–N), (S–A), (S–B) and (Go–B) were measured. The results are: (S–N)=68.0 mm, (S–A)=87.0 mm, (S–B)=128.0 mm and (Go–B)=80.0 mm. Using the data, the calculation of P is given as follows: (128.0+80.0)/(68.0+87.0)=1.3419. Therefore, the index Q for hypogrowth of the mandible is 341.

From FIG. 11 showing the tracing made based on the cephalometric radiogram of the patient 6 after the severing operation on the mandible, the distances (S–N), (S–A), (S–B) and (Go–B) were measured. The results are: (S–N)=68.0 mm, (S–A)=87.0 mm, (S–B)=121.0 mm and (Go–B)=73.0 mm. Using the data, the calculation of P is given as follows: (121.0+73.0)/(68.0+87.0)=1.2516. Therefore, the index Q for hypogrowth of the mandible is 251.

Example 88

From FIG. 12 showing the tracing made based on the cephalometric radiogram of the patient 7 taken in the example 7, the distances (S–N), (S–A), (S–B) and (Go–B) were measured. The results are: (S–N)=67.0 mm, (S–A)=86.0 mm, (S–B)=111.0 mm and (Go–B)=73.0 mm. Using the data, the calculation of P is given as follows: (111.0+73.0)/(67.0+86.0)=1.2026. Therefore, the index Q for hypogrowth of the mandible is 202.

Example 89

From FIG. 13 showing the tracing made based on the cephalometric radiogram of the patient 8 taken in the example 8, the distances (S–N), (S–A), (S–B) and (Go–B) were measured. The results are: (S–N)=68.0 mm, (S–A)=90.0 mm, (S–B)=127.0 mm and (Go–B)=80.0 mm. Using the data, the calculation of P is given as follows: (127.0+80.0)/(68.0+90.0)=1.3101. Therefore, the index Q for hypogrowth of the mandible is 310.

Example 90

From FIG. 14 showing the tracing made based on the cephalometric radiogram of the patient 9 taken in the example 9, the distances (S–N), (S–A), (S–B) and (Go–B) were measured. The results are: (S–N)=68.0 mm, (S–A)=79.0 mm, (S–B)=105.0 mm and (Go–B)=74.0 mm. Using the data, the calculation of P is given as follows: (105.0+74.0)/(68.0+79.0)=1.2176. Therefore, the index Q for hypogrowth of the mandible is 217.

Example 91

From FIG. 15 showing the tracing made based on the cephalometric radiogram of the patient 10 taken in the example 10, the distances (S–N), (S–A), (S–B) and (Go–B) were measured. The results are: (S–N)=69.0 mm, (S–A)=81.0 mm, (S–B)=103.0 mm and (Go–B)=72.0 mm. Using the data, the calculation of P is given as follows: (103.0+72.0)/(69.0+81.0)=1.1666. Therefore, the index Q for hypogrowth of the mandible is 166.

Example 92

From FIG. 16 showing the tracing made based on the cephalometric radiogram of the patient 11 taken in the example 11, the distances (S–N), (S–A), (S–B) and (Go–B) were measured. The results are: (S–N)=63.0 mm, (S–A)=81.0 mm, (S–B)=108.0 mm and (Go–B)=69.0 mm. Using the data, the calculation of P is given as follows: (108.0+69.0)/(63.0+81.0)=1.2291. Therefore, the index Q for hypogrowth of the mandible is 229.

Example 93

From FIG. 17 showing the tracing made based on the cephalometric radiogram of the patient 12 taken in the example 12, the distances (S–N), (S–A), (S–B) and (Go–B) were measured. The results are: (S–N)=74.0 mm, (S–A)=91.0 mm, (S–B)=115.0 mm and (Go–B)=70.0 mm. Using the data, the calculation of P is given as follows: (115.0+70.0)/(74.0+91.0)=1.1212. Therefore, the index Q for hypogrowth of the mandible is 121.

As explained, according to the method of calculating an index for hypogrowth of the mandible of the seventeenth embodiment, using the distances (S–N), (S–A), (S–B) and (Go–B) which are measured by cephalometric radiography, the index Q for hypogrowth of the mandible can be calculated. And based on the index Q for hypogrowth of the mandible, the presence or absence or the degree of hypogrowth of the mandible or overgrowth of the mandible can be decided without being influenced by the experience of a dentist or a doctor, and decided correctly with a short period of time, moreover with a certain objectivity.

18. Eighteenth Embodiment

In the eighteenth embodiment, a method of calculating an index for hypogrowth of the mandible is explained.

Before calculating, a cephalometric radiogram of a patient is taken, and the distances (S–N), (S–B) and (Go–B) are measured. These distances can be measured by the method which was explained before.

At first, in step S111, the distances (S–N), (S–B) and (Go–B) which are measured by the above are entered.

In step S112, from the entered (S–N), (S–B) and (Go–B), P is calculated according to $$P=((S-B)+(Go-B))/(S-N). \tag{22}$$

In step S113, from P obtained by the calculation of the above, omitting the figures of the fourth decimal place and under of P, in case of 2.000≤P<3.000, the index Q for hypogrowth of the mandible is calculated according to $$Q=(P-[P])\times 1000$$

and in case of 3.000≤P<4.000, the index Q for hypogrowth of the mandible is calculated according to $$Q=(P-[P]+1)\times 1000.$$

In step S114, the index Q for hypogrowth of the mandible calculated as the above is output on a display, for example.

From the index Q for hypogrowth of the mandible calculated as the above, the presence or absence or the degree of hypogrowth of the mandible or overgrowth of the mandible can be decided objectively.

Example 94

From FIG. 3 showing the tracing made based on the cephalometric radiogram of the patient 1 taken in the example 1, the distances (S–N), (S–B) and (Go–B) were measured. The results are: (S–N)=67.0 mm, (S–B)=123 mm and (Go–B)=78.0 mm. Using the data, the calculation of P is given as follows: (123.0+78.0)/67.0=3.0000. Therefore, the index Q for hypogrowth of the mandible is 1000 and it can be decided that there is serious overgrowth of the mandible.

From FIG. 4 showing the tracing made based on the cephalometric radiogram of the patient 1 after the severing operation on the mandible taken in the example 1, the distances (S–N), (S–B) and (Go–B) were measured. The results are: (S–N)=67.0 mm, (S–B)=111 mm and (Go–B)=73.0 mm. Using the data, the calculation of P is given as follows: (111.0+73.0)/67.0=2.7462. Therefore, the index Q for hypogrowth of the mandible is 746 and it can be decided that the degree of overgrowth of the mandible was improved greatly.

Example 95

From FIG. 5 showing the tracing made based on the cephalometric radiogram of the patient 2 taken in the example 2, the distances (S–N), (S–B) and (Go–B) were measured. The results are: (S–N)=69.0 mm, (S–B)=123 mm and (Go–B)=80.0 mm. Using the data, the calculation of P is given as follows: (123.0+80.0)/69.0=2.9420. Therefore, the index Q for hypogrowth of the mandible is 942 and it can be decided that there is serious overgrowth of the mandible.

From FIG. 6 showing the tracing made based on the cephalometric radiogram of the patient 2 after the severing operation on the mandible, the distances (S–N), (S–B) and (Go–B) were measured. The results are: (S–N)=69.0 mm, (S–B)=116 mm and (Go–B)=80.0 mm. Using the data, the calculation of P is given as follows: (116.0+80.0)/69.0=2.8405. Therefore, the index Q for hypogrowth of the mandible is 840 and it can be decided that the degree of overgrowth of the mandible was improved.

Example 96

From FIG. 7 showing the tracing made based on the cephalometric radiogram of the patient 3 taken in the example 3, the distances (S–N), (S–B) and (Go–B) were measured. The results are: (S–N)=67.0 mm, (S–B)=126.0 mm and (Go–B)=80.0 mm. Using the data, the calculation of P is given as follows: (126.0+80.0)/67.0=3.0746. Therefore, the index Q for hypogrowth of the mandible is 1074 and it can be decided that there is serious overgrowth of the mandible.

Example 97

From FIG. 8 showing the tracing made based on the cephalometric radiogram of the patient 4 taken in the example 4, the distances (S–N), (S–B) and (Go–B) were measured. The results are: (S–N)=64.0 mm, (S–B)=119.0 mm and (Go–B)=76.0 mm. Using the data, the calculation of P is given as follows: (119.0+76.0)/64.0=3.0468. Therefore, the index Q for hypogrowth of the mandible is 1046 and it can be decided that there is serious overgrowth of the mandible.

Example 98

From FIG. 9 showing the tracing made based on the cephalometric radiogram of the patient 5 taken in the example 5, the distances (S–N), (S–B) and (Go–B) were measured. The results are: (S–N)=65.0 mm, (S–B)=109.0 mm and (Go–B)=73.0 mm. Using the data, the calculation of P is given as follows: (109.0+73.0)/65.0=2.8000. Therefore, the index Q for hypogrowth of the mandible is 800 and it can be decided that there is overgrowth of the mandible.

Example 99

From FIG. 10 showing the tracing made based on the cephalometric radiogram of the patient 6 taken in the example 6, the distances (S–N), (S–B) and (Go–B) were measured. The results are: (S–N)=68.0 mm, (S–B)=128.0 mm and (Go–B)=80.0 mm. Using the data, the calculation of P is given as follows: (128.0+80.0)/68.0=3.0588. Therefore, the index Q for hypogrowth of the mandible is 1058 and it can be decided that there is serious overgrowth of the mandible.

From FIG. 11 showing the tracing made based on the cephalometric radiogram of the patient 6 after the severing operation on the mandible, the distances (S–N), (S–B) and (Go–B) were measured. The results are: (S–N)=68.0 mm, (S–B)=121.0 mm and (Go–B)=73.0 mm. Using the data, the calculation of P is given as follows: (121.0+73.0)/68.0=2.8529. Therefore, the index Q for hypogrowth of the mandible is 852 and it can be decided that the degree of overgrowth of the mandible was improved.

Example 100

From FIG. 12 showing the tracing made based on the cephalometric radiogram of the patient 7 taken in the example 7, the distances (S–N), (S–B) and (Go–B) were measured. The results are: (S–N)=67.0 mm, (S–B)=111.0 mm and (Go–B)=73.0 mm. Using the data, the calculation of P is given as follows: (111.0+73.0)/67.0=2.7462. Therefore, the index Q for hypogrowth of the mandible is 746 and it can be decided there is overgrowth of the mandible.

Example 101

From FIG. 13 showing the tracing made based on the cephalometric radiogram of the patient 8 taken in the example 8, the distances (S–N), (S–B) and (Go–B) were measured. The results are: (S–N)=68.0 mm, (S–B)=127.0 mm and (Go–B)=80.0 mm. Using the data, the calculation of P is given as follows: (127.0+80.0)/68.0=3.0441. Therefore, the index Q for hypogrowth of the mandible is 1044 and it can be decided that there is serious overgrowth of the mandible.

Example 102

From FIG. 14 showing the tracing made based on the cephalometric radiogram of the patient 9 taken in the example 9, the distances (S–N), (S–B) and (Go–B) were measured. The results are: (S–N)=68.0 mm, (S–B)=105.0 mm and (Go–B)=74.0 mm. Using the data, the calculation of P is given as follows: (105.0+74.0)/68.0=2.6323. Therefore, the index Q for hypogrowth of the mandible is 632 and it can be decided that there is overgrowth of the mandible.

Example 103

From FIG. 15 showing the tracing made based on the cephalometric radiogram of the patient 10 taken in the example 10, the distances (S–N), (S–B) and (Go–B) were measured. The results are: (S–N)=69.0 mm, (S–B)=103.0 mm and (Go–B)=72.0 mm. Using the data, the calculation of P is given as follows: (103.0+72.0)/69.0=2.5362. Therefore, the index Q for hypogrowth of the mandible is 536 and it can be decided that there is slight overgrowth of the mandible.

Example 104

From FIG. 16 showing the tracing made based on the cephalometric radiogram of the patient 11 taken in the example 11, the distances (S–N), (S–B) and (Go–B) were measured. The results are: (S–N)=63.0 mm, (S–B)=108.0 mm and (Go–B)=69.0 mm. Using the data, the calculation of P is given as follows: (108.0+69.0)/63.0=2.8095. Therefore, the index Q for hypogrowth of the mandible is 809 and it can be decided that there is overgrowth of the mandible.

Example 105

From FIG. 17 showing the tracing made based on the cephalometric radiogram of the patient 12 taken in the example 12, the distances (S–N), (S–B) and (Go–B) were measured. The results are: (S–N)=74.0 mm, (S–B)=115.0 mm and (Go–B)=70.0 mm. Using the data, the calculation of P is given as follows: (115.0+70.0)/74.0=2.5000. Therefore, the index Q for hypogrowth of the mandible is 500 and it can be decided that the mandible is normal.

Example 106

From FIG. 21 showing the tracing made based on the cephalometric radiogram of the patient 13 taken in the example 37, (S–N)=60.0 mm, (S–B)=88.0 mm and (Go–B)=57.0 mm. Using the data, the calculation of P is given as follows: (88.0+57.0)/60.0=2.4166. Therefore, the index Q for hypogrowth of the mandible is 416 and it can be decided there is hypogrowth of the mandible.

A proper facial mask was attached to the face of the patient 13 for improvement of hypogrowth of the maxilla. After using the facial mask for two years, a cephalometric radiogram of the patient 13 was taken. A tracing made based on the cephalometric radiogram of the patient 13 is shown in FIG. 22. From FIG. 22, (S–N)=61.0 mm, (S–B)=90.0 mm and (Go–B)=59.0 mm. Using the data, the calculation of P is given as follows: (90.0+59.0)/61.0=2.4426. Therefore, the index Q for hypogrowth of the mandible is 442, so it can be decided that the degree of hypogrowth of the mandible was improved.

Example 107

From FIG. 23 showing the tracing made based on the cephalometric radiogram of the patient 14 taken in the example 38, (S–N)=69.0 mm, (S–B)=110.0 mm and (Go–B)=74.0 mm. Using the data, the calculation of P is given as follows: (110.0+74.0)/69.0=2.6666. Therefore, the index Q for hypogrowth of the mandible is 666 and it can be decided that there is overgrowth of the mandible.

As the OPE index Q, which is calculated by the Equation (1), is 376, it is a borderline case. Accordingly, the severing operation on the mandible was performed. After 7 years from the severing operation on the mandible, a cephalometric radiogram of the patient 14 was taken. A tracing made based on the cephalometric radiogram is shown in FIG. 24. From FIG. 24, (S–N)=69.0 mm, (S–B)=121.0 mm and (Go–B)=77.0 mm. Using the data, the calculation of P is given as follows: (121.0+77.0)/69.0=2.8695. Therefore, the index Q for hypogrowth of the mandible is 869 and it can be decided that there is overgrowth of the mandible.

Example 108

From FIG. 25 showing the tracing made based on the cephalometric radiogram of the patient 15 taken in the example 39, (S–N)=66.0 mm, (S–B)=93.0 mm and (Go–B)=60.0 mm. Using the data, the calculation of P is given as follows: (93.0+60.0)/66.0=2.3181. Therefore, the index Q for hypogrowth of the mandible is 318 and it can be decided that there is serious hypogrowth of the mandible.

After using the headgear for one year and 9 months for improvement of hypogrowth of the mandible, a cephalometric radiogram of the patient 15 was taken. A tracing made based on the cephalometric radiogram is shown in FIG. 26. From FIG. 26, (S–N)=66.0 mm, (S–B)=95.0 mm and (Go–B)=63.0 mm. Using the data, the calculation of P is given as follows: (95.0+63.0)/66.0=2.3939. Therefore, the index Q for hypogrowth of the mandible is 393 and it can be decided that the degree of hypogrowth of the mandible was improved greatly.

After using the headgear for 3 years and 2 months more, a cephalometric radiogram of the patient 15 was taken. A tracing made based on the cephalometric radiogram is shown in FIG. 27. From FIG. 27, (S–N)=66.0 mm, (S–B)=103.0 mm and (Go–B)=63.0 mm. Using the data, the calculation of P is given as follows: (103.0+63.0)/66.0=2.5151. Therefore, the index Q for hypogrowth of the mandible is 515 and it can be decided that the mandible was improved to be normal.

Example 109

From FIG. 28 showing the tracing made based on the cephalometric radiogram of the patient 16 taken in the example 40, (S–N)=72.0 mm, (S–B)=110.0 mm and (Go–B)=73.0 mm. Using the data, the calculation of P is given as follows: (110.0+73.0)/72.0=2.5416. Therefore, the index Q for hypogrowth of the mandible is 541 and it can be decided that the mandible is normal.

Example 110

From FIG. 29 showing the tracing made based on the cephalometric radiogram of the patient 17 taken in the example 41, (S–N)=69.0 mm, (S–B)=103.0 mm and (Go–B)=73.0 mm. Using the data, the calculation of P is given as follows: (103.0+73.0)/69.0=2.5507. Therefore, the index Q for hypogrowth of the mandible is 550 and it can be decided that the mandible is normal.

Example 111

From FIG. 30 showing the tracing made based on the cephalometric radiogram of the patient 18 taken in the example 42, (S–N)=67.0 mm, (S–B)=110.0 mm and (Go–B)=75.0 mm. Using the data, the calculation of P is given as follows: (110.0+75.0)/67.0=2.7611. Therefore, the index Q for hypogrowth of the mandible is 761 and it can be decided that there is overgrowth of the mandible.

Example 112

From FIG. 31 showing the tracing made based on the cephalometric radiogram of the patient 19 taken in the example 43, (S–N)=70.0 mm, (S–B)=110.0 mm and (Go–B)=70.0 mm. Using the data, the calculation of P is given as follows: (110.0+70.0)/70.0=2.5714. Therefore, the index Q for hypogrowth of the mandible is 571 and it can be decided that the mandible is normal.

Example 113

From FIG. 32 showing the tracing made based on the cephalometric radiogram of the patient 20 taken in the example 44, (S–N)=70.0 mm, (S–B)=100.0 mm and (Go–B)=69.0 mm. Using the data, the calculation of P is given as follows: (100.0+69.0)/70.0=2.4142. Therefore, the index Q for hypogrowth of the mandible is 414 and it can be decided that there is hypogrowth of the mandible.

Example 114

From FIG. 33 showing the tracing made based on the cephalometric radiogram of the patient 21 taken in the example 45, (S–N)=74.0 mm, (S–B)=113.0 mm and (Go–B)=66.0 mm. Using the data, the calculation of P is given as follows: (113.0+66.0)/74.0=2.4189. Therefore, the index Q for hypogrowth of the mandible is 418 and it can be decided that there is hypogrowth of the mandible.

As explained, according to the method of calculating an index for hypogrowth of the mandible of the eighteenth embodiment, using the distances (S–N), (S–B) and (Go–B) which are measured by cephalometric radiography, the index Q for hypogrowth of the mandible can be calculated. And based on the index Q for hypogrowth of the mandible, the presence or absence or the degree of hypogrowth of the mandible can be decided without being influenced by the experience of a dentist or a doctor, and decided correctly with a short period of time, moreover with a certain objectivity.

19. Nineteenth Embodiment

In the nineteenth embodiment, a method of calculating an index for hypogrowth of the mandible is explained.

Before calculating, a cephalometric radiogram of a patient is taken, and the distances (S–N) and (S–B) are measured. These distances can be measured by the method which was explained before.

At first, in step S121, the distances (S–N) and (S–B) which are measured by the above are entered.

In step S122, from the entered (S–N) and (S–B), P is calculated according to $$P=(S-B)/(S-N). \quad (23)$$

In step S123, from P obtained by the calculation of the above, omitting the figures of the fourth decimal place and under of P, in case of $1.000 \leq P < 2.000$, the index Q for hypogrowth of the mandible is calculated according to $$Q=(P-[P]) \times 1000$$

and in case of P<1.000, the index Q for hypogrowth of the mandible is calculated according to $$Q=(P-([P]+1)) \times 1000.$$

In step S124, the index Q for hypogrowth of the mandible calculated as the above is output on a display, for example.

From the index Q for hypogrowth of the mandible calculated as the above, the presence or absence or the degree of hypogrowth of the mandible or overgrowth of the mandible can be decided objectively.

Example 115

From FIG. 3 showing the tracing made based on the cephalometric radiogram of the patient 1 taken in the example 1, the distances (S–N) and (S–B) were measured. The results are: (S–N)=67.0 mm and (S–B)=123 mm. Using the data, the calculation of P is given as follows: 123.0/67.0=1.8358. Therefore, the index Q for hypogrowth of the mandible is 835.

From FIG. 4 showing the tracing made based on the cephalometric radiogram of the patient 1 after the severing operation on the mandible taken in the example 1, the distances (S–N) and (S–B) were measured. The results are: (S–N)=67.0 mm and (S–B)=111 mm. Using the data, the calculation of P is given as follows: 111.0/67.0=1.6567. Therefore, the index Q for hypogrowth of the mandible is 656.

Example 116

From FIG. 5 showing the tracing made based on the cephalometric radiogram of the patient 2 taken in the example 2, the distances (S–N) and (S–B) were measured. The results are: (S–N)=69.0 mm and (S–B)=123 mm. Using the data, the calculation of P is given as follows: 123.0/69.0=1.7826. Therefore, the index Q for hypogrowth of the mandible is 782.

From FIG. 6 showing the tracing made based on the cephalometric radiogram of the patient 2 after the severing operation on the mandible, the distances (S–N) and (S–B) were measured. The results are: (S–N)=69.0 mm and (S–B)=116 mm. Using the data, the calculation of P is given as follows: 116.0/69.0=1.6811. Therefore, the index Q for hypogrowth of the mandible is 681.

Example 117

From FIG. 7 showing the tracing made based on the cephalometric radiogram of the patient 3 taken in the example 3, the distances (S–N) and (S–B) were measured. The results are: (S–N)=67.0 mm and (S–B)=126.0 mm. Using the data, the calculation of P is given as follows: 126.0/67.0=1.8805. Therefore, the index Q for hypogrowth of the mandible is 880.

Example 118

From FIG. 8 showing the tracing made based on the cephalometric radiogram of the patient 4 taken in the example 4, the distances (S–N) and (S–B) were measured. The results are: (S–N)=64.0 mm and (S–B)=119.0 mm. Using the data, the calculation of P is given as follows: 119.0/64.0=1.8593. Therefore, the index Q for hypogrowth of the mandible is 859.

Example 119

From FIG. 9 showing the tracing made based on the cephalometric radiogram of the patient 5 taken in the example 5, the distances (S–N) and (S–B) were measured. The results are: (S–N)=65.0 mm and (S–B)=109.0 mm. Using the data, the calculation of P is given as follows: 109.0/65.0=1.6769. Therefore, the index Q for hypogrowth of the mandible is 676.

Example 120

From FIG. 10 showing the tracing made based on the cephalometric radiogram of the patient 6 taken in the example 6, the distances (S–N) and (S–B) were measured. The results are: (S–N)=68.0 mm and (S–B)=128.0 mm. Using the data, the calculation of P is given as follows: 128.0/68.0=1.8823. Therefore, the index Q for hypogrowth of the mandible is 882.

From FIG. 11 showing the tracing made based on the cephalometric radiogram of the patient 6 after the severing operation on the mandible, the distances (S–N) and (S–B) were measured. The results are: (S–N)=68.0 mm and (S–B)=121.0 mm. Using the data, the calculation of P is given as follows: 121.0/68.0=1.7794. Therefore, the index Q for hypogrowth of the mandible is 779.

Example 121

From FIG. 12 showing the tracing made based on the cephalometric radiogram of the patient 7 taken in the example 7, the distances (S–N) and (S–B) were measured. The results are: (S–N)=67.0 mm and (S–B)=111.0 mm. Using the data, the calculation of P is given as follows: 111.0/67.0=1.6567. Therefore, the index Q for hypogrowth of the mandible is 656.

Example 122

From FIG. 13 showing the tracing made based on the cephalometric radiogram of the patient 8 taken in the example 8, the distances (S–N) and (S–B) were measured. The results are: (S–N)=68.0 mm and (S–B)=127.0 mm. Using the data, the calculation of P is given as follows: 127.0/68.0=1.8676. Therefore, the index Q for hypogrowth of the mandible is 867.

Example 123

From FIG. 14 showing the tracing made based on the cephalometric radiogram of the patient 9 taken in the example 9, the distances (S–N) and (S–B) were measured. The results are: (S–N)=68.0 mm and (S–B)=105.0 mm. Using the data, the calculation of P is given as follows: 105.0/68.0=1.5441. Therefore, the index Q for hypogrowth of the mandible is 544.

Example 124

From FIG. 15 showing the tracing made based on the cephalometric radiogram of the patient 10 taken in the example 10, the distances (S–N) and (S–B) were measured. The results are: (S–N)=69.0 mm and (S–B)=103.0 mm. Using the data, the calculation of P is given as follows: 103.0/69.0=1.4927. Therefore, the index Q for hypogrowth of the mandible is 492.

Example 125

From FIG. 16 showing the tracing made based on the cephalometric radiogram of the patient 11 taken in the example 11, the distances (S–N) and (S–B) were measured. The results are: (S–N)=63.0 mm and (S–B)=108.0 mm. Using the data, the calculation of P is given as follows: 108.0/63.0=1.7142. Therefore, the index Q for hypogrowth of the mandible is 714.

Example 126

From FIG. 17 showing the tracing made based on the cephalometric radiogram of the patient 12 taken in the example 12, the distances (S–N) and (S–B) were measured. The results are: (S–N)=74.0 mm and (S–B)=115.0 mm. Using the data, the calculation of P is given as follows: 115.0/74.0=1.5540. Therefore, the index Q for hypogrowth of the mandible is 554.

As explained, according to the method of calculating an index for hypogrowth of the mandible of the nineteenth embodiment, using the distances (S–N) and (S–B) which are measured by cephalometric radiography, the index Q for hypogrowth of the mandible can be calculated. And based on the index Q for hypogrowth of the mandible, the presence or absence or the degree of hypogrowth of the mandible or overgrowth of the mandible can be decided without being influenced by the experience of a dentist or a doctor, and decided correctly with a short period of time, moreover with a certain objectivity.

20. Twentieth Embodiment

In the twentieth embodiment, a method of calculating an index for hypogrowth of the mandible is explained.

Before calculating, a cephalometric radiogram of a patient is taken, and the distances (S–N) and (S–B) are measured. These distances can be measured by the method which was explained before.

At first, in step S131, the distances (S–N) and (S–B) which are measured by the above are entered.

In step S132, from the entered (S–N) and (S–B), P is calculated according to $$P=(S-B)-(S-N). \tag{24}$$

In step S133, the index P for hypogrowth of the mandible calculated as the above is output on a display, for example.

From the index P for hypogrowth of the mandible calculated as the above, the presence or absence or the degree of hypogrowth of the mandible or overgrowth of the mandible can be decided objectively.

Example 127

From FIG. 3 showing the tracing made based on the cephalometric radiogram of the patient 1 taken in the example 1, the distances (S–N) and (S–B) were measured. The results are: (S–N)=67.0 mm and (S–B)=123 mm. Using the data, the calculation of P is given as follows: 123.0−67.0=56 mm. Therefore, the index P for hypogrowth of the mandible is 56 mm.

From FIG. 4 showing the tracing made based on the cephalometric radiogram of the patient 1 after the severing operation on the mandible taken in the example 1, the distances (S–N) and (S–B) were measured. The results are: (S–N)=67.0 mm and (S–B)=111 mm. Using the data, the calculation of P is given as follows: 111.0–67.0=44 mm. Therefore, the index P for hypogrowth of the mandible is 44 mm.

Example 128

From FIG. 5 showing the tracing made based on the cephalometric radiogram of the patient 2 taken in the example 2, the distances (S–N) and (S–B) were measured. The results are: (S–N)=69.0 mm and (S–B)=123 mm. Using the data, the calculation of P is given as follows: 123.0–69.0=54 mm. Therefore, the index P for hypogrowth of the mandible is 54 mm.

From FIG. 6 showing the tracing made based on the cephalometric radiogram of the patient 2 after the severing operation on the mandible, the distances (S–N) and (S–B) were measured. The results are: (S–N)=69.0 mm and (S–B)=116 mm. Using the data, the calculation of P is given as follows: 116.0–69.0=47 mm. Therefore, the index P for hypogrowth of the mandible is 47 mm.

Example 129

From FIG. 7 showing the tracing made based on the cephalometric radiogram of the patient 3 taken in the example 3, the distances (S–N) and (S–B) were measured. The results are: (S–N)=67.0 mm and (S–B)=126.0 mm. Using the data, the calculation of P is given as follows: 126.0–67.0=59 mm. Therefore, the index P for hypogrowth of the mandible is 59 mm.

Example 130

From FIG. 8 showing the tracing made based on the cephalometric radiogram of the patient 4 taken in the example 4, the distances (S–N) and (S–B) were measured. The results are: (S–N)=64.0 mm and (S–B)=119.0 mm. Using the data, the calculation of P is given as follows: 119.0–64.0=55 mm. Therefore, the index P for hypogrowth of the mandible is 55 mm.

Example 131

From FIG. 9 showing the tracing made based on the cephalometric radiogram of the patient 5 taken in the example 5, the distances (S–N) and (S–B) were measured. The results are: (S–N)=65.0 mm and (S–B)=109.0 mm. Using the data, the calculation of P is given as follows: 109.0–65.0=44 mm. Therefore, the index P for hypogrowth of the mandible is 44 mm.

Example 132

From FIG. 10 showing the tracing made based on the cephalometric radiogram of the patient 6 taken in the example 6, the distances (S–N) and (S–B) were measured. The results are: (S–N)=68.0 mm and (S–B)=128.0 mm. Using the data, the calculation of P is given as follows: 128.0–68.0=60 mm. Therefore, the index P for hypogrowth of the mandible is 60 mm.

From FIG. 11 showing the tracing made based on the cephalometric radiogram of the patient 6 after the severing operation on the mandible, the distances (S–N) and (S–B) were measured. The results are: (S–N)=68.0 mm and (S–B)=121.0 mm. Using the data, the calculation of P is given as follows: 121.0–68.0=53 mm. Therefore, the index P for hypogrowth of the mandible is 53 mm.

Example 133

From FIG. 12 showing the tracing made based on the cephalometric radiogram of the patient 7 taken in the example 7, the distances (S–N) and (S–B) were measured. The results are: (S–N)=67.0 mm and (S–B)=111.0 mm. Using the data, the calculation of P is given as follows: 111.0–67.0=44 mm. Therefore, the index P for hypogrowth of the mandible is 44 mm.

Example 134

From FIG. 13 showing the tracing made based on the cephalometric radiogram of the patient 8 taken in the example 8, the distances (S–N) and (S–B) were measured. The results are: (S–N)=68.0 mm and (S–B)=127.0 mm. Using the data, the calculation of P is given as follows: 127.0–68.0=59 mm. Therefore, the index P for hypogrowth of the mandible is 59 mm.

Example 135

From FIG. 14 showing the tracing made based on the cephalometric radiogram of the patient 9 taken in the example 9, the distances (S–N) and (S–B) were measured. The results are: (S–N)=68.0 mm and (S–B)=105.0 mm. Using the data, the calculation of P is given as follows: 105.0–68.0=37 mm. Therefore, the index P for hypogrowth of the mandible is 37 mm.

Example 136

From FIG. 15 showing the tracing made based on the cephalometric radiogram of the patient 10 taken in the example 10, the distances (S–N) and (S–B) were measured. The results are: (S–N)=69.0 mm and (S–B)=103.0 mm. Using the data, the calculation of P is given as follows: 103.0–69.0=34 mm. Therefore, the index P for hypogrowth of the mandible is 34 mm.

Example 137

From FIG. 16 showing the tracing made based on the cephalometric radiogram of the patient 11 taken in the example 11, the distances (S–N) and (S–B) were measured. The results are: (S–N)=63.0 mm and (S–B)=108.0 mm. Using the data, the calculation of P is given as follows: 108.0–63.0=45 mm. Therefore, the index P for hypogrowth of the mandible is 45 mm.

Example 138

From FIG. 17 showing the tracing made based on the cephalometric radiogram of the patient 12 taken in the example 12, the distances (S–N) and (S–B) were measured. The results are: (S–N)=74.0 mm and (S–B)=115.0 mm. Using the data, the calculation of P is given as follows: 115.0–74.0=41 mm. Therefore, the index P for hypogrowth of the mandible is 41 mm.

As explained, according to the method of calculating an index for hypogrowth of the mandible of the twentieth embodiment, using the distances (S–N) and (S–B) which are measured by cephalometric radiography, the index P for hypogrowth of the mandible can be calculated. And based on the index P for hypogrowth of the mandible, the presence or absence or the degree of hypogrowth of the mandible or overgrowth of the mandible can be decided without being influenced by the experience of a dentist or a doctor, and decided correctly with a short period of time, moreover with a certain objectivity.

21. Twenty-First Embodiment

In the twenty-first embodiment, a method of calculating an index for deciding the necessity of operating on the jaw in orthodontic treatment is explained.

Before calculating, a cephalometric radiogram of a patient to be undergone orthodontic treatment is taken, and the distances (S–A), (Go–A), (S–B) and (Go–B) are measured. These distances can be measured by the method which was explained before.

At first, in step S141, the distances (S–A), (Go–A), (S–B) and (Go–B) which are measured by the above are entered.

In step S142, from the entered (S–A), (Go–A), (S–B) and (Go–B), P is calculated according to $P=((S-B)+(Go-B))/((S-A)+(Go-A))$.

In step S143, 2P is calculated using P obtained by the calculation of the above, omitting the figures of the fourth decimal place and under of 2P, in case of $2.000 \leq P < 3.000$, the OPE index Q is calculated according to $Q=(P-[P]) \times 1000$ and in case of $P<2.000$, the OPE index Q is calculated according to $Q=(P-([P]+1)) \times 1000$.

In step S144, the OPE index Q calculated as the above is output on a display, for example.

In case that the OPE index Q calculated as the above is equal to or larger than $C_5$, it can be diagnosed that the severing operation on the mandible is necessary in orthodontic treatment. Also, in case that the OPE index Q is equal to or larger than $C_6$ and less than $C_5$, which is a borderline case, a supplementary analysis is added by Wits analysis. In case that the result of Wits analysis is equal to or larger than 12 mm, it is decided that the surgical operation is adaptable, in other words, the surgical operation on the jaw is necessary. $C_5$ and $C_6$ can be decided suitably.

In case that the OPE index Q is less than $C_6$ and equal to or larger than 0, it can be diagnosed that the surgical operation on the jaw is not necessary in orthodontic treatment.

In case that the OPE index Q is negative, denoting remarkable hypogrowth tendency of the mandible or overgrowth tendency of the maxilla, it is necessary to consider the surgical operation on the jaw.

Generally, in addition to the OPE index Q, a dentist finally decides the necessity of surgically operating on the jaw by combining other inspection results such as the conventional cephalometric analysis focusing mainly on angle measurement, etc.

Example 139

From FIG. 3 showing the tracing made based on the cephalometric radiogram of the patient 1 taken in the example 1, the distances (S–A), (Go–A), (S–B) and (Go–B) were measured. The results are: (S–A)=78.0 mm, (Go–A)=77.0 mm, (S–B)=123.0 mm and (Go–B)=78.0 mm. Using the data, the calculation of 2P is given as follows: $2 \times [(123.0+78.0)/(78.0+77.0)]=2.5935$. Therefore, the OPE index Q is 593.

For example, if $C_5$ is set as $C_5=470$, the OPE index Q is 593, so it can be decided that the patient 1 needs the severing operation on the mandible in orthodontic treatment.

Therefore, the necessary severing operation on the mandible was performed. From FIG. 4 showing the tracing made based on the cephalometric radiogram after the severing operation on the mandible of the patient 1 taken in the example 1, the distances (S–A), (Go–A), (S–B) and (Go–B) were measured. The results are: (S–A)=78.0 mm, (Go–A)=79.0 mm, (S–B)=111.0 mm and (Go–B)=73.0 mm. Using the data, the calculation of 2P is given as follows: $2 \times [(111.0+73.0)/(78.0+79.0)]=2.3439$. Therefore, the OPE index Q is 343.

For $C_5=470$, the OPE index Q is 343, so it can be decided that the patient 1 is able to be treated by orthodontic treatment as a result of the severing operation on the mandible.

Example 140

From FIG. 5 showing the tracing made based on the cephalometric radiogram of the patient 2 taken in the example 2, the distances (S–A), (Go–A), (S–B) and (Go–B) were measured. The results are: (S–A)=83.0 mm, (Go–A)=78.0 mm, (S–B)=123.0 mm and (Go–B)=80.0 mm. Using the data, the calculation of 2P is given as follows: $2 \times [(123.0+80.0)/(83.0+78.0)]=2.5217$. Therefore, the OPE index Q is 521.

For $C_5=470$, the OPE index Q is 521, so it can be decided that the patient 2 needs the severing operation on the mandible in orthodontic treatment.

Therefore, the necessary severing operation on the mandible was performed. From FIG. 6 showing the tracing made based on the cephalometric radiogram taken after the severing operation of the mandible of the patient 2, the distances (S–A), (Go–A), (S–B) and (Go–B) were measured. The results are: (S–A)=83.0 mm, (Go–A)=83.0 mm, (S–B)=116.0 mm and (Go–B)=80.0 mm. Using the data, the calculation of 2P is given as follows: $2 \times [(116.0+80.0)/(83.0+83.0)]=2.3614$. Therefore, the OPE index Q is 361.

For $C_5=470$, the OPE index Q is 361, so it can be decided that the patient 2 is able to be treated by orthodontic treatment as a result of the severing operation on the mandible.

Example 141

From FIG. 7 showing the tracing made based on the cephalometric radiogram of the patient 3 taken in the example 3, the distances (S–A), (Go–A), (S–B) and (Go–B) were measured. The results are: (S–A)=88.0 mm, (Go–A)=85.0 mm, (S–B)=126.0 mm and (Go–B)=80.0 mm. Using the data, the calculation of 2P is given as follows: $2 \times [(126.0+80.0)/(88.0+85.0)]=2.3815$. Therefore, the OPE index Q is 381.

This is a case of light skeletal class III. However, for $C_5=470$ the OPE index Q is 381, so it can be decided that the patient 3 does not need the surgical operation on the jaw in orthodontic treatment.

Example 142

From FIG. 8 showing the tracing made based on the cephalometric radiogram of the patient 4 taken in the example 4, the distances (S–A), (Go–A), (S–B) and (Go–B) were measured. The results are: (S–A)=85.0 mm, (Go–A)=78.0 mm, (S–B)=119.0 mm and (Go–B)=76.0 mm. Using the data, the calculation of 2P is given as follows: $2 \times [(119.0+76.0)/(85.0+78.0)]=2.3926$. Therefore, the OPE index Q is 392.

This is a case of skeletal class III. However, for $C_5$=470 the OPE index Q is 392, so it can be decided that the patient 4 does not need the surgical operation on the jaw in orthodontic treatment.

Example 143

From FIG. 9 showing the tracing made based on the cephalometric radiogram of the patient 5 taken in the example 5, the distances (S–A), (Go–A), (S–B) and (Go–B) were measured. The results are: (S–A)=75.0 mm, (Go–A)=74.0 mm, (S–B)=109.0 mm and (Go–B)=73.0 mm. Using the data, the calculation of 2P is given as follows: 2×[(109.0+73.0)/(75.0+74.0)]=2.4429. Therefore, the OPE index Q is 442.

For $C_5$=470 the OPE index Q is 442, so it is a borderline case. Wits is 10.0 mm, which shows a very strong skeletal case. However, Wits is equal to or less than 12 mm, further with (S–N)=65.0 mm, so it can be decided that the surgical operation on the jaw is not necessary in orthodontic treatment.

Example 144

From FIG. 10 showing the tracing made based on the cephalometric radiogram of the patient 6 taken in the example 6, the distances (S–A), (Go–A), (S–B) and (Go–B) were measured. The results are: (S–A)=87.0 mm, (Go–A)=79.0 mm, (S–B)=128.0 mm and (Go–B)=80.0 mm. Using the data, the calculation of 2P is given as follows: 2×[(128.0+80.0)/(87.0+79.0)]=2.5060. Therefore, the OPE index Q is 506.

For $C_5$=470 the OPE index Q is 506, so it is a borderline case. Wits is 12.0 mm, further with (S–N)=68.0 mm, which shows a skeletal class III, and it can be decided that the patient 6 suffers from dentofacial deformity, and can be decided that the severing operation on the mandible is necessary.

Therefore, the necessary severing operation on the mandible was performed. From FIG. 11 showing the tracing made based on the cephalometric radiogram taken after the severing operation on the mandible of the patient 6, the distances (S–A), (Go–A), (S–B) and (Go–B) were measured. The results are: (S–A)=87.0 mm, (Go–A)=77.0 mm, (S–B)=121.0 mm and (Go–B)=73.0 mm. Using the data, the calculation of 2P is given as follows: 2×[(121.0+73.0)/(87.0+77.0)]=2.3658. Therefore, the OPE index Q is 365.

For $C_3$=470 the OPE index Q is 365, so it can be decided that the patient 6 is able to be treated by orthodontic treatment as a result of the severing operation on the mandible.

Example 145

From FIG. 12 showing the tracing made based on the cephalometric radiogram of the patient 7 taken in the example 7, the distances (S–A), (Go–A), (S–B) and (Go–B) were measured. The results are: (S–A)=86.0 mm, (Go–A)=86.0 mm, (S–B)=111.0 mm and (Go–B)=73.0 mm. Using the data, the calculation of 2P is given as follows: 2×[(111.0+73.0)/(86.0+86.0)]=2.1395. Therefore, the OPE index Q is 139.

For $C_5$=470 the OPE index Q is 139, so there is a withdrawing tendency of the mandible. However, it can be decided that the patient 7 does not need the surgical operation on the jaw in orthodontic treatment, and orthodontic treatment with a tooth extraction is adaptable.

Example 146

From FIG. 13 showing the tracing made based on the cephalometric radiogram of the patient 8 taken in the example 8, the distances (S–A), (Go–A), (S–B) and (Go–B) were measured. The results are: (S–A)=90.0 mm, (Go–A)=79.0 mm, (S–B)=127.0 mm and (Go–B)=80.0 mm. Using the data, the calculation of 2P is given as follows: 2×[(127.0+80.0)/(90.0+79.0)]=2.4497. Therefore, the OPE index Q is 449.

For $C_3$=470 the OPE index Q is 449, so it can be decided that the patient 8 does not need the surgical operation on the jaw in orthodontic treatment.

Example 147

From FIG. 14 showing the tracing made based on the cephalometric radiogram of the patient 9 taken in the example 9, the distances (S–A), (Go–A), (S–B) and (Go–B) were measured. The results are: (S–A)=79.0 mm, (Go–A)=81.0 mm, (S–B)=105.0 mm and (Go–B)=74.0 mm. Using the data, the calculation of 2P is given as follows: 2×[(105.0+74.0)/(79.0+81.0)]=2.2375. Therefore, the OPE index Q is 237.

For $C_3$=470 the OPE index Q is 237, so it can be decided that the patient 9 does not need the surgical operation on the jaw in orthodontic treatment.

Example 148

From FIG. 15 showing the tracing made based on the cephalometric radiogram of the patient 10 taken in the example 10, the distances (S–A), (Go–A), (S–B) and (Go–B) were measured. The results are: (S–A)=81.0 mm, (Go–A)=83.0 mm, (S–B)=103.0 mm and (Go–B)=72.0 mm. Using the data, the calculation of 2P is given as follows: 2×[(103.0+72.0)/(81.0+83.0)]=2.1341. Therefore, the OPE index Q is 134.

This is a case of non-skeletal. However, for $C_3$=470 the OPE index Q is 134, so it can be decided that the patient 10 does not need the surgical operation on the jaw in orthodontic treatment, and orthodontic treatment with a non-tooth extraction is adaptable.

Example 149

From FIG. 16 showing the tracing made based on the cephalometric radiogram of the patient 11 taken in the example 11, the distances (S–A), (Go–A), (S–B) and (Go–B) were measured. The results are: (S–A)=81.0 mm, (Go–A)=78.0 mm, (S–B)=108.0 mm and (Go–B)=69.0 mm. Using the data, the calculation of 2P is given as follows: 2×[(108.0+69.0)/(81.0+78.0)]=2.2264. Therefore, the OPE index Q is 226.

For $C_5$=470 the OPE index Q is 226, and Wits is 2.0 mm, which shows a non-skeletal case. However, it can be decided that the patient 11 does not need the surgical operation on the jaw in orthodontic treatment, and orthodontic treatment with a non-tooth extraction is adaptable.

Example 150

From FIG. 17 showing the tracing made based on the cephalometric radiogram of the patient 12 taken in the example 12, the distances (S–A), (Go–A), (S–B) and (Go–B) were measured. The results are: (S–A)=91.0 mm, (Go–A)=87.0 mm, (S–B)=115.0 mm and (Go–B)=70.0 mm. Using the data, the calculation of 2P is given as follows: 2×[(115.0+70.0)/(91.0+87.0)]=2.0786. Therefore, the OPE index Q is 78.

For $C_5$=470 the OPE index Q is 78, so it can be decided that the patient 12 does not need the surgical operation on the jaw in orthodontic treatment.

Example 151

From FIG. 21 showing the tracing made based on the cephalometric radiogram of the patient 13 taken in the example 37, (S–A)=68.0 mm, (Go–A)=63.0 mm, (S–B)=88.0 mm and (Go–B)=57.0 mm. Using the data, the calculation of 2P is given as follows: 2×[(88.0+57.0)/(68.0+63.0)]=2.2137. Therefore, the OPE index Q is 213.

For $C_5$=470 the OPE index Q is 213, so it can be decided that the patient 13 does not need the surgical operation on the jaw in orthodontic treatment.

After using the facial mask for two years for improvement of hypogrowth of the maxilla, a cephalometric radiogram of the patient 13 was taken. A tracing made based on the cephalometric radiogram of the patient 13 is shown in FIG. 22. From FIG. 22, (S–A)=71.0 mm, (Go–A)=67.0 mm, (S–B)=90.0 mm and (Go–B)=59.0 mm. Using the data, the calculation of 2P is given as follows: 2×[(90.0+59.0)/(71.0+67.0)]=2.1594. Therefore, the OPE index Q is 159.

For $C_5$=470 the OPE index Q is 159, so it can be decided that the patient 13 does not need the surgical operation on the jaw in orthodontic treatment.

Example 152

From FIG. 23 showing the tracing made based on the cephalometric radiogram of the patient 14 taken in the example 38, (S–A)=77.0 mm, (Go–A)=76.0 mm, (S–B)=110.0 mm and (Go–B)=74.0 mm. Using the data, the calculation of 2P is given as follows: 2×[(110.0+74.0)/(77.0+76.0)]=2.3439. Therefore, the OPE index Q is 343.

After 7 years from the severing operation on the mandible, a cephalometric radiogram of the patient 14 was taken. A tracing made based on the cephalometric radiogram is shown in FIG. 24. From FIG. 24, (S–A)=85.0 mm, (Go–A)=85.0 mm, (S–B)=121.0 mm and (Go–B)=77.0 mm. Using the data, the calculation of 2P is given as follows: 2×[(121.0+77.0)/(85.0+85.0)]=2.3294. Therefore, the OPE index Q is 329.

Example 153

From FIG. 25 showing the tracing made based on the cephalometric radiogram of the patient 15 taken in the example 39, (S–A)=83.0 mm, (Go–A)=78.0 mm, (S–B)=93.0 mm and (Go–B)=60.0 mm. Using the data, the calculation of 2P is given as follows: 2×[(93.0+60.0)/(83.0+78.0)]=1.9006. Therefore, the OPE index Q is −100.

After using the headgear for one year and 9 months for improvement of hypogrowth of the mandible, a cephalometric radiogram of the patient 15 was taken. A tracing made based on the cephalometric radiogram is shown in FIG. 26. From FIG. 26, (S–A)=83.0 mm, (Go–A)=79.0 mm, (S–B)=95.0 mm and (Go–B)=63.0 mm. Using the data, the calculation of 2P is given as follows: 2×[(95.0+63.0)/(83.0+79.0)]=1.9259. Therefore, the OPE index Q is −75.

After using the headgear for 3 years and 2 months more, a cephalometric radiogram of the patient 15 was taken. A tracing made based on the cephalometric radiogram is shown in FIG. 27. From FIG. 27, (S–A)=85.0 mm, (Go–A)=82.0 mm, (S–B)=103.0 mm and (Go–B)=59.0 mm. Using the data, the calculation of 2P is given as follows: 2×[(103.0+59.0)/(85.0+82.0)]=1.9401. Therefore, the OPE index Q is −60.

For $C_5$=470 the OPE index Q is −60, so it can be decided that the patient 15 does not need the severing operation on the jaw in orthodontic treatment.

Example 154

From FIG. 28 showing the tracing made based on the cephalometric radiogram of the patient 16 taken in the example 40, (S–A)=87.0 mm, (Go–A)=89.0 mm, (S–B)=110.0 mm and (Go–B)=73.0 mm. Using the data, the calculation of 2P is given as follows: 2×[(110.0+73.0)/(87.0+89.0)]=2.0795. Therefore, the OPE index Q is 79.

For $C_5$=470 the OPE index Q is 79, so it can be decided that the patient 16 does not need the surgical operation on the jaw in orthodontic treatment.

Example 155

From FIG. 29 showing the tracing made based on the cephalometric radiogram of the patient 17 taken in the example 41, (S–A)=79.0 mm, (Go–A)=82.0 mm, (S–B)=103.0 mm and (Go–B)=73.0 mm. Using the data, the calculation of 2P is given as follows: 2×[(103.0+73.0)/(79.0+82.0)]=2.1863. Therefore, the OPE index Q is 186.

For $C_5$=470 the OPE index Q is 186, so it can be decided that the patient 17 does not need the surgical operation on the jaw in orthodontic treatment.

Example 156

From FIG. 30 showing the tracing made based on the cephalometric radiogram of the patient 18 taken in the example 42, (S–A)=82.0 mm, (Go–A)=88.0 mm, (S–B)=110.0 mm and (Go–B)=75.0 mm. Using the data, the calculation of 2P is given as follows: 2×[(110.0+75.0)/(82.0+88.0)]=2.1764. Therefore, the OPE index Q is 176.

For $C_5$=470 the OPE index Q is 176, so it can be decided that the patient 18 does not need the surgical operation on the jaw in orthodontic treatment.

Example 157

From FIG. 31 showing the tracing made based on the cephalometric radiogram of the patient 19 taken in the example 43, (S–A)=83.0 mm, (Go–A)=75.0 mm, (S–B)=110.0 mm and (Go–B)=70.0 mm. Using the data, the calculation of 2P is given as follows: 2×[(110.0+70.0)/(83.0+75.0)]=2.2784. Therefore, the OPE index Q is 278.

For $C_5$=470 the OPE index Q is 278, so it can be decided that the patient 19 does not need the surgical operation on the jaw in orthodontic treatment.

Example 158

From FIG. 32 showing the tracing made based on the cephalometric radiogram of the patient 20 taken in the example 44, (S–A)=68.0 mm, (Go–A)=77.0 mm, (S–B)=100.0 mm and (Go–B)=69.0 mm. Using the data, the calculation of 2P is given as follows: 2×[(100.0+69.0)/(68.0+77.0)]=2.3310. Therefore, the OPE index Q is 331.

For $C_5$=470 the OPE index Q is 331, so it can be decided that the patient 20 does not need the surgical operation on the jaw in orthodontic treatment.

Example 159

From FIG. 33 showing the tracing made based on the cephalometric radiogram of the patient 21 taken in the example 45, (S–A)=91.0 mm, (Go–A)=89.0 mm, (S–B)= 113.0 mm and (Go–B)=66.0 mm. Using the data, the calculation of 2P is given as follows: 2×[(113.0+66.0)/(91.0+ 89.0)]=1.9888. Therefore, the OPE index Q is −12.

For $C_5$=470 the OPE index Q is −12, so it can be decided that the patient 21 does not need the surgical operation on the jaw in orthodontic treatment.

As explained, according to the method of calculating an index for deciding the necessity of surgically operating on the jaw of the twenty-first embodiment, using the distances (S–A), (Go–A), (S–B) and (Go–B) which are measured by cephalometric radiography, the OPE index Q can be calculated. And based on the OPE index Q, the necessity of surgically operating on the jaw can be decided without being influenced by the experience of a dentist, and decided correctly with a short period of time, moreover with a certain objectivity.

22. Twenty-Second Embodiment

In the twenty-second embodiment, using the method of calculating an index for deciding the necessity of surgically operating on the jaw which was explained in the twenty-first embodiment, a method of deciding the necessity of operating on the jaw in orthodontic treatment is carried out as the same as the second embodiment.

According to the twenty-second embodiment, based on the index for deciding the necessity of surgically operating on the jaw, the decision of the necessity of surgically operating on the jaw can be done correctly with a short period of time, moreover with a certain objectivity without being influenced by the experience of a dentist.

23. Twenty-Third Embodiment

In the twenty-third embodiment, an index for deciding disharmony of the maxilla and mandible is calculated by a method as the same as the method of calculating an index for deciding the necessity of surgically operating on the jaw in orthodontic treatment as explained in the twenty-first embodiment.

According to the twenty-third embodiment, the index for deciding disharmony of the maxilla and mandible can be calculated easily. And based on the index for deciding disharmony of the maxilla and mandible, without being influenced by the experience of a dentist or a doctor, disharmony of the maxilla and mandible in dental treatment such as orthodontic treatment, etc. or medical treatment can be decided correctly with a short period of time, moreover with a certain objectivity.

24. Twenty-Fourth Embodiment

In the twenty-fourth embodiment, using the method of calculating an index for deciding disharmony of the maxilla and mandible which was explained in the twenty-third embodiment, a method of deciding disharmony of the maxilla and mandible is carried out as the same as the fourth embodiment.

According to the twenty-fourth embodiment, based on the index for deciding disharmony of the maxilla and mandible, in dental treatment such as orthodontic treatment, etc. or medical treatment, the decision of disharmony of the maxilla and mandible can be done correctly with a short period of time, moreover with a certain objectivity without being influenced by the experience of a dentist or a doctor.

25. Twenty-Fifth Embodiment

In the twenty-fifth embodiment, an index for deciding dentofacial deformity is calculated by a method as the same as the method of calculating an index for deciding the necessity of surgically operating on the jaw in orthodontic treatment as explained in the twenty-first embodiment.

According to the twenty-fifth embodiment, the index for deciding dentofacial deformity can be calculated easily. And based on the index for deciding dentofacial deformity, without being influenced by the experience of a dentist or a doctor, the decision of dentofacial deformity can be done correctly with a short period of time, moreover with a certain objectivity.

26. Twenty-Sixth Embodiment

In the twenty-sixth embodiment, using the method of calculating an index for deciding dentofacial deformity which was explained in the twenty-fifth embodiment, a method of deciding dentofacial deformity is carried out as the same as the sixth embodiment.

According to the twenty-sixth embodiment, based on the index for deciding dentofacial deformity, without being influenced by the experience of a dentist or a doctor, the decision of dentofacial deformity can be done correctly with a short period of time, moreover with a certain objectivity.

27. Twenty-Seventh Embodiment

In the twenty-seventh embodiment, a method of calculating an OPE index as the index for deciding the necessity of surgically operating on the jaw in orthodontic treatment is explained.

Before calculating, a cephalometric radiogram of a patient is taken, and the distances (S–A), (S–N), (S–B) and (Go–Me) are measured. These distances can be measured by the method which was explained before.

In step S151, the distances (S–A), (S–N), (S–B) and (Go–Me) which are measured by the above are entered.

In step S152, from the entered (S–A), (S–N), (S–B) and (Go–Me), P' is calculated according to $P'=((S-B)+(Go-Me))/((S-A)+(S-N))$.

In step S153, from P' obtained by the calculation of the above, omitting the figures of the fourth decimal place and under of P', in case of 1.000≤P'<2.000, the OPE index Q' is calculated according to $Q'=(P'-[P'])\times 1000$ and in case of P'<1.000, the OPE index Q' is calculated according to $Q'=(P'-([P']+1))\times 1000$.

In step S154, the OPE index Q' calculated as the above is output on a display, for example.

In case that the OPE index Q' calculated as the above is equal to or larger than 330, it can be diagnosed that the severing operation on the mandible is necessary in orthodontic treatment. Also, in case that the OPE index Q' is equal to or larger than 270 and less than 330, which is a borderline case, a supplementary analysis is added by Wits analysis. In case that the result of Wits analysis is equal to or larger than 12 mm, it is decided that the surgical operation is adaptable, in other words, the surgical operation on the jaw is necessary.

In case that the OPE index Q' is equal to or larger than 0 and less than 330, it can be diagnosed that the surgical operation on the jaw is not necessary in orthodontic treatment.

In case that the OPE index Q' is negative, denoting a remarkable hypogrowth tendency of the mandible or overgrowth tendency of the maxilla, it is necessary to consider the surgical operation on the jaw.

Generally, in addition to the OPE index Q', a dentist finally decides the necessity of surgically operating on the jaw by combining other inspection results such as the conventional cephalometric analysis focusing mainly on angle measurement, etc.

Example 160

From FIG. 3 showing the tracing made based on the cephalometric radiogram of the patient 1 taken in the example 1, the distances (S–A), (S–N), (S–B) and (Go–Me) were measured. The results are: (S–A)=78.0 mm, (S–N)=67.0 mm, (S–B)=123.0 mm and (Go–Me)=78.0 mm. Using the data, the calculation of P' is given as follows: (123.0+78.0)/(78.0+67.0)=1.3862. Therefore, the OPE index Q' is 386. It is to be noted that Wits=17.0 mm.

As the OPE index Q' is 386, it can be decided that the patient 1 needs the severing operation on the mandible in orthodontic treatment.

Therefore, the necessary severing operation on the mandible was performed. From FIG. 4 showing the tracing made based on the cephalometric radiogram of the patient 1 after the severing operation on the mandible taken in the example 1, the distances (S–A), (S–N), (S–B) and (Go–Me) were measured. The results are: (S–A)=78.0 mm, (S–N)=67.0 mm, (S–B)=111.0 mm and (Go–Me)=73.0 mm. Using the data, the calculation of P' is given as follows: (111.0+73.0)/(78.0+67.0)=1.2689. Therefore, the OPE index Q' is 268. It is to be noted that Wits=4.0 mm.

As the OPE index Q' is 268, it can be decided that the patient 1 is able to be treated by orthodontic treatment as a result of the severing operation on the mandible.

Example 161

From FIG. 5 showing the tracing made based on the cephalometric radiogram of the patient 2 taken in the example 2, the distances (S–A), (S–N), (S–B) and (Go–Me) were measured. The results are: (S–A)=83.0 mm, (S–N)=69.0 mm, (S–B)=123.0 mm and (Go–Me)=81.0 mm. Using the data, the calculation of P' is given as follows: (123.0+81.0)/(83.0+69.0)=1.3421. Therefore, the OPE index Q' is 342. It is to be noted that Wits=16.0 mm.

As the OPE index Q' is 342, it can be decided that the patient 2 needs the severing operation on the mandible.

Therefore, the necessary severing operation on the mandible was performed. From FIG. 6 showing the tracing made based on the cephalometric radiogram of the patient 2 after the severing operation on the mandible, the distances (S–A), (S–N), (S–B) and (Go–Me) were measured. The results are: (S–A)=83.0 mm, (S–N)=69.0 mm, (S–B)=116.0 mm and (Go–Me)=80.0 mm. Using the data, the calculation of P' is given as follows: (116.0+80.0)/(83.0+69.0)=1.289. Therefore, the OPE index Q' is 289. It is to be noted that Wits=6.0 mm.

As the OPE index Q' is 289, it can be decided that the patient 2 is able to be treated by orthodontic treatment as a result of the severing operation on the mandible.

Example 162

From FIG. 7 showing the tracing made based on the cephalometric radiogram of the patient 3 taken in the example 3, the distances (S–A), (S–N), (S–B) and (Go–Me) were measured. The results are: (S–A)=88.0 mm, (S–N)=67.0 mm, (S–B)=126.0 mm and (Go–Me)=78.0 mm. Using the data, the calculation of P' is given as follows: (126.0+78.0)/(88.0+67.0)=1.3161. Therefore, the OPE index Q' is 316. It is to be noted that Wits=7.0 mm.

This is a case of light skeletal class III. However, the OPE index Q' is 316, so it can be decided that the patient 3 does not need the surgical operation on the jaw in orthodontic treatment.

Example 163

From FIG. 8 showing the tracing made based on the cephalometric radiogram of the patient 4 taken in the example 4, the distances (S–A), (S–N), (S–B) and (Go–Me) were measured. The results are: (S–A)=85.0 mm, (S–N)=64.0 mm, (S–B)=119.0 mm and (Go–Me)=77.0 mm. Using the data, the calculation of P' is given as follows: (119.0+77.0)/(85.0+64.0)=1.3154. Therefore, the OPE index Q' is 315. It is to be noted that Wits=9.0 mm.

This is a case of skeletal class III. However, the OPE index Q' is 315, so it can be decided that the patient 4 does not need the surgical operation on the jaw in orthodontic treatment.

Example 164

From FIG. 9 showing the tracing made based on the cephalometric radiogram of the patient 5 taken in the example 5, the distances (S–A), (S–N), (S–B) and (Go–Me) were measured. The results are: (S–A)=75.0 mm, (S–N)=65.0 mm, (S–B)=109.0 mm and (Go–Me)=70.0 mm. Using the data, the calculation of P' is given as follows: (109.0+70.0)/(75.0+65.0)=1.2785. Therefore, the OPE index Q' is 278. It is to be noted that Wits=10.0 mm.

The OPE index Q' is 278, so it is a borderline case. Wits is 10.0 mm, which shows a very strong skeletal case. However, Wits is equal to or less than 12 mm, further with (S–N)=65.0 mm, so it can be decided that the surgical operation on the jaw is not necessary in orthodontic treatment.

Example 165

From FIG. 10 showing the tracing made based on the cephalometric radiogram of the patient 6 taken in the example 6, the distances (S–A), (S–N), (S–B) and (Go–Me) were measured. The results are: (S–A)=87.0 mm, (S–N)=68.0 mm, (S–B)=128.0 mm and (Go–Me)=80.0 mm. Using the data, the calculation of P' is given as follows: (128.0+80.0)/(87.0+68.0)=1.3419. Therefore, the OPE index Q' is 341. It is to be noted that Wits=12.0 mm.

The OPE index Q' is 341, so it is a borderline case. Wits is 12.0 mm, further with (S–N)=68.0 mm, which shows a skeletal class III, and it can be decided that the patient 6 suffers from dentofacial deformity, and can be decided that the severing operation on the mandible is necessary.

Therefore, the necessary severing operation on the mandible was performed. From FIG. 11 showing the tracing made based on the cephalometric radiogram taken after the severing operation on the mandible of the patient 6, the distances (S–A), (S–N), (S–B) and (Go–Me) were measured. The results are: (S–A)=87.0 mm, (S–N)=68.0 mm, (S–B)=121.0 mm and (Go–Me)=73.0 mm. Using the data, the calculation of P' is given as follows: (121.0+73.0)/(87.0+68.0)=1.2516. Therefore, the OPE index Q' is 251. It is to be noted that Wits=5.0 mm.

The OPE index Q' is 251, so it can be decided that the patient 6 is able to be treated by orthodontic treatment as a result of the severing operation on the mandible.

Example 166

From FIG. 12 showing the tracing made based on the cephalometric radiogram of the patient 7 taken in the example 7, the distances (S–A), (S–N), (S–B) and (Go–Me) were measured. The results are: (S–A)=86.0 mm, (S–N)=67.0 mm, (S–B)=111.0 mm and (Go–Me)=69.0 mm. Using the data, the calculation of P' is given as follows: (111.0+69.0)/(86.0+67.0)=1.1764. Therefore, the OPE index Q' is 176. It is to be noted that Wits=0 mm.

The OPE index Q' is 176, so there is a withdrawing tendency of the mandible. However, it can be decided that the patient 7 does not need the surgical operation on the jaw in orthodontic treatment, and orthodontic treatment with a tooth extraction is adaptable.

Example 167

From FIG. 13 showing the tracing made based on the cephalometric radiogram of the patient 8 taken in the example 8, the distances (S–A), (S–N), (S–B) and (Go–Me) were measured. The results are: (S–A)=90.0 mm, (S–N)=68.0 mm, (S–B)=127.0 mm and (Go–Me)=80.0 mm. Using the data, the calculation of P' is given as follows: (127.0+80.0)/(90.0+68.0)=1.3101. Therefore, the OPE index Q' is 310. It is to be noted that Wits=11.0 mm.

The OPE index Q' is 310, so it can be decided that the patient 8 does not need the surgical operation on the jaw in orthodontic treatment.

Example 168

From FIG. 14 showing the tracing made based on the cephalometric radiogram of the patient 9 taken in the example 9, the distances (S–A), (S–N), (S–B) and (Go–Me) were measured. The results are: (S–A)=79.0 mm, (S–N)=68.0 mm, (S–B)=105.0 mm and (Go–Me)=73.0 mm. Using the data, the calculation of P' is given as follows: (105.0+73.0)/(79.0+68.0)=1.2108. Therefore, the OPE index Q' is 210. It is to be noted that Wits=3.0 mm.

The OPE index Q' is 210, so it can be decided that the patient 9 does not need the surgical operation on the jaw in orthodontic treatment.

Example 169

From FIG. 15 showing the tracing made based on the cephalometric radiogram of the patient 10 taken in the example 10, the distances (S–A), (S–N), (S–B) and (Go–Me) were measured. The results are: (S–A)=81.0 mm, (S–N)=69.0 mm, (S–B)=103.0 mm and (Go–Me)=70.0 mm. Using the data, the calculation of P' is given as follows: (103.0+70.0)/(81.0+69.0)=1.1533. Therefore, the OPE index Q' is 153. It is to be noted that Wits=4.0 mm.

This is a case of non-skeletal. However, the OPE index Q' is 153, so it can be decided that the patient 10 does not need the surgical operation on the jaw in orthodontic treatment, and orthodontic treatment with a non-tooth extraction is adaptable.

Example 170

From FIG. 16 showing the tracing made based on the cephalometric radiogram of the patient 11 taken in the example 11, the distances (S–A), (S–N), (S–B) and (Go–Me) were measured. The results are: (S–A)=81.0 mm, (S–N)=63.0 mm, (S–B)=108.0 mm and (Go–Me)=68.0 mm. Using the data, the calculation of P' is given as follows: (108.0+68.0)/(81.0+63.0)=1.2222. Therefore, the OPE index Q' is 222. It is to be noted that Wits=2.0 mm.

The OPE index Q' is 222, and Wits is 2.0 mm, which shows a non-skeletal case. However, it can be decided that the patient 11 does not need the surgical operation on the jaw in orthodontic treatment, and orthodontic treatment with a non-tooth extraction is adaptable.

Example 171

From FIG. 17 showing the tracing made based on the cephalometric radiogram of the patient 12 taken in the example 12, the distances (S–A), (S–N), (S–B) and (Go–Me) were measured. The results are: (S–A)=91.0 mm, (S–N)=74.0 mm, (S–B)=115.0 mm and (Go–Me)=65.0 mm. Using the data, the calculation of P' is given as follows: (115.0+65.0)/(91.0+74.0)=1.0909. Therefore, the OPE index Q' is 90. It is to be noted that Wits=0.0 mm.

The OPE index Q' is 90, so it is a borderline case. It can be decided that the patient 12 shows a strong hypogrowth tendency of the mandible and does not need the surgical operation on the jaw in orthodontic treatment.

As explained, according to the method of calculating an index for deciding the necessity of surgically operating on the jaw of the twenty-seventh embodiment, using the distances (S–A), (S–N), (S–B) and (Go–Me) which are measured by cephalometric radiography, the OPE index Q' can be calculated. And based on the OPE index Q', the necessity of surgically operating on the jaw can be decided without being influenced by the experience of a dentist, and decided correctly with a short period of time, moreover with a certain objectivity.

28. Twenty-Eighth Embodiment

In the twenty-eighth embodiment, a method of deciding the necessity of surgically operating on the jaw in orthodontic treatment is explained.

As the same as the twenty-seventh embodiment, before executing the method of deciding the necessity of surgically operating on the jaw, the distances (S–A), (S–N), (S–B) and (Go–Me) are measured.

In step S161, the distances (S–A), (S–N), (S–B) and (Go–Me) which are measured by the above are entered.

In step S162, from the entered (S–A), (S–N), (S–B) and (Go–Me), P' is calculated according to $$P'=((S-B)+(Go-Me))/((S-A)+(S-N)).$$

In step S163, from P' obtained by the calculation, it is decided whether $1.000 \leq P' < 2.000$ or $P' < 1.000$. As a result of the decision, in case of $1.000 < P' < 2.000$, omitting the figures of the fourth decimal place and under of P', the OPE index Q' is calculated according to $$Q'=(P'-[P'])\times 1000$$

and in case of $P' < 1.000$, the OPE index Q' is calculated according to $$Q'=(P'-([P']+1))\times 1000.$$

In step S164, it is decided that the OPE index Q' calculated as the above is equal to or larger than 330 or not.

In step S165, in case that the OPE index Q' is equal to or larger than 330, it is decided that the severing operation on the mandible is necessary in orthodontic treatment.

In step S166, the result of decision that the severing operation on the mandible is necessary is output on a display, for example.

If Q' is decided to be not equal to or larger than 330 in step S164, in step S47, it is decided that Q' is equal to or larger than 270 and less than 330 or not.

In step S168, if the OPE index Q' is equal to or larger than 270 and less than 330, it is decided that Wits is equal to or larger than 12 mm or not. If Wits is equal to or larger than 12 mm, in step S169, it is decided that the surgical operation on the jaw is necessary.

If it is decided that the surgical operation on the jaw is necessary, in step S170, the result of decision is output on a display, for example.

If Wits is decided to be not equal to or larger than 12 mm in step S168, in step S171, it is decided that the surgical operation on the jaw is not necessary.

If it is decided that the surgical operation on the jaw is not necessary, in step S172, the result of decision is output on a display, for example.

If it is decided that Q' is not equal to or larger than 270 and less than 330 in step S167, in step S173, it is decided whether Q' is equal to or larger than 0 and less than 270 or not.

If the OPE index Q' is decided to be equal to or larger than 0 and less than 270, in step S174, it is decided that the surgical operation on the jaw is not necessary.

If it is decided that the surgical operation on the jaw is not necessary, in step S175, the result of decision is output on a display, for example.

If the OPE index Q' is not decided to be equal to or larger than 0 and less than 270, the OPE index Q' becomes negative. In this case, in step S176, a dentist decides the necessity of the surgical operation on the jaw, in step S177, the result of decision is output on a display, for example.

According to the method of deciding the necessity of surgically operating on the jaw of the twenty-eighth embodiment, based on the OPE index Q' to be calculated by using the distances (S–A), (S–N), (S–B) and (Go–Me) which are measured by cephalometric radiography, without being influenced by the experience of a dentist, the necessity of the surgical operation on the jaw in orthodontic treatment can be decided correctly with a short period of time, moreover with a certain objectivity.

29. Twenty-Ninth Embodiment

In the twenty-ninth embodiment, an index for deciding disharmony of the maxilla and mandible is calculated as the same as the method of calculating an index for deciding the necessity of surgically operating on the jaw in orthodontic treatment explained in the first embodiment.

According to the twenty-ninth embodiment, the index for deciding disharmony of the maxilla and mandible can be calculated easily. And based on the index for deciding disharmony of the maxilla and mandible, without being influenced by the experience of a dentist, disharmony of the maxilla and mandible in dental treatment such as orthodontic treatment, etc. can be decided correctly with a short period of time, moreover with a certain objectivity.

30. Thirtieth Embodiment

In the thirtieth embodiment, a method of deciding disharmony of the maxilla and mandible is carried out as the same as the method of deciding the necessity of surgically operating on the jaw in orthodontic treatment explained in the second embodiment.

According to the thirtieth embodiment, based on the index for deciding disharmony of the maxilla and mandible, without being influenced by the experience of a dentist, disharmony of the maxilla and mandible in dental treatment such as orthodontic treatment, etc. can be decided correctly with a short period of time, moreover with a certain objectivity.

31. Thirty-First Embodiment

In the thirty-first embodiment, an index for deciding disharmony of the maxilla and mandible is calculated as the same as the method of calculating an index for deciding the necessity of surgically operating on the jaw in orthodontic treatment explained in the third embodiment.

According to the thirty-first embodiment, the same advantages as the twenty-ninth embodiment can be obtained.

32. Thirty-Second Embodiment

In the thirty-second embodiment, a method of deciding disharmony of the maxilla and mandible is carried out as the same as the method of deciding the necessity of surgically operating on the jaw in orthodontic treatment explained in the twenty-eighth embodiment.

According to the thirty-second embodiment, the same advantages as the thirtieth embodiment can be obtained.

33. Thirty-Third Embodiment

In the thirty-third embodiment, an index for deciding dentofacial deformity is calculated as the same as the method of calculating an index for deciding the necessity of surgically operating on the jaw in orthodontic treatment explained in the twenty-seventh embodiment.

According to the thirty-third embodiment, the index for deciding dentofacial deformity can be calculated easily. And based on the index for deciding dentofacial deformity, without being influenced by the experience of a dentist or a doctor, dentofacial deformity can be decided correctly with a short period of time, moreover with a certain objectivity.

34. Thirty-Fourth Embodiment

In the thirty-fourth embodiment, a method of deciding dentofacial deformity is carried out as the same as the method of deciding the necessity of surgically operating on the jaw in orthodontic treatment explained in the twenty-eighth embodiment.

According to the thirty-fourth embodiment, based on the index for deciding dentofacial deformity, without being influenced by the experience of a dentist or a doctor, dentofacial deformity can be decided correctly with a short period of time, moreover with a certain objectivity.

Here, explained is a data processor which is used to carry out the method of calculating an index for deciding the necessity of surgically operating on the jaw, the method of deciding the necessity of surgically operating on the jaw, the method of calculating an index for deciding disharmony of the maxilla and mandible, the method of deciding disharmony of the maxilla and mandible, the method of calculating an index for deciding dentofacial deformity, the method of deciding dentofacial deformity, the method of calculating an index for deciding hypogrowth or overgrowth of the maxilla and a method of calculating an index for deciding hypogrowth or overgrowth of the mandible according to the first to the thirty-fourth embodiments.

Figure 34:
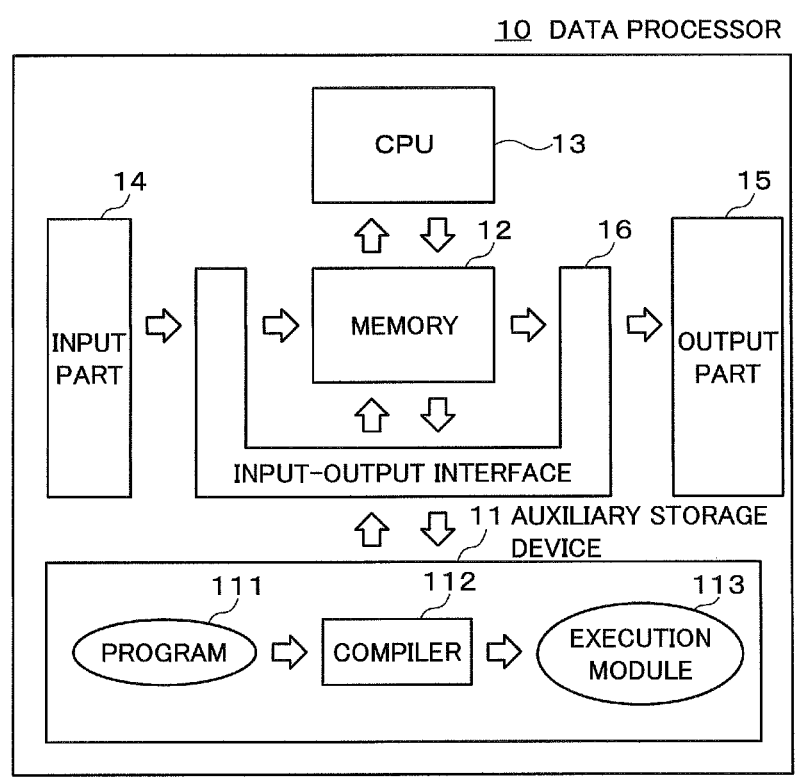
FIG. 34 A schematic drawing showing a data processor to be used for execution of the method of calculating an index for deciding the necessity of surgically operating on the jaw, the method of deciding the necessity of surgically operating on the jaw, the method of calculating an index for deciding disharmony of the maxilla and mandible, the method of deciding disharmony of the maxilla and mandible, the method of calculating an index for deciding dentofacial deformity, the method of deciding dentofacial deformity, the method of calculating an index for deciding hypogrowth or overgrowth of the maxilla, or the method of calculating an index for deciding hypogrowth or overgrowth of the mandible according to the first to thirty-fourth embodiments of the present invention.

FIG. 34 shows an example of the data processor 10. As shown in FIG. 34, the data processor 10 is comprised of an auxiliary storage device 11, a memory 12, a CPU (Central Processing Unit) 13 as a processing part, an input part 14, an output part 15 and an input-output interface 16.

The auxiliary storage device 11 is a device to store various kinds of information. For example, the auxiliary storage device 11 is comprised of a hard disk, a ROM (Read Only Memory), etc. The auxiliary storage device 11 stores a program 111, a compiler 112 and an execution module 113.

The program 111 is a program (source program) describing the processing on the flowcharts shown in FIG. 2, FIG. 18, FIG. 19 or FIG. 20. The compiler 112 compiles and links the program 111. The execution module 113 is a module which is compiled and linked by the compiler 112.

The memory 12 is temporary storing means to store various kinds of information, and is comprised of a RAM (Random Access Memory), etc., for example. The CPU 13 executes various types of arithmetic processing such as addition, subtraction, multiplication and division, etc., and plays a role executing the execution module 13 through the memory 12 and the input-output interface 16. The input part 14 is an input device to enter various kinds of execution commands, etc. The output part 15 is an output device to output the various kinds of execution results, etc. The input-output interface 16 is to mediate the input-output between each composition element of the data processor 10.

Next, the operation of the data processor 10 comprised as described above is explained. First, the compile commands entered from the input part 14 by an operator are stored in the memory 12 through the input-output interface 16. In the memory 12, the program 111 of the auxiliary storage device 11 is compiled and linked by the compiler 112, and the execution module 113 which is a machine language code is generated.

Next, by entering the execution commands from the input part 14 by an operator, the CPU 13 loads the execution module 113 in the memory 12. When the execution module 113 is loaded in the memory 12, by the CPU 13, each processing on the flowcharts shown in FIG. 2, FIG. 18, FIG. 19 or FIG. 20 is sequentially called to the CPU 13 from the memory 12, after executing each processing, the execution results are stored in the memory 12. The execution results stored in the memory 12 are output to the output part 15 through the input-output interface 16 by the CPU 13.

For example, in case of calculating the OPE index by executing the processing on the flowchart shown in FIG. 2, the following steps are taken. First, the execution module 113 to realize step S1 for input processing is called to the CPU 13 from the memory 12. In step S1, the data (distances (S–A), (S–B) and (Go–Me)) entered from the input part 14 by an operator are loaded to the memory 12. Finishing the input processing of step S1, the execution module 113 to realize step S2 of a calculation processing is called to the CPU 13 from the memory 12. In step S2, P is calculated by the entered data. Finishing the calculation processing of step S2, the execution module 113 to realize step S3 is called to the CPU 13 from the memory 12. In step S3, according to the size of P, the OPE index is calculated. Finishing the calculation processing of step S3, the execution module 113 to realize step S4 is called to the CPU 13 from the memory 12. In step S4, the value of P is output to the output part 15 as calculation results.

In case of performing the processing on the flowcharts shown in FIG. 18, FIG. 19 or FIG. 20, the processing is the same as the above.

Heretofore, embodiments and examples of the present invention have been explained specifically. However, the present invention is not limited to these embodiments and examples, but contemplates various changes and modifications based on the technical idea of the present invention.

For example, numerical numbers, flowcharts, etc. presented in the aforementioned embodiments and examples are only examples, and the different numerical numbers, flowcharts, etc. may be used as necessary.

And, for example, there may be used other mathematically equivalent equations that can obtain the index equivalent to the index which is calculated by $P=((S-X_i)+(Go-X_j))/(S-A)$, $P=((S-B)+(Go-B)+(Go-Me))/((S-A)+(Go-A))$ or equations (16) to (24). For example, each term of the denominator and numerator in the right side of these equations of P may be multiplied arbitrary coefficients, other terms may be added to the denominator or numerator, any constant may be added or subtracted to or from the denominator or numerator, or any constant may be added or subtracted to or from the right side. Concretely, for example, there may be used $P=(b(S-X_i)+c(Go-X_j))/a(S-A)+d$ (where a, b, c and d are real numbers) instead of $P=((S-X_i)+(Go-X_j))/(S-A)$.

EXPLANATION OF REFERENCE NUMERALS 10 data processor
11 auxiliary storage device
12 memory
13 CPU
14 input part
15 output part
16 input-output interface
111 program
112 compiler
113 execution module

The invention claimed is:

1. A method of calculating an index related to at least one of orthodontic treatment, dental treatment, and dentofacial deformity, the method comprising:

receiving input, by a processing device, of points of measurement from a cephalometric radiogram, the points of measurement comprising:

"S" representing Sella, a central point of the pot-shaped shaded image of the sella *turcica* of the sphenoid bone;

"A" representing the deepest point on the median sagittal plane between the forefront of the anterior nasal spine, which is on the forefront part of the palatine shelf of maxilla and the Prosthion, which is the most frontal point of an alveolar process between the upper central incisors;

"B" representing the deepest point between the infradentale, the most front point of the alveolar process between the lower central incisors and pogonion;

"Go" representing Gonion, a cross point of the angle of the mandible and the bisector of the cross angle between the line connecting the posterior plane of the head of the temporomandibular joint and the posterior part of the angle of the mandible and the mandibular plane;

"Pog" representing Pogonion, the most protruding point of protuberantia mentalis of the mandible for the Frankfort plane;

"Gn" representing Gnathion, a cross point of the bone edge image of protuberantia mentalis and the bisector of the angle between the facial plane and the mandibular plane, where the facial plane is the line connecting "N" and Pog, with "N" representing the front point of the frontal suture of the nasal bone;

"Me" representing the menton, the lowest point of the median section image of a chin;

measuring, by a processing device, distances comprising:
(S–A) representing the distance between points S and A;
(S–$X_i$) representing the distance between points S and $X_i$; and
(Go–$X_j$) representing the distance between points Go and $X_j$,
wherein i and j are each an integer from 1 to 4 and may or may not be equal to each other, with $X_1$=B, $X_2$=Pog, $X_3$=Gn and $X_4$=Me; and calculating, by a processing device, P=((S–$X_i$)+(Go–$X_j$))/(S–A), for all combinations of i and j excluding the case of $X_i$=B (i=1) and $X_j$=Me (j=4), wherein the index is for at least one of deciding the necessity of surgically operating on the jaw in orthodontic treatment, deciding disharmony of the maxilla and mandible in dental treatment, and deciding dentofacial deformity.

2. The method of calculating an index according to claim 1, further comprising omitting the figures of the fourth decimal place and under of P and calculating, by a processing device:

$Q=(P-[P])\times 1000$ ([ ] denotes Gauss's symbol) (where $2.000 \le P \le 3.000$)

or $Q=(P-([P]+1))\times 1000$ ([ ] denotes Gauss's symbol) (where $P<2.000$).

3. The method of calculating an index of claim 1, wherein receiving input, by a processing device, of points of measurement from a cephalometric radiogram comprises using image processing of cephalometric radiography by a processing device to detect and locate the points of measurement from image data.

4. A method of deciding at least one of the necessity of surgically operating on the jaw in orthodontic treatment, disharmony of the maxilla and mandible in dental treatment, and dentofacial deformity, the method comprising:

receiving input, by a processing device, of points of measurement from a cephalometric radiogram, the points of measurement comprising:

"S" representing Sella, a central point of the pot-shaped shaded image of the sella *turcica* of the sphenoid bone;

"A" representing the deepest point on the median sagittal plane between the forefront of the anterior nasal spine, which is on the forefront part of the palatine shelf of maxilla and the Prosthion, which is the most frontal point of an alveolar process between the upper central incisors;

"B" representing the deepest point between the infradentale, the most front point of the alveolar process between the lower central incisors and pogonion;

"Go" representing Gonion, a cross point of the angle of the mandible and the bisector of the cross angle between the line connecting the posterior plane of the head of the temporomandibular joint and the posterior part of the angle of the mandible and the mandibular plane;

"Pog" representing Pogonion, the most protruding point of protuberantia mentalis of the mandible for the Frankfort plane;

"Gn" representing Gnathion, a cross point of the bone edge image of protuberantia mentalis and the bisector of the angle between the facial plane and the mandibular plane, where the facial plane is the line connecting "N" and Pog, with "N" representing the front point of the frontal suture of the nasal bone;

"Me" representing the menton, the lowest point of the median section image of a chin;

measuring, by a processing device, distances comprising:
(S–A) representing the distance between points S and A;
(S–$X_i$) representing the distance between points S and $X_i$; and
(Go–$X_j$) representing the distance between points Go and $X_j$;
wherein i and j are each an integer from 1 to 4 and may or may not be equal to each other, with $X_1$=B, $X_2$=Pog, $X_3$=Gn and $X_4$=Me; and calculating, by a processing device, P=((S–$X_i$)+(Go–$X_j$))/(S–A), for all combinations of i and j excluding the case of $X_i$=B (i=1) and $X_j$=Me (j=4), or further omitting the figures of the fourth decimal place and under of P and calculating, by a processing device:

$Q=(P-[P])\times 1000$ ([ ] denotes Gauss's symbol) (where $2.000 \le P < 3.000$)

or $Q=(P-([P]+1))\times 1000$ ([ ] denotes Gauss's symbol) (where $P<2.000$); and deciding at least one of the necessity of surgically operating on the jaw, deciding disharmony of the maxilla and mandible, and whether a patient suffers from dentofacial deformity by determining whether calculated P or Q is equal to or larger than a predetermined value or not, respectively.

5. The method of claim 4, wherein receiving input, by a processing device, of points of measurement from a cephalometric radiogram comprises using image processing of cephalometric radiography by a processing device to detect and locate the points of measurement from image data.

6. A system for calculating an index related to at least one of orthodontic treatment, dental treatment, and dentofacial deformity, based on points of measurement identified from a cephalometric radiogram, the points of measurement comprising:

"S" representing Sella, a central point of the pot-shaped shaded image of the sella *turcica* of the sphenoid bone;

"A" representing the deepest point on the median sagittal plane between the forefront of the anterior nasal spine, which is on the forefront part of the palatine shelf of maxilla and the Prosthion, which is the most frontal point of an alveolar process between the upper central incisors;

"B" representing the deepest point between the infradentale, the most front point of the alveolar process between the lower central incisors and pogonion;

"Go" representing Gonion, a cross point of the angle of the mandible and the bisector of the cross angle between the line connecting the posterior plane of the head of the temporomandibular joint and the posterior part of the angle of the mandible and the mandibular plane;

"Pog" representing Pogonion, the most protruding point of protuberantia mentalis of the mandible for the Frankfort plane;

"Gn" representing Gnathion, a cross point of the bone edge image of protuberantia mentalis and the bisector of the angle between the facial plane and the mandibular plane, where the facial plane is the line connecting "N" and Pog, with "N" representing the front point of the frontal suture of the nasal bone;

"Me" representing the menton, the lowest point of the median section image of a chin;
the system comprising:
a processor;
a module, operating on the processor, for calculating the index related to at least one of orthodontic treatment, dental treatment, and dentofacial deformity, the module comprising:
a module for receiving input of the points of measurement;
a module for measuring distances comprising:
   (S–A) representing the distance between points S and A;
   (S–$X_i$) representing the distance between points S and $X_i$; and
   (Go–$X_j$) representing the distance between points Go and $X_j$, wherein i and j are each an integer from 1 to 4 and may or may not be equal to each other, with $X_1$=B, $X_2$=Pog, $X_3$=Gn and $X_4$=Me; and
a module for calculating P=((S–$X_i$)+(Go–$X_j$))/(S–A), for all combinations of i and j excluding the case of $X_i$=B (i=1) and $X_j$=Me (j=4).

7. The system of claim 6, further comprising a module for omitting the figures of the fourth decimal place and under of P and calculating:

$$Q=(P-[P])\times 1000 \text{ ([ ] denotes Gauss's symbol) (where } 2.000 \leq P < 3.000)$$

or $$Q=(P-([P]+1))\times 1000 \text{ ([ ] denotes Gauss's symbol) (where } P < 2.000).$$

8. The system of claim 6, wherein the module for receiving input of the points of measurement comprises a module for using image processing of cephalometric radiography by a processing device to detect and locate the points of measurement from image data.

9. A system for deciding at least one of the necessity of surgically operating on the jaw in orthodontic treatment, disharmony of the maxilla and mandible in dental treatment, and dentofacial deformity, based on points of measurement identified from a cephalometric radiogram, the points of measurement comprising:
   "S" representing Sella, a central point of the pot-shaped shaded image of the sella *turcica* of the sphenoid bone;
   "A" representing the deepest point on the median sagittal plane between the forefront of the anterior nasal spine, which is on the forefront part of the palatine shelf of maxilla and the Prosthion, which is the most frontal point of an alveolar process between the upper central incisors;
   "B" representing the deepest point between the infradentale, the most front point of the alveolar process between the lower central incisors and pogonion;
   "Go" representing Gonion, a cross point of the angle of the mandible and the bisector of the cross angle between the line connecting the posterior plane of the head of the temporomandibular joint and the posterior part of the angle of the mandible and the mandibular plane;
   "Pog" representing Pogonion, the most protruding point of protuberantia mentalis of the mandible for the Frankfort plane;
   "Gn" representing Gnathion, a cross point of the bone edge image of protuberantia mentalis and the bisector of the angle between the facial plane and the mandibular plane, where the facial plane is the line connecting "N" and Pog, with "N" representing the front point of the frontal suture of the nasal bone;
   "Me" representing the menton, the lowest point of the median section image of a chin;
a module, operating on the processor, for deciding at least one of the necessity of surgically operating on the jaw in orthodontic treatment, disharmony of the maxilla and mandible in dental treatment, and dentofacial deformity, the module comprising:
a module for receiving input of the points of measurement;
a module for measuring distances comprising:
   (S–A) representing the distance between points S and A;
   (S–$X_i$) representing the distance between points S and $X_i$; and
   (Go–$X_j$) representing the distance between points Go and $X_j$,
wherein i and j are each an integer from 1 to 4 and may or may not be equal to each other, with $X_i$=B, $X_2$=Pog, $X_3$=Gn and $X_4$=Me;
a module for calculating P=((S–$X_i$)+(Go–$X_j$))/(S–A), for all combinations of i and j excluding the case of $X_i$=B (i=1) and $X_j$=Me (j=4) and with such value of P or further omitting the figures of the fourth decimal place and under of P, for calculating:

$$Q=(P-[P])\times 1000 \text{ ([ ] denotes Gauss's symbol) (where } 2.000 \leq P < 3.000)$$

or $$Q=(P-([P]+1))'31000 \text{ ([ ] denotes Gauss's symbol) (where } P < 2.000).$$

10. The system of claim 9, wherein the module for receiving input of the points of measurement comprises a module for using image processing of cephalometric radiography by a processing device to detect and locate the points of measurement from image data.

11. A computer program product for calculating an index related to at least one of orthodontic treatment, dental treatment, and dentofacial deformity, the computer program product comprising:
   a computer readable storage medium having computer readable program code embodied therewith, the computer readable program code comprising:
      computer readable program code configured to receive input of points of measurement on a cephalometric radiogram, the points of measurement comprising:
         "S" representing Sella, a central point of the pot-shaped shaded image of the sella *turcica* of the sphenoid bone;
         "A" representing the deepest point on the median sagittal plane between the forefront of the anterior nasal spine, which is on the forefront part of the palatine shelf of maxilla and the Prosthion, which is the most frontal point of an alveolar process between the upper central incisors;
         "B" representing the deepest point between the infradentale, the most front point of the alveolar process between the lower central incisors and pogonion;
         "Go" representing Gonion, a cross point of the angle of the mandible and the bisector of the cross angle between the line connecting the posterior plane of the head of the temporomandibular joint and the posterior part of the angle of the mandible and the mandibular plane;
         "Pog" representing Pogonion, the most protruding point of protuberantia mentalis of the mandible for the Frankfort plane;

"Gn" representing Gnathion, a cross point of the bone edge image of protuberantia mentalis and the bisector of the angle between the facial plane and the mandibular plane, where the facial plane is the line connecting "N" and Pog, with "N" representing the front point of the frontal suture of the nasal bone;

"Me" representing the menton, the lowest point of the median section image of a chin;

computer readable program code configured to measure distances between the points of measurement, the distances measured comprising:

(S–A) representing the distance between points S and A;

(S–$X_i$) representing the distance between points S and $X_i$; and (Go–$X_j$) representing the distance between points Go and $X_j$, wherein i and j are each an integer from 1 to 4 and may or may not be equal to each other, with $X_1$=B, $X_2$=Pog, $X_3$=Gn and $X_4$=Me;

computer readable program code configured to calculate P=((S–$X_i$)+(Go–$X_j$))/(S–A), for all combinations of i and j excluding the case of $X_i$=B (i=1) and $X_j$=Me (j=4).

12. The computer program product of claim 11, further comprising computer readable program code configured to omit the figures of the fourth decimal place and under of P and to calculate:

$Q=(P-[P])\times 1000$ ([ ] denotes Gauss's symbol) (where $2.000 \leq P < 3.000$)

or $Q=(P-([P]+1))\times 1000$ ([ ] denotes Gauss's symbol) (where $P<2.000$).

13. The computer program product of claim 11, wherein the computer readable program code configured to receive input of points of measurement on a cephalometric radiogram comprises computer readable program code configured to use image processing of cephalometric radiography to detect and locate the points of measurement from image data.

14. A computer program product for deciding at least one of the necessity of surgically operating on the jaw in orthodontic treatment, disharmony of the maxilla and mandible in dental treatment, and dentofacial deformity, the computer program product comprising:

a computer readable storage medium having computer readable program code embodied therewith, the computer readable program code comprising:

computer readable program code configured to receive input of points of measurement on a cephalometric radiogram, the points of measurement comprising:

"S" representing Sella, a central point of the pot-shaped shaded image of the sella *turcica* of the sphenoid bone;

"A" representing the deepest point on the median sagittal plane between the forefront of the anterior nasal spine, which is on the forefront part of the palatine shelf of maxilla and the Prosthion, which is the most frontal point of an alveolar process between the upper central incisors;

"B" representing the deepest point between the infradentale, the most front point of the alveolar process between the lower central incisors and pogonion;

"Go" representing Gonion, a cross point of the angle of the mandible and the bisector of the cross angle between the line connecting the posterior plane of the head of the temporomandibular joint and the posterior part of the angle of the mandible and the mandibular plane;

"Pog" representing Pogonion, the most protruding point of protuberantia mentalis of the mandible for the Frankfort plane;

"Gn" representing Gnathion, a cross point of the bone edge image of protuberantia mentalis and the bisector of the angle between the facial plane and the mandibular plane, where the facial plane is the line connecting "N" and Pog, with "N" representing the front point of the frontal suture of the nasal bone;

"Me" representing the menton, the lowest point of the median section image of a chin;

computer readable program code configured to measure distances between the points of measurement, the distances measured comprising:

(S–A) representing the distance between points S and A;

(S–$X_i$) representing the distance between points S and $X_i$; and (Go–$X_j$) representing the distance between points Go and $X_j$, wherein i and j are each an integer from 1 to 4 and may or may not be equal to each other, with $X_1$=B, $X_2$=Pog, $X_3$=Gn and $X_4$=Me;

computer readable program code configured to calculate P=((S–$X_i$)+(Go–$X_j$))/(S–A), for all combinations of i and j excluding the case of $X_i$=B (i=1) and $X_j$=Me (j=4), and with such value of P or further omitting the figures of the fourth decimal place and under of P, the computer readable program code configured to calculate:

$Q=(P-[P])\times 1000$ ([ ] denotes Gauss's symbol) (where $2.000 \leq P < 3.000$)

or $Q=(P-([P]+1))\times 1000$ ([ ] denotes Gauss's symbol) (where $P<2.000$); and computer readable program code configured to determine whether calculated P or Q is equal to or larger than a predetermined value or not, respectively.

15. The computer program product of claim 14, wherein the computer readable program code configured to receive input of points of measurement on a cephalometric radiogram comprises computer readable program code configured to use image processing of cephalometric radiography to detect and locate the points of measurement from image data.

* * * * *

UNITED STATES PATENT AND TRADEMARK OFFICE
CERTIFICATE OF CORRECTION

PATENT NO. : 8,979,773 B2
APPLICATION NO. : 14/117743
DATED : March 17, 2015
INVENTOR(S) : Daiki Hirabayashi It is certified that error appears in the above-identified patent and that said Letters Patent is hereby corrected as shown below:

In the claims:

In column 87, claim 2, please change line 24 to:

$2.000 \leq P < 3.000)$

In column 90, claim 9, please change line 29 to:

$Q=(P-([P]+1)) \times 1000$ ([] denotes Gauss's symbol)

Signed and Sealed this
Twenty-first Day of July, 2015

Michelle K. Lee
*Director of the United States Patent and Trademark Office*